United States Patent
Lumeras Amador et al.

(10) Patent No.: US 10,696,665 B2
(45) Date of Patent: Jun. 30, 2020

(54) MUTANT IDH1 INHIBITORS

(71) Applicant: Eli Lilly and Company, Indianapolis, IN (US)

(72) Inventors: Wenceslao Lumeras Amador, Madrid (ES); Serge Louis Boulet, Fishers, IN (US); Timothy Paul Burkholder, Carmel, IN (US); Santiago Carballares Martin, Madrid (ES); Raymond Gilmour, Indianapolis, IN (US); Patric James Hahn, Indianapolis, IN (US); Renato Alejandro Bauer, Indianapolis, IN (US); Zoran Rankovic, Memphis, TN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/302,797

(22) PCT Filed: May 30, 2017

(86) PCT No.: PCT/US2017/034930
§ 371 (c)(1),
(2) Date: Nov. 19, 2018

(87) PCT Pub. No.: WO2017/213910
PCT Pub. Date: Dec. 14, 2017

(65) Prior Publication Data
US 2019/0292175 A1    Sep. 26, 2019

(30) Foreign Application Priority Data

Jun. 6, 2016 (EP) .................................... 16382257
Jan. 20, 2017 (EP) .................................... 17382025

(51) Int. Cl.
| | |
|---|---|
| C07D 213/04 | (2006.01) |
| C07D 413/14 | (2006.01) |
| A61K 31/506 | (2006.01) |
| A61P 35/00 | (2006.01) |
| C07D 413/04 | (2006.01) |

(52) U.S. Cl.
CPC ............ *C07D 413/14* (2013.01); *A61P 35/00* (2018.01); *C07D 413/04* (2013.01)

(58) Field of Classification Search
CPC .. C07D 413/04; C07D 413/14; A61K 31/506; A61K 31/496; A61P 35/00
USPC ..................................... 544/323; 514/252.13
See application file for complete search history.

(56) References Cited

U.S. PATENT DOCUMENTS

| | | |
|---|---|---|
| 2014/0235620 A1 | 8/2014 | Caferro et al. |
| 2016/0039802 A1 | 2/2016 | Cho et al. |
| 2017/0313696 A1 | 11/2017 | Saito et al. |

FOREIGN PATENT DOCUMENTS

| | | | |
|---|---|---|---|
| WO | 2013/046136 A1 | 4/2013 | |
| WO | 2014/141153 A1 | 9/2014 | |
| WO | 2014/147586 A1 | 9/2014 | |
| WO | 2017/019429 A1 | 2/2017 | |
| WO | WO-2018118793 A1 * | 6/2018 | ........... C07D 401/14 |

OTHER PUBLICATIONS

Cecil Textbook of Medicine, edited by Bennet, J.C., and Plum F., 20th edition, vol. 1, 1004-1010 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
International Search Report of PCT/US2017034930.
Written Opinion of PCT/US2017034930.
Cairns, RA and TW Mak, "Oncogenic Isocitrate Dehydrogenase Mutations: Mechanisms, Models, and Clinical Opportunities," *Cancer Discovery* 2013; 3: 730-741.
Dang et al., *IDH* mutations in glioma and acute myeloid leukemia, *Trends Mol. Med.* 2010; 16: 387-397.
Golub D, et al., "Mutant Isocitrate Dehydrogenase Inhibitors as Targeted Cancer Therapeutics," *Frontiers in Oncology* 2019; 9 (Article 417): 1-16.
Inman S, "Risk of Progression or Death Reduced With Ivosidenib in Advanced Cholangiocarcinoma," downloaded from targetdonc.com/conference/esmo-2019/risk of progression-death-reduced-with-ivosidenib-in-advanced-cholangiocarcinoma on Jan. 8, 2020 (3 pages).

* cited by examiner

*Primary Examiner* — Venkataraman Balasubramanian
(74) *Attorney, Agent, or Firm* — Grant E Reed

(57) ABSTRACT

The present application provides compounds of Formula I: Formula (I) that are useful as inhibitors of mutant IDH1, pharmaceutical compositions, and uses for the treatment of cancer.

(I)

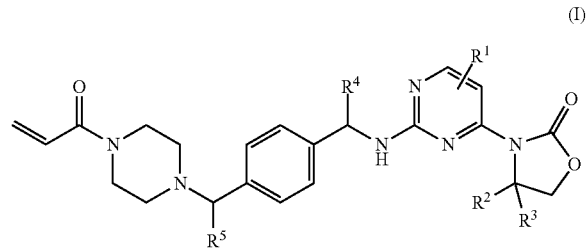

15 Claims, No Drawings

MUTANT IDH1 INHIBITORS

The isocitrate dehydrogenase (IDH) protein is an important enzyme in the citric acid (tricarboxylic acid or Krebs) cycle. The citric acid cycle is centrally important to many biochemical pathways and is one of the earliest established components of cellular metabolism.

Isocitrate dehydrogenases catalyze the oxidative decarboxylation of isocitrate to α-ketoglutarate (2-oxoglutarate). These enzymes belong to two distinct subclasses, one of which utilizes nicotinamide adenine dinucleotide (NAD(+)) as the electron acceptor and the other nicotinamide adenine dinucleotide phosphate (NADP(+)). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a dimer. The protein encoded by the IDH1 gene is the NADP(+)-dependent isocitrate dehydrogenase found in the cytoplasm and peroxisomes. The cytoplasmic enzyme serves a significant role in cytoplasmic NADPH production. IDH1 is expressed in a wide range of species and in organisms that lack a complete citric acid cycle.

Recently, mutations in IDH1, and the related isoform IDH2, have been found in several types of cancers. Mutations were found to occur at specific amino acids along the protein sequence and to be heterozygously expressed, consistent with a gain of function. These mutations occur at functionally conserved residues and biochemical studies of the mutant forms of IDH1 demonstrated a loss of normal function of IDH1, the reversible conversion of isocitrate to α-ketoglutarate. The result of these mutations is to allow a new (or neomorphic) conversion of α-ketoglutarate (αKG) to 2-hydroxyglutarate (2HG). As a result, cancer cells that harbor mutant forms of IDH1 or IDH2 form substantially higher concentrations of 2HG. High levels of 2HG result in a block in cell differentiation that can be reversed by mutant IDH1 or IDH2 inhibition.

Certain inhibitors of mutant IDH are described in WO 2013/046136. Application PCT/US2016/043264 discloses covalent inhibitors of mutant IDH1. There is a need for compounds that selectively inhibit mutant IDH1 enzyme over wild type IDH1 for the treatment of various cancers. There is a further need for compounds that selectively inhibit mutant IDH1 enzyme demonstrating neomorphic activity over wild type IDH1 for the treatment of various cancers. The present invention provides compounds of Formula I that are inhibitors of mutant IDH1. The compounds of Formula I are covalent inhibitors that selectively inhibit mutant IDH1 over wild type IDH1 and mutant IDH2 enzyme over wild type IDH2.

One aspect of the invention is to provide mutant IDH1 enzyme inhibitor compounds of Formula I:

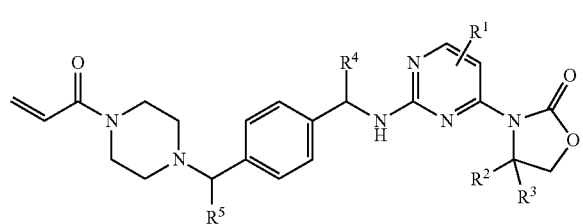

I wherein:
R$^1$ is hydrogen, NH$_2$, or fluoro;
R$^2$ and R$^3$ are methyl or hydrogen; or R$^2$ is methyl, ethyl, 1-hydroxyethyl, 1-methyoxyethyl, fluoromethyl, 1-fluoroethyl, or 1-methylethyl, and R$^3$ is hydrogen;
R$^4$ is methyl or fluoromethyl;
R$^5$ is hydrogen, ethyl, or —CH$_2$-cyclopropyl; or a pharmaceutically acceptable salt thereof.

A further aspect of the present invention provides a compound of Formula I wherein:
R$^1$ is hydrogen, 6-NH$_2$, or 6-fluoro;
R$^2$ and R$^3$ are methyl; or R$^2$ is 1-methyoxyethyl, or 1-methylethyl, and R$^3$ is hydrogen;
R$^4$ is methyl;
R$^5$ is hydrogen, ethyl, or —CH$_2$-cyclopropyl; or a pharmaceutically acceptable salt thereof.

Another aspect of the present invention provides a compound selected from:
(S)-3-(2-(((S)-1-(4-((4-acryloylpiperazin-1-yl)methyl)phenyl)ethyl)amino)pyrimidin-4-yl)-4-isopropyloxazolidin-2-one;
(S)-3-(2-((1-(4-((4-acryloylpiperazin-1-yl)methyl)phenyl)ethyl)amino)-6-fluoropyrimidin-4-yl)-4,4-dimethyloxazolidin-2-one;
(R)-3-(2-(((S)-1-(4-((4-acryloylpiperazin-1-yl)methyl)phenyl)ethyl)amino)pyrimidin-4-yl)-4-((R)-1-methoxyethyl)oxazolidin-2-one; and
(R)-3-(2-(((S)-1-(4-((4-acryloylpiperazin-1-yl)methyl)phenyl)ethyl)amino)-6-fluoropyrimidin-4-yl)-4-((R)-1-methoxyethyl)oxazolidin-2-one;
or a pharmaceutically acceptable salt of each of the above-mentioned compounds.

A further aspect of the present invention provides a compound:
(S)-3-(2-((1-(4-((4-acryloylpiperazin-1-yl)methyl)phenyl)ethyl)amino)-6-fluoropyrimidin-4-yl)-4,4-dimethyloxazolidin-2-one;
or a pharmaceutically acceptable salt thereof.

A still further aspect of the present invention provides a compound selected from:
(4S)-3-[2-[[(1S)-1-[4-[2-Cyclopropyl-1-(4-prop-2-enoylpiperazin-1-yl)ethyl]phenyl]ethyl]amino]pyrimidin-4-yl]-4-isopropyl-oxazolidin-2-one, isomer 1;
(4S)-3-[2-[[(1S)-1-[4-[2-Cyclopropyl-1-(4-prop-2-enoylpiperazin-1-yl)ethyl]phenyl]ethyl]amino]pyrimidin-4-yl]-4-isopropyl-oxazolidin-2-one, isomer 2;
3-[2-[[(1S)-1-[4-[2-Cyclopropyl-1-(4-prop-2-enoylpiperazin-1-yl)ethyl]phenyl]ethyl]amino]-6-fluoro-pyrimidin-4-yl]-4,4-dimethyl-oxazolidin-2-one, isomer 1;
3-[2-[[(1S)-1-[4-[2-Cyclopropyl-1-(4-prop-2-enoylpiperazin-1-yl)ethyl]phenyl]ethyl]amino]-6-fluoro-pyrimidin-4-yl]-4,4-dimethyl-oxazolidin-2-one, isomer 2;
3-[6-Amino-2-[[(1S)-1-[4-[1-(4-prop-2-enoylpiperazin-1-yl)propyl]phenyl]ethyl]amino]pyrimidin-4-yl]-4,4-dimethyl-oxazolidin-2-one, isomer 1;
3-[6-Amino-2-[[(1S)-1-[4-[1-(4-prop-2-enoylpiperazin-1-yl)propyl]phenyl]ethyl]amino]pyrimidin-4-yl]-4,4-dimethyl-oxazolidin-2-one, isomer 2;
or a pharmaceutically acceptable salt of any one of the above-mentioned compounds.

Another aspect of the present invention provides a pharmaceutical composition comprising a mutant IDH1 inhibitor compound of Formula I, or a pharmaceutically acceptable salt thereof, and a pharmaceutically acceptable carrier.

A further aspect of the present invention provides a method of treating a cancer expressing mutant IDH1 which is glioma, glioblastoma, glioblastoma multiforme (GBM), astrocytoma, oligodendroglioma, paraganglioma, fibrosarcoma, angioimmunoblastic T-cell lymphoma (AITL), myelodysplastic syndrome (MDS), B cell acute lymphoblastic leukemia (B-ALL), thyroid cancer, colorectal cancer, acute myeloid leukemia (AML), melanoma, prostate cancer, chondrosarcoma or cholangiocarcinoma in a patient comprising administering to a patient in need thereof a therapeutically effective amount of a compound of Formula I, or a pharmaceutically acceptable salt thereof.

Another aspect of the present invention provides a method of treating a cancer expressing mutant IDH1 which is glioma, glioblastoma, glioblastoma multiforme, astrocytoma, oligodendroglioma, paraganglioma, fibrosarcoma, or acute myeloid leukemia, in a patient comprising administering to a patient in need thereof a therapeutically effective amount of a compound of Formula I, or a pharmaceutically acceptable salt thereof.

A further aspect of the present invention provides a compound of Formula I, or a pharmaceutically acceptable salt thereof, for use in therapy.

Another aspect of the present invention provides a compound of Formula I, or a pharmaceutically acceptable salt thereof, for use in the treatment of a cancer expressing mutant IDH1 which is glioma, glioblastoma, glioblastoma multiforme, astrocytoma, oligodendroglioma, paraganglioma, fibrosarcoma, angioimmunoblastic T-cell lymphoma (AITL), myelodysplastic syndrome (MDS), B cell acute lymphoblastic leukemia (B-ALL), thyroid cancer, colorectal cancer, acute myeloid leukemia (AML), melanoma, prostate cancer, chondrosarcoma or cholangiocarcinoma.

A further aspect of the present invention provides a compound of Formula I, or a pharmaceutically acceptable salt thereof, for use in the treatment of a cancer expressing mutant IDH1 which is glioma, glioblastoma, glioblastoma multiforme, astrocytoma, oligodendroglioma, paraganglioma, fibrosarcoma, or acute myeloid leukemia Another aspect of the present invention provides use of a compound of Formula I, or a pharmaceutically acceptable salt thereof, for the manufacture of a medicament for the treatment of a cancer expressing mutant IDH1 which is glioma, glioblastoma, glioblastoma multiforme, astrocytoma, oligodendroglioma, paraganglioma, fibrosarcoma, angioimmunoblastic T-cell lymphoma (AITL), myelodysplastic syndrome (MDS), B cell acute lymphoblastic leukemia (B-ALL), thyroid cancer, colorectal cancer, acute myeloid leukemia (AML), melanoma, prostate cancer, chondrosarcoma or cholangiocarcinoma.

A further aspect of the present invention provides use of a compound of Formula I, or a pharmaceutically acceptable salt thereof, for the manufacture of a medicament for the treatment of a cancer expressing mutant IDH1 which is glioma, glioblastoma, glioblastoma multiforme, astrocytoma, oligodendroglioma, paraganglioma, fibrosarcoma, or acute myeloid leukemia.

The term "patient" means mammal and "mammal" includes, but is not limited to, a human.

"Therapeutically effective amount" means the dosage of the compound of Formula I, or pharmaceutically acceptable salt thereof, or pharmaceutical composition containing the compound, or pharmaceutically acceptable salt thereof, necessary to inhibit mutant IDH1 in a cancer patient, leading to the release of the block in differentiation with resulting inhibition of tumor cell growth and eliminate or slow or arrest the progression of the cancer in a patient. Anticipated dosages of a compound of Formula I, or a pharmaceutically acceptable salt thereof are in the range of 20 mg/patient/day to 2000 mg/patient/day. Preferred dosages are anticipated to be in the range of 30 mg/patient/day to 1800 mg/patient/day. Most preferred dosages are anticipated to be in the range of 40 mg/patient/day to 1600 mg/patient/day. The exact dosage required to treat a patient and the length of treatment time will be determined by a physician in view of the stage and severity of the disease as well as the specific needs and response of the individual patient. Although expressed as dosage on a per day basis, the dosing administration may be adjusted to provide a more optimal therapeutic benefit to a patient and to manage or ameliorate any drug related toxicities. In addition to daily dosing, twice a day (B.I.D.) dosing, three times a day (T.I.D.) dosing, dosing every other day (Q2D); every other day over a five day period followed by two days without dosing (T.I.W.); or every third day (Q3D) may be appropriate.

The terms "treatment," "treat," and "treating," are meant to include the full spectrum of intervention for the cancer from which the patient is suffering, such as administration of the active compound to alleviate, slow, or reverse one or more of the symptoms and to delay progression of the cancer even if the cancer is not actually eliminated.

A compound of Formula I, or a pharmaceutically acceptable salt thereof, is preferably formulated as a pharmaceutical composition using a pharmaceutically acceptable carrier and administered by a variety of routes. Preferably, such compositions are for oral administration. Such pharmaceutical compositions and processes for preparing them are well known in the art. See, for example, REMINGTON: THE SCIENCE AND PRACTICE OF PHARMACY, L. V. Allen, Editor, $22^{nd}$ Edition, Pharmaceutical Press, 2012. In a particular embodiment, the pharmaceutical composition comprises (S)-3-(2-((1-(4-((4-acryloylpiperazin-1-yl)methyl)phenyl)ethyl)amino)-6-fluoropyrimidin-4-yl)-4,4-dimethyloxazolidin-2-one or a pharmaceutically acceptable salt thereof, together with a pharmaceutically acceptable carrier and optionally other therapeutic ingredients particularly for treatment of cancer generally or a specific cancer type.

A compound of Formula I, or a pharmaceutically acceptable salt, may be administered either simultaneously with, or before, or after, one or more other therapeutic agents. The compound of formula I or a pharmaceutically acceptable salt, when administered with one or more other therapeutic agents, may be administered separately, by the same or different route of administration, or together in the same pharmaceutical composition as the other therapeutic agent(s). Where one or more additional therapeutic agents are administered, the administration of each therapeutic agent may be simultaneous, separate, or sequential.

A compound of Formula I, or a pharmaceutically acceptable salt thereof, may be prepared by a variety of procedures known in the art, as well as those described below. The specific synthetic steps may be combined in a different order to prepare a compound of Formula I, or a pharmaceutically acceptable salt thereof.

Compounds of Formula I are named according to IUPAC, and may also be named according to CAS, and other naming conventions may be used to unambiguously identify a compound of Formula I, or a pharmaceutically acceptable salt thereof.

It will be understood a compound of Formula I may have up to four chiral centers, including the carbon atoms bearing the $R^4$, $R^5$, and $R^2$ substituents, as well as a further possibility within the defined $R^2$ groups giving rise to multiple stereoisomers. It should be understood one, or more of the compounds may have one, two, three, or four of the stereoisomer structures and each isomer confirmed. A particular compound within Formula I may be depicted as a substantially enantiomerically pure stereoisomer having the configuration shown. For compounds of Formula I having a configuration with all stereocenters shown, "substantially enantiomerically pure" means the isomeric purity is greater than 90% enantiomeric excess. In another embodiment a compound of Formula I isomeric purity is greater than 95% enantiomeric excess at the $R^4$ and/or $R^5$ bearing carbon atom. In still another embodiment a compound of Formula I isomeric purity is greater than 98% enantiomeric excess at the $R^4$ and/or $R^5$ bearing carbon atom. In yet another embodiment a compound of Formula I isomeric purity is greater than 99% enantiomeric excess at the $R^4$ and/or $R^5$ bearing carbon atom. All stereoisomers, individually and including diastereomeric mixtures of the compounds of Formula I are contemplated within the scope of the present invention.

As used herein, references to a single stereoisomer are meant to also include stereoisomeric mixtures including the named or depicted compound of Formula I. Herein, the Cahn-Ingold-Prelog designations of (R)- and (S)-may be used to refer to specific stereoisomers. Specific stereoisomers can be prepared by stereospecific synthesis using enantiomerically pure or enriched starting materials. The specific stereoisomers of either starting materials, intermediates, or racemic mixtures including compounds of Formula I can be resolved by techniques well known in the art, such as those found in STEREOCHEMISTRY OF ORGANIC COMPOUNDS, E. I. Eliel and S. H. Wilen (Wiley 1994) and ENANTIOMERS, RACEMATES AND RESOLUTIONS, J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts. The designations "isomer 1" and "isomer 2" refer to the compounds that elute from chiral chromatography first and second, respectively, and if chiral chromatography is initiated early in the synthesis, the same designation is applied to subsequent intermediates and examples. The bond depicted as ⟿ refers to an isomeric mixture.

The compounds employed as initial starting materials in the synthesis of the compounds of Formula I are well known and, to the extent not commercially available, are readily synthesized using specific references provided, by standard procedures commonly employed by those of ordinary skill in the art or are found in general reference texts.

Examples of known procedures and methods include those described in general reference texts such as COMPREHENSIVE ORGANIC TRANSFORMATIONS, VCH Publishers Inc, 1989; COMPENDIUM OF ORGANIC SYNTHETIC METHODS, Volumes 1-10, 1974-2002, Wiley Interscience; MARCH'S ADVANCED ORGANIC CHEMISTRY: REACTIONS, MECHANISMS, AND STRUCTURE, 5$^{th}$ Edition, Michael B. Smith and Jerry March, Wiley Interscience, 2001; ADVANCED ORGANIC CHEMISTRY, 4$^{th}$ Edition, Part B, Reactions and Synthesis, Francis A. Carey and Richard J. Sundberg, Kluwer Academic/Plenum Publishers, 2000, etc., and references cited therein.

Certain stereochemical centers may be left unspecified in the following schemes for the sake of clarity and are not intended to limit the teaching of the schemes in any way. Individual isomers, enantiomers, and diastereomers may be separated or resolved by one of ordinary skill in the art at any convenient point in the synthesis of compounds of the invention, by methods such as selective crystallization techniques or chiral chromatography.

Certain abbreviations are defined as follows: "ACN" refers to acetonitrile; "αKG" refers to alpha-ketoglutarate or 2-ketoglutarate; "BCA" refers to bicinchoninic acid; "Boc" refers to tert-butoxy carbonyl; "BSA" refers to Bovine Serum Albumin; "CBZ" refers to carbobenzyloxy; "CDI" refers to 1,1'-carbonyldiimidazole or di(imidazole-1-yl) methanone; "DCC" refers to 1,3-dicyclohexylcarbodiimide; "1,2-DCE" refers to 1,2-dichloroethane; "DIC" refers to diisopropylcarbodiimide; "DIPEA" refers to diisopropylethylamine or N-ethyl-N-isopropyl-propan-2-amine; "DMAP" refers to dimethylaminopyridine; "DME" refers to dimethoxyethane; "DMEA" refers to dimethylethylamine; "DMF" refers to dimethylformamide; "DMSO" refers to dimethyl sulfoxide; "DTT" refers to dithiothreitol; "DPPF" refers to 1,1'-ferrocenediyl-bis(diphenylphosphino); "EDC" refers to EDAC, EDCI, or 1-(3-dimethylaminopropyl)-3-ethylcarbodiimide hydrochloride; "EDTA" refers to ethylenediaminetetraacetic acid; "ee" refers to enantiomeric excess; "EGTA" refers to ethylene glycol tetraacetic acid; "EtOAc" refers to ethyl acetate; "EtOH" refers to ethanol or ethyl alcohol; "Et$_2$O" refers to diethyl ether; "Ex" refers to example; "HATU" refers to (dimethylamino)-N,N-dimethyl (3H-[1,2,3]triazolo[4,5-b]pyridin-3-yloxy)methaniminium hexafluorophosphate; "HBTU" refers to 2-(1H-benzotriazole-1-yl)-1,1,3,3-tetramethyluronium hexafluorophosphate; "2HG" refers to 2-hydroxyglutarate; "d$_5$-3HG" refers to 3-hydroxy-1,5-pentanedioic-2,2,3,4,4-d$_5$ acid; "HILIC" refers to hydrophilic interaction liquid chromatography; "HOAt" refers to 1-hydroxy-7-azobenzotriazole; "HOBt" refers to 1-hydroxylbenzotriazole hydrate; "HPLC" refers to high-performance liquid chromatography; "IC$_{50}$" refers to the concentration of an agent that produces 50% of the maximal inhibitory response possible for that agent; "IPAm" refers to isopropylamine; "mCPBA" refers to meta-chloroperbenzoic acid; "MeOH" refers to methanol or methyl alcohol; "NADP$^+$" and "NAHPH" refers to the oxidized and reduced forms of nicotinamide adenine dinucleotide phosphate respectively; "OAc" refers to acetate; "PG" refers to protecting group; "Ph" refers to phenyl; "Prep" refers to preparation; "PyBOP" refers to benzotriazol-1-yloxytripyrrolidino-phosphonium hexafluorophosphate; "PyBrop" refers to bromo-tris-pyrrolidino phosphoniumhexafluoro phosphate; "rpm" refers to revolutions per minute; "R$_t$" refers to retention time; "SCX" refers to strong cation exchange; "SFC" refers to supercritical fluid chromatography; "S$_N$Ar" refers to nucleophilic aromatic substitution; "TEA" refers to triethylamine; "TFA" refers to trifluoroacetic acid; "THF" refers to tetrahydrofuran; and "Tris" refers to tris(hydroxymethyl)aminomethane.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Unless otherwise defined, $R^1$, $R^2$, $R^3$, $R^4$, and $R^5$ are as defined for Formula I.

Scheme 1

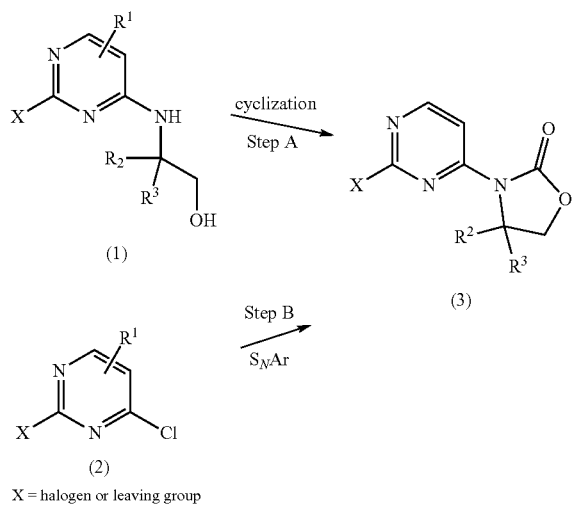

In Scheme 1, step A, a 2 substituted-4-amino ethanol pyrimidine (1) is cyclized to a substituted pyrimidine 2-oxazolidin-2-one (3) using an organic base such as triethylamine and di(imidazole-1-yl)methanone in a solvent such as THF. X on the pyrimidine can be a halogen or other leaving group such as methyl sulfonyl. Alternatively, for compound (2) the halo can be displaced with the amine of a substituted oxazolidin-2-one in a $S_NAr$ reaction to afford compound (3), the product of step B.

4-[1-(halomethyl)phenyl]ethanamine with a piperazine under alkylation conditions can also result in compound (4). In substep 1, Step C, the protected amine of compound (4) can be deprotected. For example, the 1-phenylethylamine can be deprotected under standard deprotection conditions using alkaline conditions such as exposure to aqueous sodium hydroxide in a solvent such as EtOH to give the free amine product of substep 1, Step C. Alternatively, if the protecting group is a carboxybenzyl group, hydrogenolysis conditions such as using 10% Pd/C in a solvent such as EtOH under a hydrogen atmosphere can provide the deprotected product of Step C, substep 1. The deprotected amine of compound (4) can then be alkylated in substep 2, Step C with a 2,4,6-trifluoro substituted pyrimidine in a $S_NAr$ reaction with a solvent such as $Et_2O$ at a temperature of about −50 to −20° C. to give compound (5), the product of substep 2, Step C. A second $S_NAr$ arylation can be completed on the 4-halogen, or 4, [5 or 6]-dihalogen substituted pyrimidine to displace the 4-halogen with the nitrogen of the substituted oxazolidine-2-one using a base such as sodium hydride in a solvent such as DMF at a temperature of about 0° C. to give compound (6), the product of Step D.

In an alternative route, in substep 1, Step E, compound (4) can be deprotected as described in substep 1, Step C and then alkylated in a $S_NAr$ reaction in substep 2, Step E. For example, after deprotection, the product of substep 1, Step E can be arylated with a 2-substituted pyrimidine-6-one where the 2-position is a leaving group such as methylsulfanyl in a solvent such as DME at a temperature of about 120° C. under microwave conditions to give compound (7), the product of substep 2, Step E. The pyrimidone (7) can be

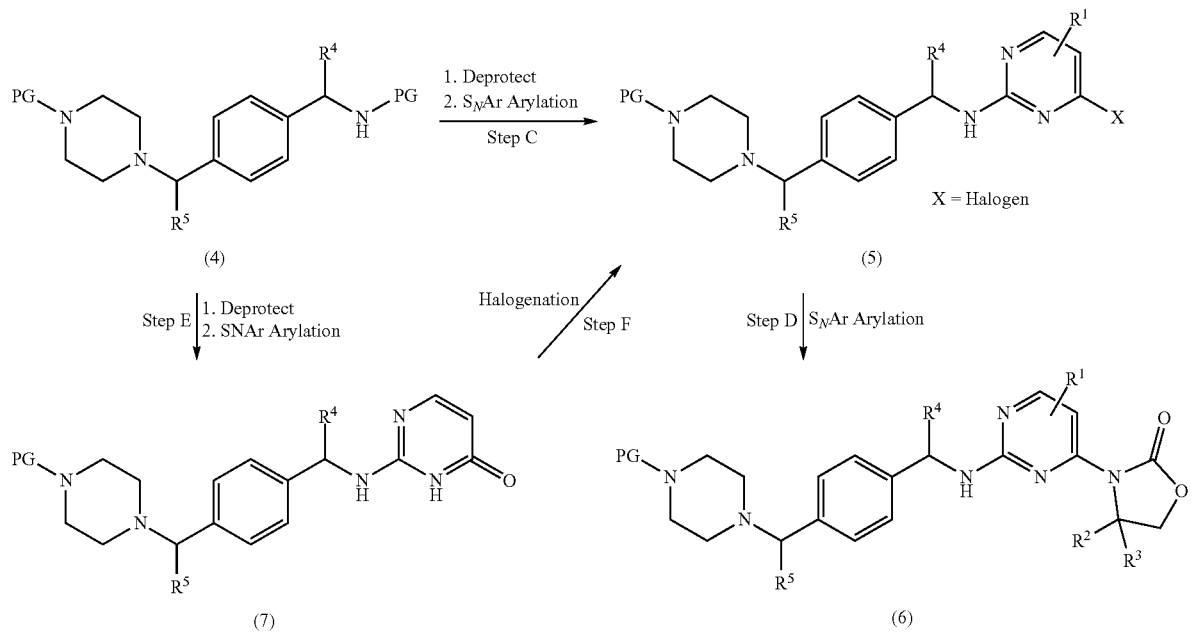

In Scheme 2, compound (4) can be prepared by a variety of procedures known by a person skilled in the art. For example, a reductive amination of a substituted 4-(1-aminoethyl)benzaldehyde and a piperazine can give compound (4). Alternatively, the displacement of a halide from a halogenated using a triphenylphosphine resin in a solvent such as 1,2-DCE with carbon tetrachloride and heating at about 70° C. to give compound (5) the product of Step F. Compound (5) can then be carried on in the same manner as described earlier for Step D to give to compound 6.

Scheme 3

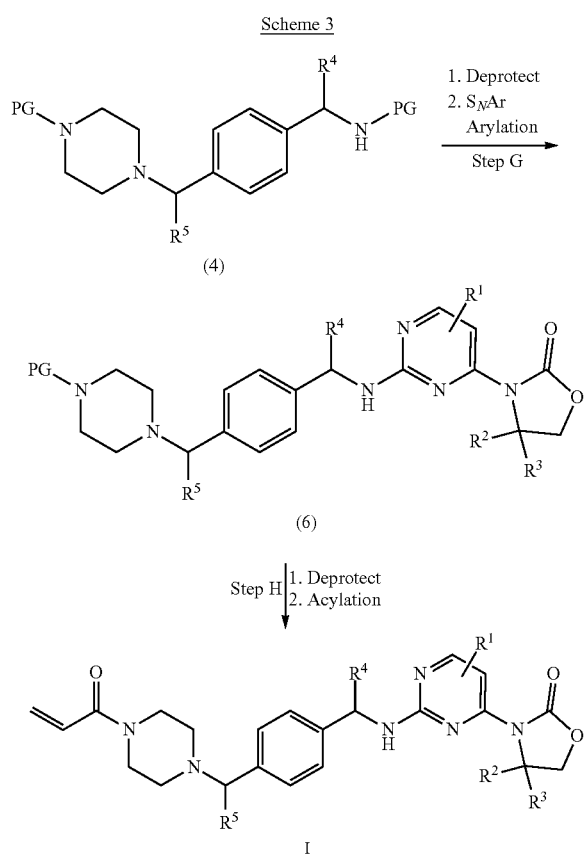

Alternatively, in Scheme 3, substep 1, Step G, the 1-phenylethylamine compound (4) can be deprotected as described in Scheme 2, substep 1, Step C to give the deprotected product of Step G, substep 1. The 1-phenylethylamine can then be reacted with compound (3), the product of Scheme 1, Step A or B in a S$_N$Ar reaction using an organic base such as DIPEA, cesium fluoride to accelerate the reaction, in a solvent such as DMSO, and at a temperature of about 70-100° C. to give compound (6) the product of substep 2, Step G, the analogous product of Scheme 2, step D. For those compounds of Formula I where R$^1$ is an —NH$_2$ substituent, the protected piperazine (6) of Scheme 2, step D, or Scheme 3, step G, is amine alkylated (amino-dehalohalogenation) by reacting a 5 or 6 fluorpyrimidine with ammonium hydroxide in a DMSO solution in a pressure vessel with heating overnight. The protected piperazine (6) can be deprotected with acidic deprotecting methods such as HCl in dioxane and MeOH or TFA in CH$_2$Cl$_2$ to give the deprotected piperazine of substep 1, Step H. If the R$^2$ or R$^3$ group of the oxazolidinone is protected with an acid labile group such as O-t-butyl, deprotection of this group can be accomplished along with deprotection of the piperazine in the same operation. In substep 2, Step H, the piperazine amine can be acylated with acryloyl chloride at a temperature of −78 to 0° C. with or without an organic base such as triethylamine in a solvent such as CH$_2$Cl$_2$ to give compounds of Formula I. A person skilled in the art would know that an amide coupling can be accomplished with acrylic acid and the appropriate amine in a solvent such as DMF with a coupling reagent such as EDC and an additive such as HOBt. One skilled in the art will also recognize that there are a number of methods and reagents for amide formation resulting from the reaction of carboxylic acids and amines. For example, the reaction of the appropriate amine and acrylic acid in the presence of a coupling reagent with or without an organic base such as DIPEA or TEA can provide a compound of Formula I. Other coupling reagents include carbodiimides, such as DCC, DIC, or a carbonyldiimidazole such as CDI. Other amide coupling additives, such as HOAt can also be used to enhance the reaction. Additionally, uronium or phosphonium salts of non-nucleophilic anions, such as HBTU, HATU, PyBOP, and PyBrOP could be used in place of the more traditional coupling reagents. An additive such as DMAP may also be used to accelerate the desired amidation reaction and give compounds of Formula I.

A compound of Formula I is capable of reaction with a number of inorganic and organic acids to form pharmaceutically acceptable acid addition salt. In an optional step, a pharmaceutically acceptable salt of a compound of Formula I can be formed by reaction of an appropriate free base of Formula I with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, P. Stahl, et al., Handbook of Pharmaceutical Salts: Properties, Selection and Use, (VCHA/Wiley-VCH, 2002); P. L. Gould, "Salt selection for basic drugs," *International Journal of Pharmaceutics*, 33: 201-217 (1986); R. J. Bastin, et al. "Salt Selection and Optimization Procedures for Pharmaceutical New Chemical Entities," *Organic Process Research and Development*, 4: 427-435 (2000); and S. M. Berge, et al., "Pharmaceutical Salts," *Journal of Pharmaceutical Sciences*, 66: 1-19, (1977). One of ordinary skill in the art will appreciate that a compound of Formula I is readily converted to and may be isolated as a pharmaceutically acceptable salt.

PREPARATION 1

(1S)-1-[4-(Chloromethyl)phenyl]ethanamine Hydrochloride

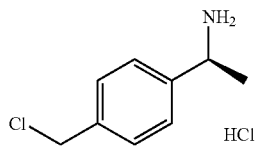

To a solution of (S)-(4-(1-aminoethyl)phenyl)methanol (81.8 g, 541 mmol) in CH$_2$Cl$_2$ (2.5 L) is added SOCl$_2$ (80 mL, 1.1 mmol) dropwise over 30 minutes while maintaining a reaction temperature below 25° C. After stirring for 4 hours, the mixture is concentrated to give a yellow solid. ACN (1 L) is added, the mixture is concentrated to 500 mL and the resulting solid is filtered to give an off-white solid that is dried under vacuum to give a first lot of the title compound. The mother liquor can also be concentrated to provide a less pure product (~20 g) as a yellow solid. The two product lots are combined to give the title compound (111 g, 78%). MS (m/z): 170 (M+H).

PREPARATION 2 tert-Butyl 4-[[4-[(1S)-1-[(2,2,2-trifluoroacetyl)amino]ethyl]phenyl]-methyl]-piperazine-1-carboxylate

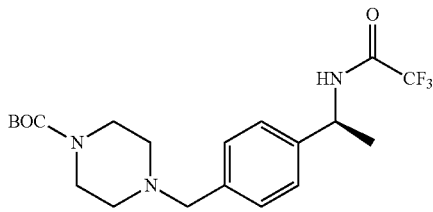 [SMILES: C[C@H](NC(=O)C(F)(F)F)c1ccc(CN2CCN(C(=O)OC(C)(C)C)CC2)cc1]

To a solution of (1S)-1-[4-(chloromethyl)phenyl]ethanamine hydrochloride (10 g, 48.5 mmol) in $CH_2Cl_2$ (160 mL) is added trifluoroacetic anhydride (8.2 mL, 58 mmol) at 0° C. TEA (15 mL, 108 mmol) is added while maintaining the addition temperature below 5° C. After stirring for 1 hour at 0° C. the reaction mixture is concentrated to dryness and ACN (120 mL) is added followed by tert-butyl piperazine-1-yl carbonate (13.5 g, 72.5 mmol). $K_2CO_3$ (20 g, 144.7 mmol) is added and the mixture is heated to 60° C. and stirred for 17 hours. The solvent is removed by vacuum and EtOAc (1 L) is added to give a solid. The solid is removed by filtration and the EtOAc solution is washed with water and brine. The organic phase is dried over $Na_2SO_4$, filtered, and concentrated to dryness to give a residue which is purified by silica gel chromatography (10 to 50% acetone/$CH_2Cl_2$) to give the title compound as a white foam (15.8 g, 78%). MS (m/z): 416 (M+H).

PREPARATION 3

2,2,2-Trifluoro-N-[(1 S)-1-[4-(hydroxymethyl)phenyl]ethyl]acetamide

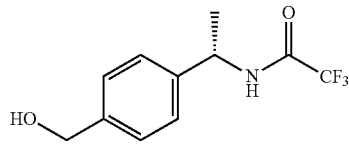 [SMILES: C[C@H](NC(=O)C(F)(F)F)c1ccc(CO)cc1]

Trifluoroacetic anhydride (12 mL, 85.4 mmol) is added to a 0° C. solution of [4-[(1S)-1-aminoethyl]phenyl]methanol (10.8 g, 71.4 mmol) in $CH_2Cl_2$ (150 mL). After 10 minutes, TEA (24 mL, 172 mmol) in $CH_2Cl_2$ (8 mL) is added dropwise over 30 minutes, the cooling bath is removed and the reaction is stirred overnight. The reaction mixture is concentrated under vacuum, diluted with additional $CH_2Cl_2$, and washed with 1 N aqueous HCl and water. The organic phase is dried ($Na_2SO_4$), filtered, and concentrated. The crude material is purified by silica gel chromatography eluting with a gradient of 0-50% EtOAc/hexanes to give the title compound as a white solid (11.1 g, 44.9 mmol, 63%). ES/MS (m/z): 246 (M–H).

PREPARATION 4

(S)-2,2,2-Trifluoro-N-(1-(4-formylphenyl)ethyl)acetamide

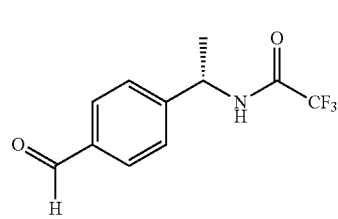 [SMILES: C[C@H](NC(=O)C(F)(F)F)c1ccc(C=O)cc1]

Dess-Martin periodinane (20.9 g, 49.3 mmol) is added to a 0° C. solution of 2,2,2-trifluoro-N-[(1S)-1-[4-(hydroxymethyl)phenyl]ethyl]acetamide (11.1 g, 44.9 mmol) in $CH_2Cl_2$ (450 mL). The reaction mixture is stirred overnight and allowed to warm to room temperature. The reaction mixture is diluted with additional $CH_2Cl_2$ and washed with saturated aqueous $NaHCO_3$, saturated aqueous $Na_2S_2O_3$, and brine. The combined organics are dried ($Na_2SO_4$), filtered, and concentrated to give a residue which is purified by silica gel chromatography eluting with a gradient of 0-50% EtOAc/hexanes to give the title compound as a white solid (9.5 g, 39 mmol, 86%). ES/MS (m/z): 244 (M–H).

PREPARATION 5

2,2,2-Trifluoro-N-((1 S)-1-(4-(1-hydroxypropyl)phenyl)ethyl)acetamide

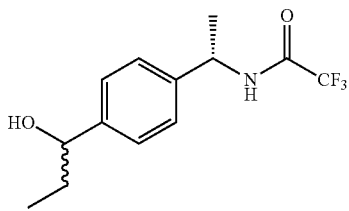 [SMILES: CCC(O)c1ccc([C@H](C)NC(=O)C(F)(F)F)cc1]

Ethylmagnesium bromide (12.23 mL, 36.7 mmol, 3 M in $Et_2O$) is added over 15 minutes to a solution of (S)-2,2,2-trifluoro-N-(1-(4-formylphenyl)ethyl)acetamide (4.5 g, 18.35 mmol) in THF (100 mL) at 0° C. After 45 minutes the reaction mixture is quenched by addition of saturated aqueous $NH_4Cl$ and is partitioned between EtOAc and water. The organic layer is separated and is washed with brine, dried ($Na_2SO_4$), filtered, and concentrated to give the title compound as a waxy white solid (5.74 g, 19 mmol, 91% purity) which is used without further purification. ES/MS (m/z): 274 (M–H).

PREPARATION 6

N-((1S)-1-(4-(1-Chloropropyl)phenyl)ethyl)-2,2,2-trifluoroacetamide

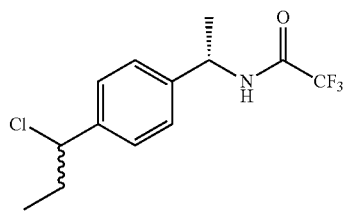 [SMILES: CCC(Cl)c1ccc([C@H](C)NC(=O)C(F)(F)F)cc1]

Thionyl chloride (4.63 mL, 63.6 mmol) is added dropwise to a solution of 2,2,2-trifluoro-N-((1S)-1-(4-(1-hydroxypropyl)phenyl)ethyl)acetamide (5 g, 18.2 mmol) in $CH_2Cl_2$ (150 mL) at 0° C. The reaction mixture is stirred at room temperature for 2 hours. The mixture is concentrated to give the title compound as a beige solid (5.33 g, 18.2 mmol, 100%) which is used without further purification. ES/MS (m/z): 292 (M−H).

PREPARATION 7

N-[(1S)-1-[4-(2-Cyclopropylacetyl)phenyl]ethyl]-2,2,2-trifluoro-acetamide

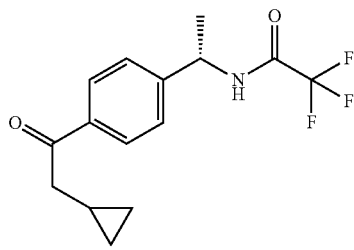 [SMILES: C[C@H](NC(=O)C(F)(F)F)c1ccc(C(=O)CC2CC2)cc1]

n-Butyl lithium (2.5 M in hexanes, 53 mL, 130 mmol) is added dropwise to a solution of N-[(1S)-1-(4-bromophenyl)ethyl]-2,2,2-trifluoro-acetamide (18.00 g, 60.79 mmol) in THF (600 mL) at −78° C. so as to maintain an internal temperature below −70° C. After the addition is complete, the mixture is stirred for 45 minutes at −78° C. and 2-cyclopropyl-N-methoxy-N-methyl-acetamide (11.4 g, 79.6 mmol) is added as a solution in THF (10 mL). The mixture is stirred at −78° C. for 45 minutes, saturated aqueous ammonium chloride is added, and the mixture is warmed to room temperature. The layers are separated and the organic layer is dried over anhydrous sodium sulfate, filtered, and concentrated under reduced pressure. To the solid is added a small amount of $CH_2Cl_2$ and the mixture is heated briefly to dissolve the solids. The mixture is concentrated until just before precipitation and then hexanes (150 mL) is added dropwise with vigorous stirring to give a colorless solid. The solid is collected via filtration, washed with a small amount of hexanes, and dried under reduced pressure to give the title compound (13.82 g, 76%) as a colorless solid. MS (m/z): 298.3 (M−H).

PREPARATION 8

Benzyl (1-(4-bromophenyl)-2-fluoroethyl)carbamate

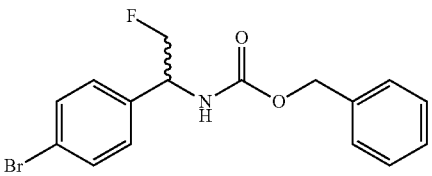 [SMILES: O=C(NC(CF)c1ccc(Br)cc1)OCc1ccccc1]

Sodium carbonate (17 g, 160.3 mmol) is added to a biphasic solvent mixture of water (115 mL) and $CH_2Cl_2$ (60 mL) containing 1-(4-bromophenyl)-2-fluoro-ethanamine (10 g, 45.9 mmol) at room temperature. The mixture is cooled to 0° C. and benzyl chloroformate (8.45 mL, 57.3 mmol) is added dropwise. After stirring for 2 hours at 0° C. the reaction mixture is allowed to stir overnight at room temperature and is then diluted with $CH_2Cl_2$ and washed with saturated aqueous $NaHCO_3$, water, and brine. The organic phase is dried ($Na_2SO_4$), filtered, concentrated, and dissolved in a minimum amount of EtOAc. Hexanes are added until a precipitate is observed and the solids are filtered and washed with additional hexanes. The title compound is obtained as a beige solid (12 g, 34.1 mmol, 74%). ES/MS (m/z): 352 (M+H).

PREPARATION 9

Methyl 4-(1-(((benzyloxy)carbonyl)amino)-2-fluoroethyl)benzoate

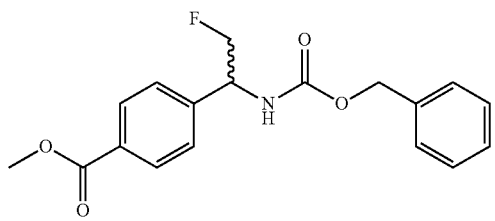 [SMILES: COC(=O)c1ccc(C(CF)NC(=O)OCc2ccccc2)cc1]

To a Parr autoclave is added $Pd(OAc)_2$ (774 mg, 3.28 mmol), DPPF (2.3 g 4 mmol), benzyl (1-(4-bromophenyl)-2-fluoroethyl)carbamate (12 g, 34.1 mmol), MeOH (120 mL), $CH_3CN$ (180 mL), and TEA (12 mL). The vessel is sealed, purged, and pressurized with CO gas (100 psi). The reaction is stirred at 85° C. for 24 hours and then allowed to cool to room temperature. The Parr reactor is vented and the reaction mixture is concentrated. The desired product is purified by silica gel chromatography eluting with 50% EtOAc/hexanes followed by precipitation from a minimum of EtOAc and slow addition of hexanes. The title compound is obtained as an orange solid (9.5 g, 29 mmol, 84%). ES/MS (m/z): 332 (M+H).

PREPARATION 10

4-(1-(((Benzyloxy)carbonyl)amino)-2-fluoroethyl)benzoic acid

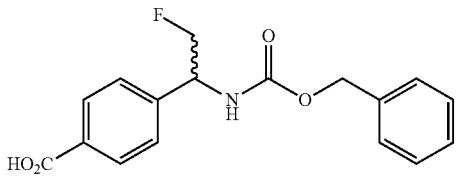 [SMILES: O=C(NC(CF)c1ccc(C(=O)O)cc1)OCc1ccccc1]

MeOH (80 mL) and 2 N aqueous sodium hydroxide (80 mL, 160 mmol) are added to a solution of methyl 4-(1-(((benzyloxy)carbonyl)amino)-2-fluoroethyl)benzoate (9.5 g, 29 mmol) in THF (160 mL) at room temperature. After stirring overnight, the reaction mixture is acidified with 6 N aqueous HCl to a pH of 4. The mixture is extracted with CH$_2$Cl$_2$, dried (Na$_2$SO$_4$), filtered, and concentrated to give the title product as a beige solid (9.2 g, 29 mmol, 100%), which is used without further purification. ES/MS (m/z): 316 (M−H).

PREPARATION 11

Benzyl (2-fluoro-1-(4-(hydroxymethyl)phenyl)ethyl)carbamate

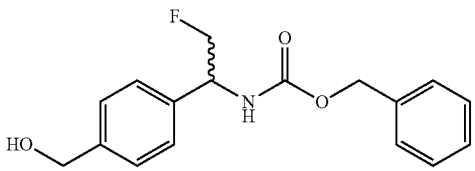 [SMILES: O=C(NC(CF)c1ccc(CO)cc1)OCc1ccccc1]

Borane dimethyl sulfide (51 mL, 102 mmol, 2 N in THF) is added dropwise to a solution of 4-(1-(((benzyloxy)carbonyl)amino)-2-fluoroethyl)benzoic acid (9.2 g, 29 mmol) in THF (150 mL) at 0° C. The reaction is warmed to 70° C. for 2.5 hours. After cooling to room temperature the reaction mixture is quenched by dropwise addition of MeOH until no further gas evolution is observed. The reaction mixture is then concentrated, redissolved in MeOH, and concentrated again. This MeOH-addition/concentration is repeated twice to give the title compound as a yellow-brown oil (6.65 g, 21.9 mmol, 76%) and is used without further purification. ES/MS (m/z): 304 (M+H).

PREPARATION 12

(4-(1-Amino-2-fluoroethyl)phenyl)methanol

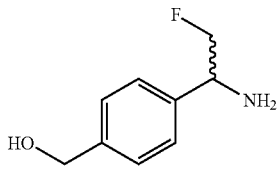 [SMILES: NC(CF)c1ccc(CO)cc1]

A solution of benzyl (2-fluoro-1-(4-(hydroxymethyl)phenyl)ethyl)carbamate (6.65 g, 21.9 mmol) in EtOH (200 mL) is added to 10 wt % palladium on carbon (2.33 g, 2.19 mmol) suspended in EtOH (200 mL). After purging the solution with N$_2$, and filling with H$_2$, an inlet of H$_2$ (balloon) is added and the reaction is allowed to stir overnight at room temperature. The solution is filtered through diatomaceous earth. Additional 10 wt % palladium on carbon (2.33 g, 2.19 mmol) is added to the filtrate and the reaction mixture is stirred for an additional 6 hours under a balloon of H$_2$. The solution is filtered over diatomaceous earth and the filtrate is concentrated to dryness to give the title compound as a grey solid (3.9 g, 16 mmol, 70% purity) and is used without further purification. ES/MS (m/z): 170 (M+H).

PREPARATION 13

1-(4-(Chloromethyl)phenyl)-2-fluoroethan-1-amine hydrochloride

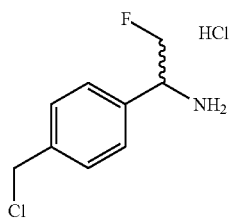 [SMILES: NC(CF)c1ccc(CCl)cc1 ; Cl]

Thionyl chloride (4.7 mL, 65 mmol) is added to a solution of (4-(1-amino-2-fluoroethyl)phenyl)methanol (3.9 g, 16 mmol, 70% purity) in CH$_2$Cl$_2$ (80 mL) at 0° C. The reaction is stirred at room temperature for 4 hours. The solids are filtered off and are washed with Et$_2$O and then taken up in water and extracted with CH$_2$Cl$_2$, diluted further with MeOH, and concentrated to give a residue which is purified by reverse phase chromatography eluting with 10-100% CH$_3$CN/H$_2$O to give the title compound as a white solid (2.4 g, 11 mmol, 66%). ES/MS (m/z): 188 (M+H).

PREPARATION 14 tert-Butyl 4-(4-(1-amino-2-fluoroethyl)benzyl)piperazine-1-carboxylate

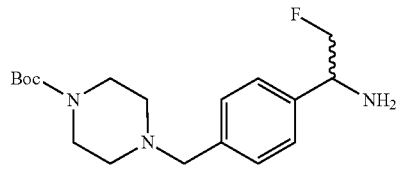 [SMILES: CC(C)(C)OC(=O)N1CCN(Cc2ccc(C(N)CF)cc2)CC1]

Potassium carbonate (5.9 g, 43 mmol) is added to a solution of 1-(4-(chloromethyl)phenyl)-2-fluoroethan-1-amine hydrochloride (2.4 g, 11 mmol) and tert-butyl piperazine-1-carboxylate (4 g, 21.5 mmol) in ACN (50 mL) at room temperature. The reaction mixture is stirred at 60° C. for 24 hours, cooled to room temperature, and concentrated. The crude reaction is suspended in CH$_2$Cl$_2$ and washed with saturated aqueous NaHCO$_3$ and brine. The organic phase is dried (Na$_2$SO$_4$), filtered, and concentrated to give a residue which is purified by reverse phase chromatography eluting with 10-100% CH₃CN/aqueous ammonium-bicarbonate to give the title compound as a yellow oil (2.47 g, 7.32 mmol, 68%). ES/MS (m/z): 338 (M+H).

PREPARATION 15 tert-Butyl 4-[[4-[(1S)-1-aminoethyl]phenyl]methyl]piperazine-1-carboxylate

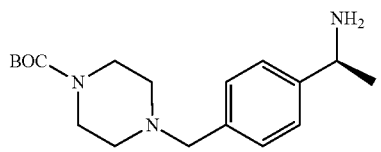 [SMILES: C[C@H](N)c1ccc(CN2CCN(C(=O)OC(C)(C)C)CC2)cc1]

To a solution of tert-butyl 4-[[4-[(1S)-1-[(2,2,2-trifluoroacetyl)amino]ethyl]phenyl]-methyl]-piperazine-1-carboxylate (203 g, 0.489 mol) in EtOH (2.4 L) is added 5 M aqueous NaOH (480 mL, 2.40 mol) at room temperature. After stirring at room temperature for 3.5 hours, the reaction mixture is concentrated to remove most of the EtOH. EtOAc (2 L) is added to dissolve the residue and the organic solution is washed with water and brine. The combined aqueous phases are extracted with EtOAc (2×). The combined organic extracts are dried over Na₂SO₄, filtered, and concentrated to dryness to give the crude title compound as a yellow viscous oil (156 g, 93%) which is used without further purification. MS (m/z): 320 (M+H).

PREPARATION 16 tert-Butyl 4-(1-(4-((S)-1-(2,2,2-trifluoroacetamido)ethyl)phenyl)propyl)piperazine-1-carboxylate

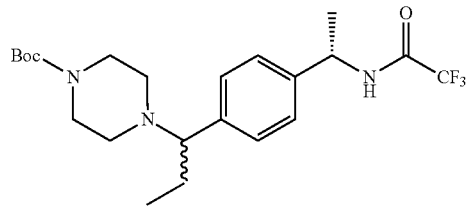 [SMILES: CCC(c1ccc([C@H](C)NC(=O)C(F)(F)F)cc1)N1CCN(C(=O)OC(C)(C)C)CC1]

K₂CO₃ (9.2 g, 67 mmol) and NaI (1.5 g, 10 mmol) are added to a solution of N-((1S)-1-(4-(1-chloropropyl)phenyl)ethyl)-2,2,2-trifluoroacetamide (4.9 g, 17 mmol) and 1-Boc-piperazine (3.7 g, 20 mmol) in CH₃CN (90 mL). The mixture is stirred at 90° C. for 3 hours and is then allowed to cool to room temperature. The solids are filtered away and the filtrate is concentrated and purified by silica gel chromatography eluting with 10-40% EtOAc/hexanes to give the title compound as an oil (5.56 g, 12.5 mmol, 75%). ES/MS (m/z): 444 (M+H).

PREPARATION 17 tert-Butyl 4-[2-cyclopropyl-1-[4-[(1S)-1-[(2,2,2-trifluoroacetyl)amino]ethyl]phenyl]ethyl]piperazine-1-carboxylate

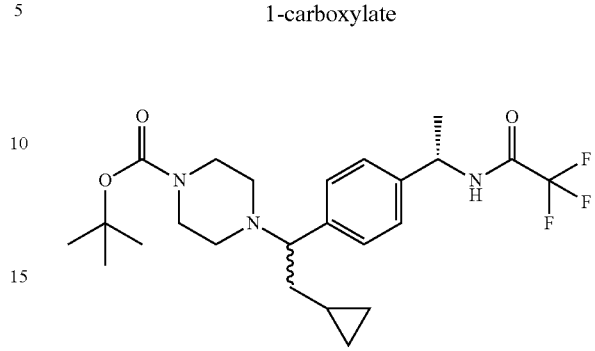

Titanium(IV) isopropoxide (60 mL, 200 mmol) is added to a solution of N-[(1S)-1-[4-(2-cyclopropylacetyl)phenyl]ethyl]-2,2,2-trifluoro-acetamide (12.0 g, 40.1 mmol) and tert-butyl piperazine-1-carboxylate (17.9 g, 96.1 mmol) in THF (80 mL) and the mixture is stirred at 60° C. overnight. The mixture is cooled to room temperature and MeOH (80 mL) is added followed by the portion-wise addition of sodium cyanoborohydride (5.3 g, 80 mmol). The mixture is stirred at room temperature for 8 hours and then water and MeOH are added and the mixture is stirred at room temperature overnight. The mixture is filtered to remove solids and the solids are rinsed with MeOH and water. The filtrate is partially concentrated to remove most of the MeOH and the residue is extracted with EtOAc (2×). The combined organic extracts are dried over anhydrous sodium sulfate, filtered, and concentrated under reduced pressure. The crude material is purified via silica gel column chromatography eluting with a gradient of 0% to 30% EtOAc in solvent B where solvent B is 1:1 hexanes:CH₂Cl₂ to give the title compound (10.5 g, 56%) as a colorless solid. MS (m/z): 470.3 (M+H).

PREPARATION 18 tert-Butyl 4-(1-(4-((S)-1-aminoethyl)phenyl)propyl)piperazine-1-carboxylate

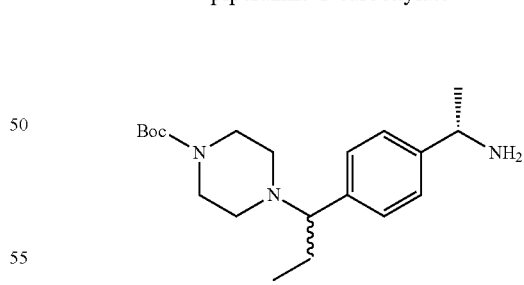

KOH (3.52 g, 62.7 mmol) is added in water (11 mL) to a solution of tert-butyl 4-(1-(4-((S)-1-(2,2,2-trifluoroacetamido)ethyl)phenyl)propyl)piperazine-1-carboxylate (5.56 g, 12.5 mmol) in EtOH (50.1 mL). The mixture is stirred for 3 hours at room temperature, concentrated, and partitioned between CH₂Cl₂ and saturated aqueous NaHCO₃. The organic phase is separated and is washed with brine, dried (Na₂CO₃), filtered, and concentrated to give the title compound as an oil (4.31 g, 12 mmol, 96%) which is used without further purification. ES/MS (m/z): 348 (M+H).

PREPARATION 19 tert-Butyl 4-[1-[4-[(1S)-1-aminoethyl]phenyl]-2-cyclopropyl-ethyl]piperazine-1-carboxylate

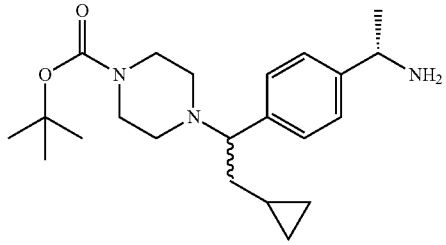 [SMILES: C[C@H](N)c1ccc(C(CC2CC2)N2CCN(C(=O)OC(C)(C)C)CC2)cc1]

Aqueous KOH (5 M, 69 mL, 350 mmol) is added to a solution of tert-butyl 4-[2-cyclopropyl-1-[4-[(1S)-1-1[(2,2,2-trifluoroacetyl)amino]ethyl]phenyl]ethyl]piperazine-1-carboxylate (32.24 g, 68.67 mmol) in EtOH (350 mL) and the resulting mixture is stirred at room temperature for 4 hours. The EtOH is removed under reduced pressure and to the residue is added saturated aqueous sodium bicarbonate and the mixture is extracted with $CH_2Cl_2$. The combined organic extracts are dried over anhydrous sodium sulfate, filtered, and concentrated under reduced pressure to give the title compound (24.33 g, 96.5% purity containing, 3.5% residual $CH_2Cl_2$, 92% yield) as a colorless viscous oil. MS (m/z): 374.3 (M+H).

PREPARATION 19a tert-Butyl 4-[1-[4-[(1S)-1-aminoethyl]phenyl]-2-cyclopropyl-ethyl]piperazine-1-carboxylate, Isomer 1

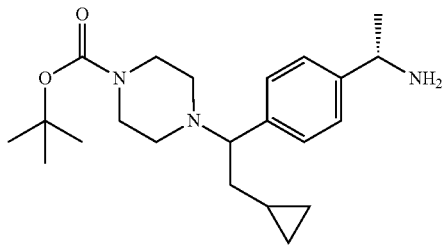 [SMILES: C[C@H](N)c1ccc(C(CC2CC2)N2CCN(C(=O)OC(C)(C)C)CC2)cc1]

PREPARATION 19b tert-Butyl 4-[1-[4-[(1S)-1-aminoethyl]phenyl]-2-cyclopropyl-ethyl]piperazine-1-carboxylate, isomer 2

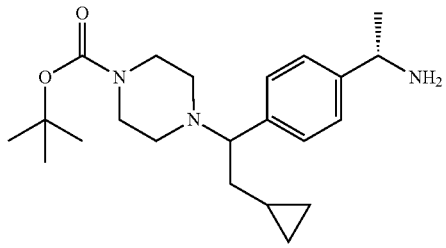 [SMILES: C[C@H](N)c1ccc(C(CC2CC2)N2CCN(C(=O)OC(C)(C)C)CC2)cc1]

tert-Butyl 4-[1-[4-[(1S)-1-aminoethyl]phenyl]-2-cyclopropyl-ethyl]piperazine-1-carboxylate (3.23 g) is dissolved in MeOH (40 mL) and is separated into individual diastereomers by preparative chiral HPLC chromatography using the following conditions: column Chiralpak AD, 20 μm, (8×33 cm); injection volume 10 mL; eluent 100% methanol with 0.2% DMEA; detection wavelength 220 nm; flow rate 400 mL/min. Example 19a, tert-butyl 4-[1-[4-[(1S)-1-aminoethyl]phenyl]-2-cyclopropyl-ethyl]piperazine-1-carboxylate, isomer 1 is obtained from the first eluting peak as a clear viscous oil (1.50 g, 46%, >99% de, $R_t$=4.2 minutes). MS (m/z): 374.3 (M+H). Example 19b, tert-butyl 4-[1-[4-[(1S)-1-aminoethyl]phenyl]-2-cyclopropyl-ethyl]piperazine-1-carboxylate, isomer 2 is obtained from the second eluting peak as a clear viscous oil (1.46 g, 45%, >98.2% de, $R_t$=5.7 minutes). MS (m/z): 374.3 (M+H).

PREPARATION 20

2-((2-(Methylthio)pyrimidin-4-yl)amino)ethan-1-ol

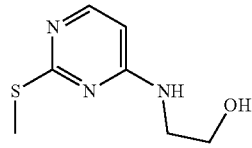

DIPEA (5 mL, 29 mmol) is added to a solution of 4-chloro-2-methylsulfanyl-pyrimidine (4.2 g, 26 mmol) and 2-aminoethanol (3.2 g, 52 mmol) in $CH_3CN$ (60 mL). The mixture is stirred at 80° C. for 2 hours and is then concentrated at 50° C. The crude product is taken up in EtOAc and is washed with water, dried ($Na_2CO_3$), filtered, and concentrated. The material is purified by silica gel chromatography eluting with a gradient of 0 to 100% EtOAc/hexanes to give the title compound as a white solid (3.33 g, 18.0 mmol, 69%). ES/MS (m/z): 186 (M+H).

PREPARATION 21

(S)-3-(2-Chloropyrimidin-4-yl)-4-ethyloxazolidin-2-one

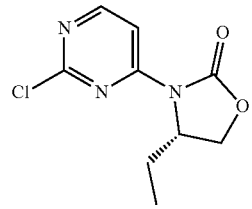

TEA (0.864 mL, 6.2 mmol) is added to a solution of (2S)-2-[(2-chloropyrimidin-4-yl)amino]butan-1-ol (1.25 g, 6.2 mmol) [Ger. Offenlegungsschrift, 102009001438, 16 Sep. 2010] and di(imidazole-1-yl)methanone (1.21 g, 7.44 mmol) in THF (12.4 mL) at room temperature. After stirring for 5 hours, additional di(imidazole-1-yl)methanone (1.21 g, 7.44 mmol) and TEA (0.864 mL, 6.2 mmol) are added and the resulting mixture is warmed to 50° C. and is stirred for 3 hours. The heating is removed and the resulting mixture is allowed to sit for 16 hours before diluting with water and extracting with EtOAc (3×). The combined organic extracts are then washed with 1 M aqueous HCl and brine, dried (MgSO₄), filtered, and concentrated to give the title compound as a white solid (1.20 g, 5.27 mmol, 85%). ES/MS (m/z): 228 (M+H).

The following compound is prepared in essentially the same manner as the method of Preparation 21 using the appropriate reagent.

TABLE 1

| Prep. No. | Chemical Name | Structure | ES/MS (m/z) (M + H) |
|---|---|---|---|
| 22 | 3-(2-(Methylthio) pyrimidin-4-yl) oxazolidin-2-one | 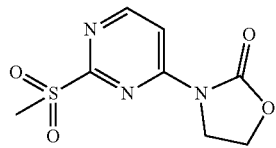 [SMILES: CS(=O)(=O)c1nccc(N2CCOC2=O)n1] | 212 |

PREPARATION 23

3-(2-(Methylsulfonyl)pyrimidin-4-yl)oxazolidin-2-one mCPBA (7.4 g, 30 mmol, 70 wt %) is added to a solution of 3-(2-methylsulfanylpyrimidin-4-yl)oxazolidin-2-one (3.0 g, 14 mmol) in CH₂Cl₂ (71 mL) at room temperature. After stirring for 1 hour the solids are filtered off and the filtrate is concentrated to give a solid. The solid is triturated with Et₂O and dried under vacuum to give the title compound as a white solid (2.63 g, 9.30 mmol, 86% purity). ES/MS (m/z): 244 (M+H).

PREPARATION 24

(S)-3-(2-Chloropyrimidin-4-yl)-4-methyloxazolidin-2-one

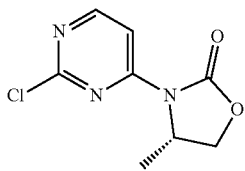

Sodium hydride (379 mg, 9.48 mmol, 60% in mineral oil) is added as a solid to a solution of 2,4-dichloropyrimidine (1.47 g, 9.89 mmol) and (S)-4-methyloxazolidin-2-one (877 mg, 8.2 mmol, 95% purity) in DMF (16.5 mL) at room temperature. After stirring for 16 hours at room temperature the mixture is quenched with saturated aqueous NH₄Cl and extracted with EtOAc (3×). The organic extracts are combined, dried (MgSO₄), filtered, and concentrated. The crude material is dissolved in 9:1 CH₂Cl₂/MeOH and the undesired white solids are filtered away. The crude product obtained in the filtrate is purified by silica gel chromatography eluting with a gradient of 5%-100% EtOAc/hexanes to give the title compound as a white solid (518 mg, 2.42 mmol, 29%). ES/MS (m/z): 214 (M+H).

PREPARATION 25

Benzyl ((2R,3S)-3-(tert-butoxy)-1-hydroxybutan-2-yl)carbamate

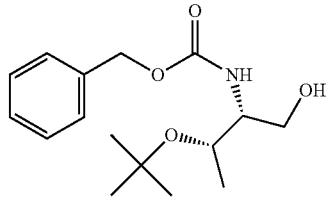 [SMILES: C[C@H](OC(C)(C)C)[C@@H](CO)NC(=O)OCc1ccccc1]

4-Methylmorpholine (0.540 mL, 4.9 mmol) is added to isobutyl chloroformate (0.640 mL, 4.90 mmol) and N-cyclohexylcyclohexanammonium (2S,3S)-2-(benzyloxycarbonylamino)-3-tert-butoxy-butanoate (2.00 g, 4.08 mmol) in THF (30 mL) at −25° C. After 10 minutes a solid is removed by filtration and rinsed with a minimum of anhydrous THF. The filtrate is cooled to −20° C. and sodium borohydride (231 mg, 6.1 mmol) is added followed by water (4 mL). The mixture is stirred for 10 minutes at −20° C. and then is stirred room temperature for 2 hours. Water is added and the mixture is extracted with EtOAc (2×). The combined organic extracts are washed with brine, dried (Na₂SO₄), filtered, and concentrated to give the title compound as a yellow oil (1.367 g, 3.93 mmol, 85% purity). ES/MS (m/z): 240 (M+H-t-butyl).

The following compound is prepared in essentially the same manner as the method of Preparation 25 using the appropriate reagent.

TABLE 2

| Prep. No. | Chemical Name | Structure | ES/MS (m/z) |
|---|---|---|---|
| 26 | Benzyl ((2R,3R)-3-(tert-butoxy)-1-hydroxybutan-2-yl) carbamate | 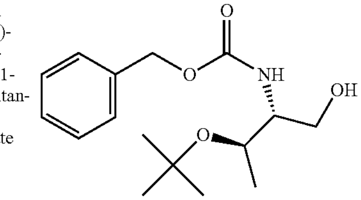 | 240 (M + H-t-butyl) |

PREPARATION 27

(R)-4-((S)-1-(tert-butoxy)ethyl)-3-(4-methoxybenzyl)oxazolidin-2-one

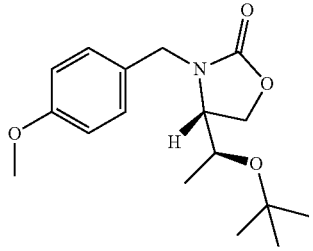 [SMILES: COc1ccc(CN2C(=O)OC[C@@H]2[C@H](C)OC(C)(C)C)cc1]

Sodium hydride (616 mg, 15.4 mmol, 60% in mineral oil) is added at 0° C. to a solution of benzyl ((2R,3S)-3-(tert-butoxy)-1-hydroxybutan-2-yl)carbamate (2.61 g, 7.51 mmol) in DMF (40 mL) and the mixture is stirred for 30 minutes. 4-Methoxybenzyl chloride (1.49 mL, 11.3 mmol) and tetrabutylammonium iodide (277 mg, 0.749 mmol) are added to the mixture and the solution is allowed to warm to room temperature, and stirred overnight. The reaction mixture is poured over ice water (200 mL) and EtOAc is added while stirring. The EtOAc layer is separated and the aqueous phase is extracted with additional EtOAc (2×). The combined EtOAc extracts are washed with 5% aqueous LiCl (2×), dried ($Na_2SO_4$), filtered, and concentrated to give a residue that is purified by silica gel chromatography eluting with 0-20% EtOAc/hexanes to give the title compound (1.91 g, 6.21 mmol, 83%). ES/MS (m/z): 308 (M+H).

The following compound is prepared in essentially the same manner as the method of Preparation 27 using the appropriate reagent.

TABLE 3

| Prep. No. | Chemical Name | Structure | ES/MS (m/z) (M + H) |
|---|---|---|---|
| 28 | (4R)-4-[(1R)-1-tert-Butoxyethyl]-3-[(4-methoxyphenyl)methyl]oxazolidin-2-one | 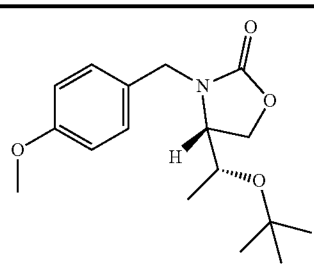 | 308 |

PREPARATION 29

(R)-4-((S)-1-hydroxyethyl)-3-(4-methoxybenzyl)oxazolidin-2-one

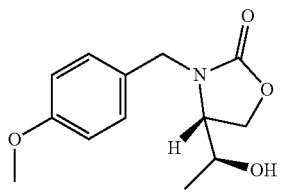 [SMILES: COc1ccc(CN2C(=O)OC[C@@H]2[C@H](C)O)cc1]

TFA (15 mL, 198 mmol) is added to a solution of (R)-4-((S)-1-(tert-butoxy)ethyl)-3-(4-methoxybenzyl)oxazolidin-2-one (2.31 g, 7.51 mmol) in $CH_2Cl_2$ (15 mL) at room temperature and the mixture is stirred for 20 minutes and concentrated to dryness. The crude product is redissolved in additional $CH_2Cl_2$ and concentrated. The addition of $CH_2Cl_2$ and concentration is repeated once more to give title compound as a yellow oil (1.97 g, 7.51 mmol, 100%) which is used without further purification. ES/MS (m/z): 252 (M+H).

The following compound is prepared in essentially the same manner as the method of Preparation 29 using the appropriate reagent.

TABLE 4

| Prep. No. | Chemical Name | Structure | ES/MS (m/z) (M + H) |
|---|---|---|---|
| 30 | (4R)-4-[(1R)-1-Hydroxyethyl]-3-[(4-methoxyphenyl)methyl]oxazolidin-2-one | 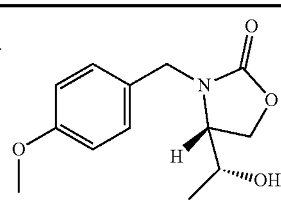 | 252 |

PREPARATION 31

(R)-4-((R)-1-Fluoroethyl)-3-(4-methoxybenzyl)oxazolidin-2-one

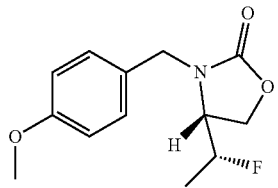 [SMILES: COc1ccc(CN2C(=O)OC[C@@H]2[C@@H](C)F)cc1]

A solution of (R)-4-((S)-1-hydroxyethyl)-3-(4-methoxybenzyl)oxazolidin-2-one (985 mg, 3.92 mmol) in $CH_3CN$ (13 mL) is treated with TEA (5 mL, 35.9 mmol) at 0° C.

Nonafluorobutane sulfonyl fluoride (2.11 mL, 11.7 mmol) and triethylamine trihydrofluoride (1.94 mL, 11.7 mmol) are added sequentially and the mixture is stirred for 1 hour at 0° C. Additional nonafluorobutane sulfonyl fluoride (0.9 mL, 5 mmol), triethylamine trihydrofluoride (1 mL, 6 mmol), and TEA (2.5 mL, 17.95 mmol) are added and the mixture is stirred for 45 minutes at 0° C. Further nonafluorobutane sulfonyl fluoride (1.05 mL, 5.8 mmol), triethylamine trihydrofluoride (1 mL, 6 mmol), and TEA (2.5 mL, 17.95 mmol) are added and the mixture is stirred for 30 minutes. The mixture is quenched with water and extracted with EtOAc (3×). The combined organic extracts are washed with brine, dried ($Na_2SO_4$), filtered, and concentrated. The crude mixture is taken up in $CH_2Cl_2$ and the solids are filtered away. The resulting filtrate is concentrated and the residue is purified by silica gel chromatography eluting with a gradient of 20-60% EtOAc/hexanes to give the title compound as a yellow oil (300 mg, 1.18 mmol, 30%). ES/MS (m/z): 254 (M+H).

The following compound is prepared in essentially the same manner as the method of Preparation 31 using the appropriate reagent.

TABLE 5

| Prep. No. | Chemical Name | Structure | ES/MS (m/z) (M + H) |
|---|---|---|---|
| 32 | (R)-4-((S)-1-Fluoroethyl)-3-(4-methoxybenzyl)oxazolidin-2-one | 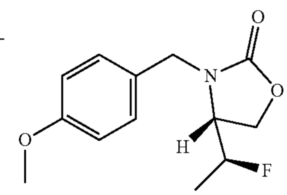 | 254 |

PREPARATION 33

(R)-4-((R)-1-Fluoroethyl)oxazolidin-2-one

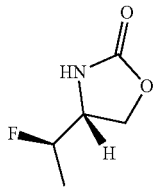

A solution of (R)-4-((R)-1-fluoroethyl)-3-(4-methoxybenzyl)oxazolidin-2-one (290 mg, 1.15 mmol) in TFA (6 mL) is heated for 40 hours at 65° C. The mixture is cooled to room temperature and concentrated. The crude product is redissolved in additional CH₂Cl₂ and is concentrated. This is repeated once more to remove residual TFA. The crude residue is purified by silica gel chromatography eluting with a gradient of 30-80% EtOAc/CH₂Cl₂ to give the title compound as an amber oil (141 mg, 1.06 mmol, 93%). ES/MS (m/z): 134 (M+H).

The following compounds are prepared in essentially the same manner as the method of Preparation 33 using the appropriate intermediate.

TABLE 6

| Prep. No. | Chemical Name | Structure | ES/MS (m/z) (M + H) |
|---|---|---|---|
| 34 | (R)-4-((S)-1-Methoxyethyl)oxazolidin-2-one | 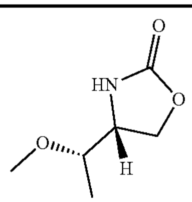 | 146 |
| 35 | (R)-4-((R)-1-Methoxyethyl)oxazolidin-2-one | 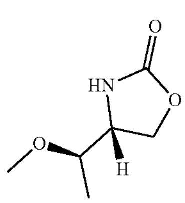 | 146 |

TABLE 6-continued

| Prep. No. | Chemical Name | Structure | ES/MS (m/z) (M + H) |
|---|---|---|---|
| 36 | (R)-4-((S)-1-Fluoroethyl)oxazolidin-2-one | 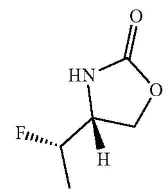 | 134 |

PREPARATION 37

(R)-4-((R)-1-(tert-Butoxy)ethyl)oxazolidin-2-one

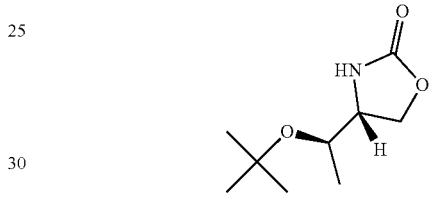

Sodium hydride (822 mg, 20.6 mmol, 60% in mineral oil) is added at 0° C. to a solution of benzyl N-[(1R,2R)-2-tert-butoxy-1-(hydroxymethyl)propyl]carbamate (4.35 g, 13.7 mmol) in THF (70 mL). After stirring for 1 hour at 0° C., the reaction mixture is allowed to warm to room temperature overnight. The mixture is quenched with saturated aqueous NH₄Cl, extracted with EtOAc (2×), dried (Na₂SO₄), filtered, and concentrated. The material is purified with silica gel chromatography eluting with a gradient of 30-70% EtOAc/hexanes to give the title compound as a colorless oil that solidifies to a white solid on standing (1.95 g, 9.35 mmol, 90% purity). ES/MS (m/z): 188 (M+H).

PREPARATION 38

(R)-3-(4-Methoxybenzyl)-4-((S)-1-methoxyethyl)oxazolidin-2-one

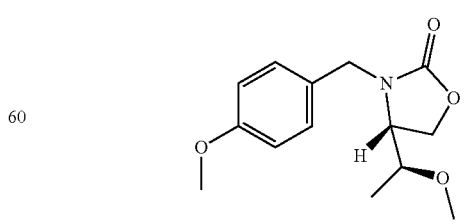

Sodium hydride (300 mg, 7.5 mmol, 60% in mineral oil) is added at 0° C. to a solution of (4R)-4-[(1S)-1-hydroxyethyl]-3-[(4-methoxyphenyl)methyl]oxazolidin-2-one (985 mg, 3.92 mmol) in DMF (20 mL). After 30 minutes, CH₃I (0.732 mL, 11.75 mmol) is added. After another 30 minutes additional sodium hydride is added (100 mg, 2.5 mmol, 60% in mineral oil) and the reaction is allowed to stir for 45 minutes, then quenched with saturated aqueous NH₄Cl, water is added, and the reaction mixture is extracted with EtOAc (3×). The combined organic extracts are dried (Na₂SO₄), filtered, and concentrated to give a residue which is purified with silica gel chromatography eluting with a gradient of 25-60% EtOAc/hexane to give the title compound as a colorless oil (423 mg, 1.59 mmol, 41%). ES/MS (m/z): 266 (M+H).

The following compound is prepared in essentially the same manner as the method of Preparation 38 using the appropriate intermediate.

TABLE 7

| Prep. No. | Chemical Name | Structure | ES/MS (m/z) (M + H) |
|---|---|---|---|
| 39 | (R)-3-(4-Methoxybenzyl)-4-((R)-1-methoxyethyl)oxazolidin-2-one | 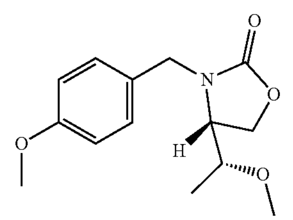 [SMILES: COc1ccc(CN2C(=O)OC[C@@H]2[C@@H](C)OC)cc1] | 266 |

PREPARATION 40 tert-Butyl 4-(4-((S)-1-((4-((S)-4-isopropyl-2-oxooxazolidin-3-yl)pyrimidin-2-yl)amino)ethyl)benzyl)piperazine-1-carboxylate

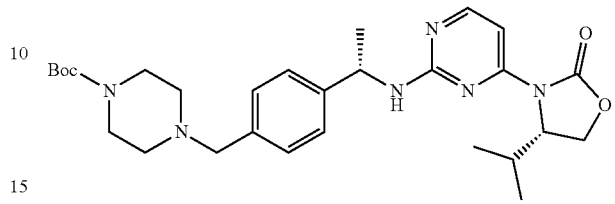

Cesium fluoride (9.35 g, 61.6 mmol) is added to a solution of (S)-3-(2-chloropyrimidin-4-yl)-4-isopropyloxazolidin-2-one (7.44 g, 30.8 mmol) [PCT Int. Appl. (2013), WO 2013046136] in DMSO (50 mL) at room temperature. DIPEA (8.05 mL, 46.2 mmol) is then added. The resulting mixture is added to a solution of tert-butyl 4-[[4-[(1S)-1-aminoethyl]phenyl]methyl]piperazine-1-carboxylate (10.0 g, 31.4 mmol) in DMSO (50 mL). This reaction mixture is heated at 60° C. for 6 hours, 70° C. for 17.5 hours, and 90° C. for 1.5 hours. The reaction mixture is cooled, diluted with aqueous NaCl (50% saturated), and extracted with EtOAc (3×). The organic extracts are combined, washed with brine, dried (MgSO₄), filtered, and concentrated to give a residue which is purified by silica gel chromatography (35-95% EtOAc/hexanes) to give the title compound (10.72 g, 20.4 mmol, 66%). ES/MS (m/z): 525 (M+H).

The following compounds are prepared in essentially the same manner as the method of Preparation 40 using the appropriate intermediates.

TABLE 8

| Prep. No. | Chemical Name | Structure | ES/MS (m/z) (M + H) |
|---|---|---|---|
| 41 | tert-Butyl 4-(4-((S)-1-((4-((S)-4-ethyl-2-oxooxazolidin-3-yl)pyrimidin-2-yl)amino)ethyl)benzyl)piperazine-1-carboxylate | 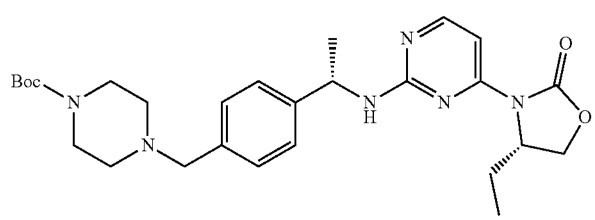 [SMILES: CC[C@H]1COC(=O)N1c1ccnc(N[C@@H](C)c2ccc(CN3CCN(C(=O)OC(C)(C)C)CC3)cc2)n1] | 511 |
| 42 | tert-Butyl 4-(4-((S)-1-((4-((S)-4-methyl-2-oxooxazolidin-3-yl)pyrimidin-2-yl)amino)ethyl)benzyl)piperazine-1-carboxylate | 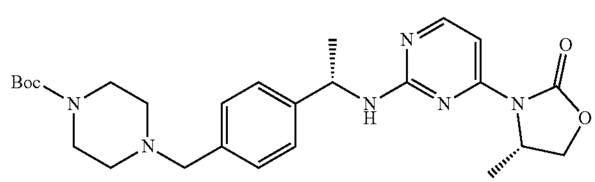 [SMILES: C[C@H](Nc1nccc(N2C(=O)OC[C@@H]2C)n1)c1ccc(CN2CCN(C(=O)OC(C)(C)C)CC2)cc1] | 497 |
| 43 | tert-Butyl (S)-4-(4-(1-((4-(4,4-dimethyl-2-oxooxazolidin-3-yl)pyrimidin-2-yl)amino)ethyl)benzyl)piperazine-1-carboxylate | 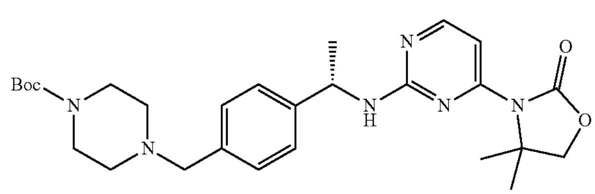 [SMILES: C[C@H](Nc1nccc(N2C(=O)OCC2(C)C)n1)c1ccc(CN2CCN(C(=O)OC(C)(C)C)CC2)cc1] | 511 |

TABLE 8-continued

| Prep. No. | Chemical Name | Structure | ES/MS (m/z) (M + H) |
|---|---|---|---|
| 44 | tert-Butyl 4-(4-((S)-1-((5-fluoro-4-((S)-4-isopropyl-2-oxooxazolidin-3-yl)pyrimidin-2-yl)amino)ethyl)benzyl)piperazine-1-carboxylate | 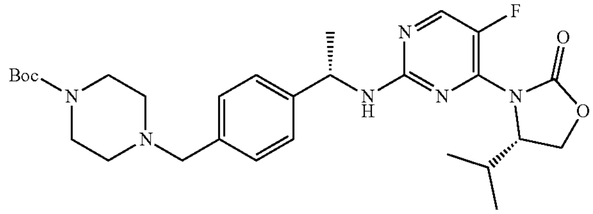 [SMILES: CC(C)[C@H]1COC(=O)N1c1nc(N[C@@H](C)c2ccc(CN3CCN(C(=O)OC(C)(C)C)CC3)cc2)ncc1F] | 543 |
| 45 | tert-Butyl 4-(4-((S)-1-((4-((R)-4-(fluoromethyl)-2-oxooxazolidin-3-yl)pyrimidin-2-yl)amino)ethyl)benzyl)piperazine-1-carboxylate | 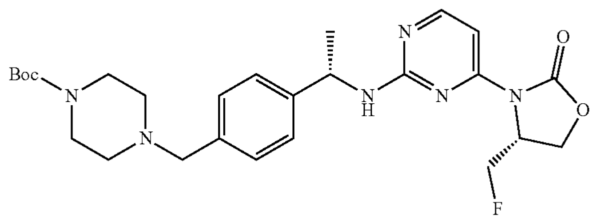 [SMILES: C[C@H](Nc1nccc(N2C(=O)OC[C@@H]2CF)n1)c1ccc(CN2CCN(C(=O)OC(C)(C)C)CC2)cc1] | 515 |
| 46 | tert-Butyl (S)-4-(4-(1-((4-(4,4-dimethyl-2-oxooxazolidin-3-yl)-5-fluoropyrimidin-2-yl)amino)ethyl)benzyl)piperazine-1-carboxylate | 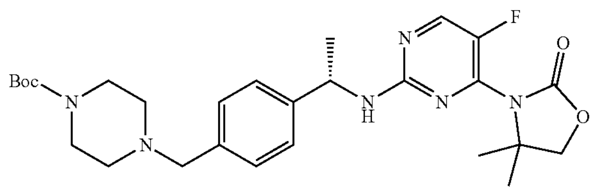 [SMILES: C[C@H](Nc1ncc(F)c(N2C(=O)OCC2(C)C)n1)c1ccc(CN2CCN(C(=O)OC(C)(C)C)CC2)cc1] | 529 |
| 47 | tert-Butyl 4-(4-(1-((4-((S)-4-ethyl-2-oxooxazolidin-3-yl)pyrimidin-2-yl)amino)-2-fluoroethyl)benzyl)piperazine-1-carboxylate | 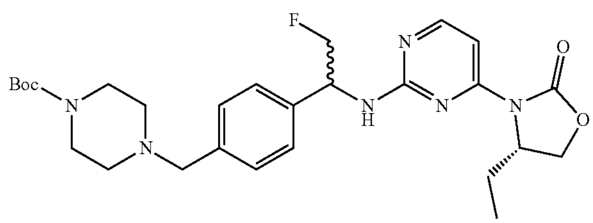 [SMILES: CC[C@H]1COC(=O)N1c1ccnc(NC(CF)c2ccc(CN3CCN(C(=O)OC(C)(C)C)CC3)cc2)n1] | 529 |
| 48 | tert-Butyl 4-(4-(1-((4-(4,4-dimethyl-2-oxooxazolidin-3-yl)pyrimidin-2-yl)amino)-2-fluoroethyl)benzyl)piperazine-1-carboxylate | 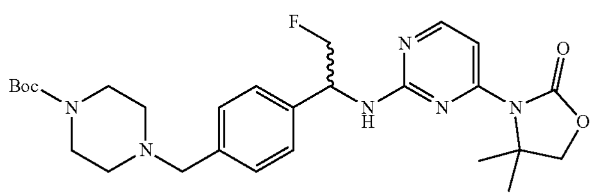 [SMILES: CC(C)(C)OC(=O)N1CCN(Cc2ccc(C(CF)Nc3nccc(N4C(=O)OCC4(C)C)n3)cc2)CC1] | 529 |
| 49 | tert-Butyl 4-(1-(4-((S)-1-((4-(2-oxooxazolidin-3-yl)pyrimidin-2-yl)amino)ethyl)phenyl)propyl)piperazine-1-carboxylate | 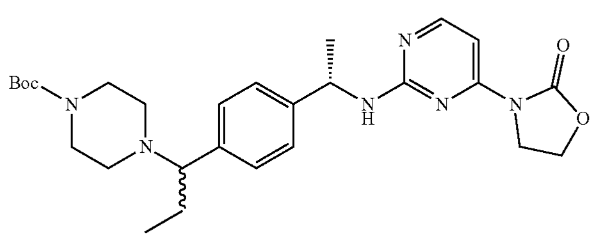 [SMILES: CCC(c1ccc([C@H](C)Nc2nccc(N3CCOC3=O)n2)cc1)N1CCN(C(=O)OC(C)(C)C)CC1] | 511 |

PREPARATION 50 tert-Butyl 4-[1-[4-[(1S)-1-[[4-[(4R)-4-[(1R)-1-tert-butoxyethyl]-2-oxo-oxazolidin-3-yl]pyrimidin-2-yl]amino]ethyl]phenyl]-2-cyclopropyl-ethyl]piperazine-1-carboxylate

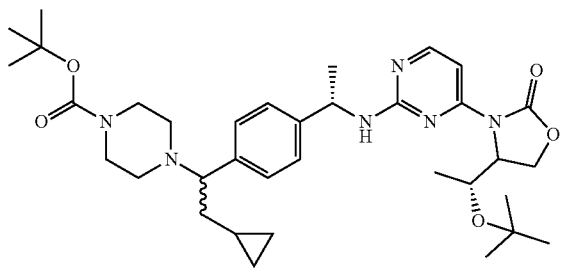 [SMILES: C[C@H](Nc1nccc(N2C(=O)OCC2[C@@H](C)OC(C)(C)C)n1)c1ccc(C(CC2CC2)N2CCN(C(=O)OC(C)(C)C)CC2)cc1]

A mixture of tert-butyl 4-[1-[4-[(1S)-1-aminoethyl]phenyl]-2-cyclopropyl-ethyl]piperazine-1-carboxylate (350 mg, 0.91 mmol), (4R)-4-[(1R)-1-tert-butoxyethyl]-3-(2-chloro-pyrimidin-4-yl)oxazolidin-2-one (273 mg, 0.91 mmol), cesium fluoride (152 mg, 1.00 mmol) and DiPEA (0.17 mL, 1.00 mmol) in DMSO (3.0 mL) is heated in a sealed vial to about 85° C. After about 6 hours, the mixture is cooled to room temperature and partitioned between Et$_2$O and water. The organic layer is washed with saturated aqueous sodium NaCl and concentrated. The crude material is purified with silica gel chromatography eluting with a gradient of 20% to 50% EtOAc in hexanes to give the title compound as an oil (288 mg, 0.448 mmol, 49%). ES/MS (m/z): 637.4 (M+H).

PREPARATION 51 tert-Butyl 4-[2-cyclopropyl-1-[4-[(1S)-1-[[4-[(4S)-4-isopropyl-2-oxo-oxazolidin-3-yl]pyrimidin-2-yl]amino]ethyl]phenyl]ethyl]piperazine-1-carboxylate, Isomer 1

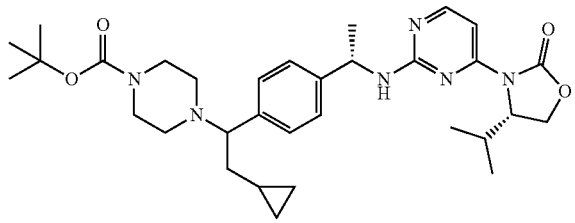 [SMILES: CC(C)[C@H]1COC(=O)N1c1ccnc(N[C@@H](C)c2ccc(C(CC3CC3)N3CCN(C(=O)OC(C)(C)C)CC3)cc2)n1]

A mixture of tert-butyl 4-[1-[4-[(1S)-1-aminoethyl]phenyl]-2-cyclopropyl-ethyl]piperazine-1-carboxylate, isomer 1 (1.3 g, 3.48 mmol), (4S)-3-(2-chloropyrimidin-4-yl)-4-isopropyl-oxazolidin-2-one (1.09 g, 4.51 mmol), cesium fluoride (1.59 g, 10.5 mmol) and DiPEA (0.911 mL, 5.22 mmol) in DMSO (17 mL) is placed in a pre-heated block at 70° C. and stirred for 2 hours. The reaction mixture is cooled to room temperature, diluted with EtOAc, and washed with 3×water. The combined aqueous layers are re-extracted with 2×EtOAc. The organic extracts are combined, dried over Na$_2$SO$_4$, filtered, and the solvent removed in vacuo to give the crude product. The product is purified via silica gel flash chromatography using a gradient of 30 to 60% EtOAc in hexanes to give the title compound (1.97 g, 93%) as a white amorphous solid. ES/MS m/z 579 (M+H).

The following compound is prepared in essentially the same manner as the method of Preparation 51

TABLE 9

| Prep. No. | Chemical Name | Structure | ES/MS (m/z) (M + H) |
|---|---|---|---|
| 52 | tert-Butyl 4-[2-cyclopropyl-1-[4-[(1S)-1-[[4-[(4S)-4-isopropyl-2-oxo-oxazolidin-3-yl]pyrimidin-2-yl]amino]ethyl]phenyl]ethyl]piperazine-1-carboxylate, isomer 2 | 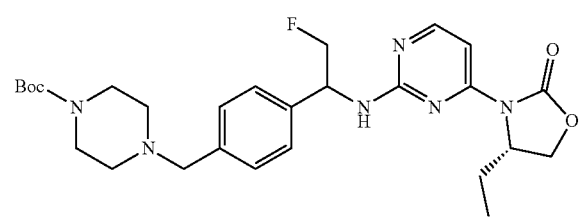 [SMILES: CC[C@H]1COC(=O)N1c1ccnc(NC(CF)c2ccc(CN3CCN(C(=O)OC(C)(C)C)CC3)cc2)n1] | 579 |

PREPARATION 53 tert-Butyl 4-(4-1-((4-((S)-4-ethyl-2-oxooxazolidin-3-yl)pyrimidin-2-yl)amino)-2-fluoroethyl)benzyl)piperazine-1-carboxylate, isomer 2 tert-Butyl 4-(4-(1-((4-((S)-4-ethyl-2-oxooxazolidin-3-yl)pyrimidin-2-yl)amino)-2-fluoroethyl)benzyl)piperazine-1-carboxylate (540 mg, 1.0 mmol) is dissolved in MeOH (4 mL) and resolved by chiral SFC chromatography using the following conditions: column: Chiralpak AS-H, 21.2×150 mm); injection volume: 0.9 mL×5, eluent: 15% IPA (0.2% IPAm)/CO$_2$, detection wavelength: 225 nm; elution time: 10 min; flow rate: 70 g/min; column temperature: 40° C.; BPR Setpoint: 100 bar; BPR temperature: 35° C. The title compound is isolated as the second eluting peak (isomer 2) as a white solid (260 mg, 0.48 mmol, 48%, R$_t$=3.04, >99% ee). ES/MS (m/z): 529 (M+H).

The following compounds are prepared in essentially the same manner as the method of Preparation 53.

TABLE 10

| Prep. No. | Chemical Name | Structure | ES/MS (m/z) (M + H) |
|---|---|---|---|
| 54 | tert-Butyl-4-(4-(1-((4-(4,4-dimethyl-2-oxooxazolidin-3-yl)pyrimidin-2-yl)amino)-2-fluoroethyl)benzyl)piperazine-1-carboxylate, isomer 2 | 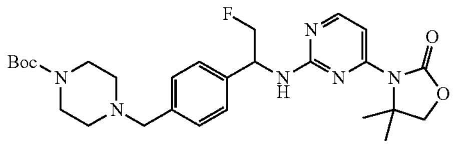 [SMILES: CC(C)(C)OC(=O)N1CCN(Cc2ccc(C(CF)Nc3nccc(N4C(=O)OCC4(C)C)n3)cc2)CC1] | 529 |
| 55 | tert-Butyl 4-(1-(4-((S)-1-((4-(2-oxooxazolidin-3-yl)pyrimidin-2-yl)amino)ethyl)phenyl)propyl)piperazine-1-carboxylate, isomer 1 | 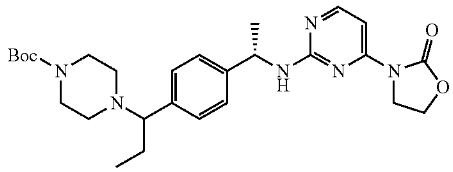 [SMILES: CCC(c1ccc([C@H](C)Nc2nccc(N3CCOC3=O)n2)cc1)N1CCN(C(=O)OC(C)(C)C)CC1] | 511 |
| 56 | tert-Butyl 4-(1-(4-((S)-1-((4-(2-oxooxazolidin-3-yl)pyrimidin-2-yl)amino)ethyl)phenyl)propyl)piperazine-1-carboxylate, isomer 2 | 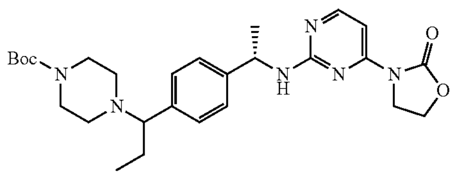 [SMILES: CCC(c1ccc([C@H](C)Nc2nccc(N3CCOC3=O)n2)cc1)N1CCN(C(=O)OC(C)(C)C)CC1] | 511 |

PREPARATION 57 tert-Butyl (S)-4-(4-(1-((4,6-difluoropyrimidin-2-yl)amino)ethyl)benzyl)piperazine-1-carboxylate

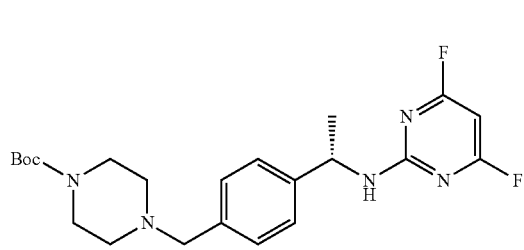 [SMILES: C[C@H](Nc1nc(F)cc(F)n1)c1ccc(CN2CCN(C(=O)OC(C)(C)C)CC2)cc1]

A solution of 2,4,6-trifluoropyrimidine (278 mg, 2.07 mmol) in Et$_2$O (10 mL) is cooled to −20° C. and is treated, dropwise, with a solution of tert-butyl 4-[[4-[(1S)-1-aminoethyl]phenyl]methyl]piperazine-1-carboxylate (600 mg, 1.88 mmol) in Et$_2$O (10 mL). The resulting mixture is stirred at −20° C. for 1 hour and is then allowed to warm to room temperature and is stirred overnight. The solids are removed by filtration and are washed with additional Et$_2$O. The filtrate is washed with water, using a small portion of NaCl additive to reduce emulsification, and the aqueous layer is back-extracted with Et$_2$O (1×) and CH$_2$Cl$_2$ (1×). The combined organic extracts are then dried (Na$_2$SO$_4$), filtered, and concentrated to give a crude product that is purified by silica gel chromatography eluting with 20-60% EtOAc/hexanes to give the title compound as a pale yellow oil (606 mg, 1.40 mmol, 74%). ES/MS (m/z): 434 (M+H).

PREPARATION 58 tert-Butyl 4-(2-cyclopropyl-1-(4-((S)-1-((4,6-difluoropyrimidin-2-yl)amino)ethyl)phenyl)ethyl)piperazine-1-carboxylate, Isomer 1

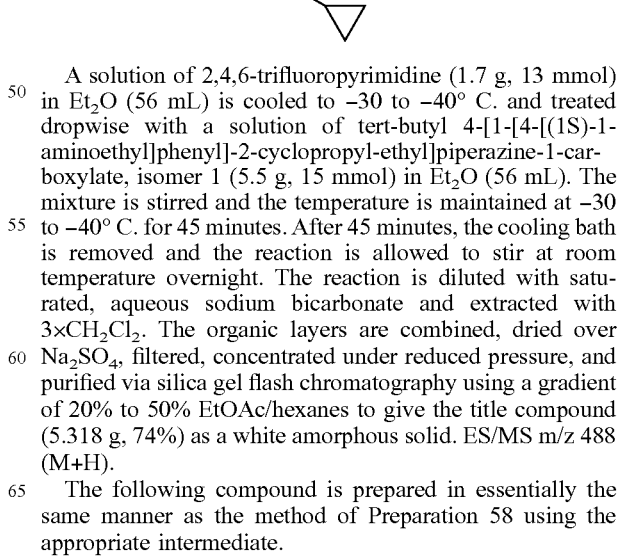

A solution of 2,4,6-trifluoropyrimidine (1.7 g, 13 mmol) in Et$_2$O (56 mL) is cooled to −30 to −40° C. and treated dropwise with a solution of tert-butyl 4-[1-[4-[(1S)-1-aminoethyl]phenyl]-2-cyclopropyl-ethyl]piperazine-1-carboxylate, isomer 1 (5.5 g, 15 mmol) in Et$_2$O (56 mL). The mixture is stirred and the temperature is maintained at −30 to −40° C. for 45 minutes. After 45 minutes, the cooling bath is removed and the reaction is allowed to stir at room temperature overnight. The reaction is diluted with saturated, aqueous sodium bicarbonate and extracted with 3×CH$_2$Cl$_2$. The organic layers are combined, dried over Na$_2$SO$_4$, filtered, concentrated under reduced pressure, and purified via silica gel flash chromatography using a gradient of 20% to 50% EtOAc/hexanes to give the title compound (5.318 g, 74%) as a white amorphous solid. ES/MS m/z 488 (M+H).

The following compound is prepared in essentially the same manner as the method of Preparation 58 using the appropriate intermediate.

TABLE 11

| Prep. No. | Chemical Name | Structure | ES/MS (m/z) (M + H) |
|---|---|---|---|
| 59 | tert-butyl 4-(2-cyclopropyl-1-(4-((S)-1-((4,6-difluoropyrimidin-2-yl)amino)ethyl)phenyl)ethyl)piperazine-1-carboxylate, isomer 2 | 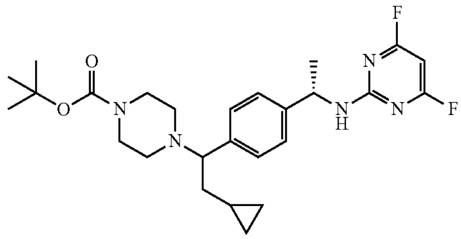 [SMILES: C[C@H](Nc1nc(F)cc(F)n1)c1ccc(C(CC2CC2)N2CCN(C(=O)OC(C)(C)C)CC2)cc1] | 488 |
| 59a | tert-Butyl 4-[1-[4-[(1S)-1-[(4,6-difluoropyrimidin-2-yl)amino]ethyl]phenyl]propyl]piperazine-1-carboxylate, isomer 1 | 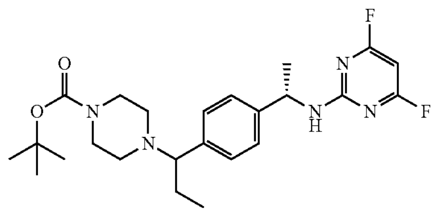 [SMILES: CCC(c1ccc([C@H](C)Nc2nc(F)cc(F)n2)cc1)N1CCN(C(=O)OC(C)(C)C)CC1] | 462 |
| 59b | tert-Butyl 4-[1-[4-[(1S)-1-[(4,6-difluoropyrimidin-2-yl)amino]ethyl]phenyl]propyl]piperazine-1-carboxylate, isomer 2 | 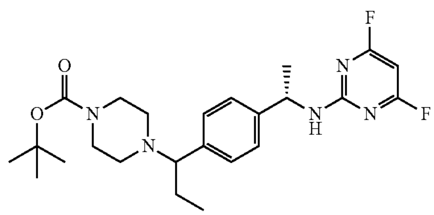 [SMILES: CCC(c1ccc([C@H](C)Nc2nc(F)cc(F)n2)cc1)N1CCN(C(=O)OC(C)(C)C)CC1] | 462 |

PREPARATION 60 tert-Butyl 4-(4-((S)-1-((4-fluoro-6-((S)-4-isopropyl-2-oxooxazolidin-3-yl)pyrimidin-2-yl)amino)ethyl)benzyl)piperazine-1-carboxylate

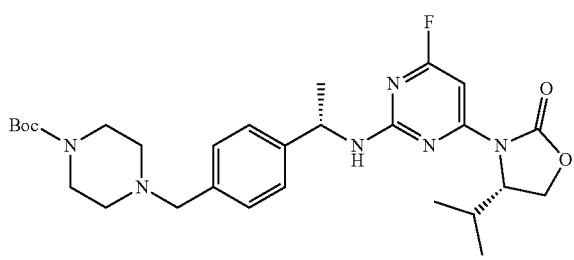 [SMILES: CC(C)[C@H]1COC(=O)N1c1cc(F)nc(N[C@@H](C)c2ccc(CN3CCN(C(=O)OC(C)(C)C)CC3)cc2)n1]

Sodium hydride (61 mg, 1.53 mmol, 60% in mineral oil) is added to a solution of tert-butyl (S)-4-(4-(1-((4,6-difluoropyrimidin-2-yl)amino)ethyl)benzyl)piperazine-1-carboxylate (550 mg, 1.27 mmol) in DMF at (6 mL) 0° C. After 1 minute, (S)-4-isopropyloxazolidin-2-one (180 mg, 1.39 mmol) is added and the mixture is stirred for 1 hour at 0° C. followed by warming to room temperature and stirring overnight. The reaction mixture is then quenched with water and is extracted with EtOAc. The EtOAc extract is washed with 5% aqueous LiCl (2×), dried (Na$_2$SO$_4$), filtered, and concentrated to give a residue which is purified by silica gel chromatography eluting with a gradient of 30-50% EtOAc/hexanes to give the title compound a solid (500 mg, 0.92 mmol, 73%). ES/MS (m/z): 543 (M+H).

The following compounds are prepared in essentially the same manner to the method of Preparation 60 using the appropriate intermediates.

TABLE 12

| Prep. No. | Chemical Name | Structure | ES/MS (m/z) (M + H) |
|---|---|---|---|
| 61 | terf-Butyl (S)-4-(4-(1-((4-(4,4-dimethyl-2-oxooxazolidin-3-yl)-6-fluoropyrimidin-2-yl)amino)ethyl)benzyl)piperazine-1-carboxylate | 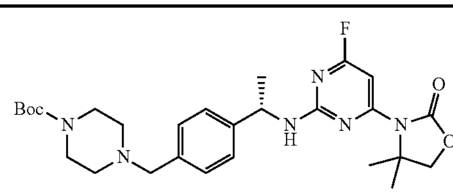 | 529 |

TABLE 12-continued

| Prep. No. | Chemical Name | Structure | ES/MS (m/z) (M + H) |
|---|---|---|---|
| 62 | tert-Butyl 4-(4-((S)-1-((4-fluoro-6-((R)-4-((R)-1-methoxyethyl)-2-oxooxazolidin-3-yl)pyrimidin-2-yl)amino)ethyl)benzyl)piperazine-1-carboxylate | 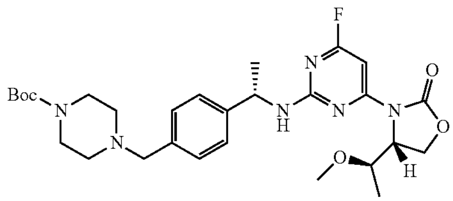 [SMILES: CO[C@H](C)[C@H]1COC(=O)N1c1cc(F)nc(N[C@@H](C)c2ccc(CN3CCN(C(=O)OC(C)(C)C)CC3)cc2)n1] | 559 |
| 63 | tert-Butyl 4-(4-((S)-1-((4-fluoro-6-((R)-4-((S)-1-fluoroethyl)-2-oxooxazolidin-3-yl)pyrimidin-2-yl)amino)ethyl)benzyl)piperazine-1-carboxylate | 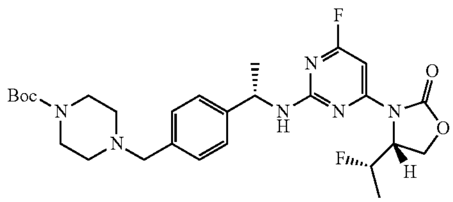 [SMILES: C[C@H](Nc1nc(F)cc(N2C(=O)OC[C@@H]2[C@H](C)F)n1)c1ccc(CN2CCN(C(=O)OC(C)(C)C)CC2)cc1] | 547 |

PREPARATION 64 tert-Butyl 4-[2-cyclopropyl-1-[4-[(1S)-1-[[4-(4,4-dimethyl-2-oxo-oxazolidin-3-yl)-6-fluoro-pyrimidin-2-yl]amino]ethyl]phenyl]ethyl]piperazine-1-carboxylate, Isomer 1

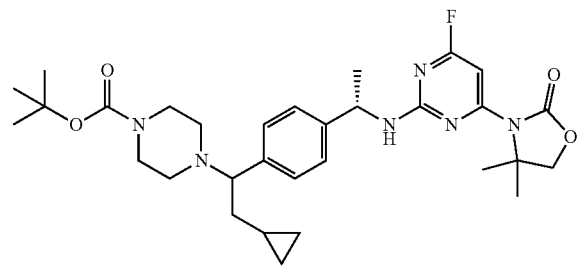 [SMILES: C[C@H](Nc1nc(F)cc(N2C(=O)OCC2(C)C)n1)c1ccc(C(CC2CC2)N2CCN(C(=O)OC(C)(C)C)CC2)cc1]

A solution of 4,4-dimethyloxazolidin-2-one (493 mg, 4.282 mmol) in DMF (20 mL) is cooled to 0° C., treated with sodium hydride (187 mg, 4.67541 mmol), and stirred for about 40 minutes. A solution of tert-butyl 4-[2-cyclopropyl-1-[4-[(1S)-1-[(4,6-difluoropyrimidin-2-yl)amino]ethyl]phenyl]ethyl]piperazine-1-carboxylate, isomer 1 (1.90 g, 3.90 mmol) in DMF (10 mL) is added and the mixture is allowed to warm to room temperature as the cooling bath expires overnight. When the reaction is complete, the reaction is quenched with saturated, aqueous ammonium chloride and extracted with EtOAc. The organic extract is washed with 5% aqueous LiCl, collected, dried over $Na_2SO_4$, filtered, concentrated under reduced pressure, and purified by silica gel flash chromatography using a gradient of 20% to 40% EtOAc/hexanes to give the title product (1.12 g, 48%) as a white amorphous solid. ES/MS m/z 583 (M+H).

The following compound is prepared in essentially the same manner as the method of Preparation 64 using the appropriate intermediate.

TABLE 13

| Prep. No. | Chemical Name | Structure | ES/MS (m/z) (M + H) |
|---|---|---|---|
| 65 | tert-Butyl 4-[2-cyclopropyl-1-[4-[(1S)-1-[[4-(4,4-dimethyl-2-oxo-oxazolidin-3-yl)-6-fluoro-pyrimidin-2-yl]amino]ethyl]phenyl]ethyl]piperazine-1-carboxylate, isomer 2 | 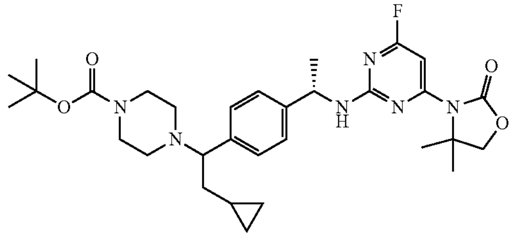 [SMILES: C[C@H](Nc1nc(F)cc(N2C(=O)OCC2(C)C)n1)c1ccc(C(CC2CC2)N2CCN(C(=O)OC(C)(C)C)CC2)cc1] | 583 |

TABLE 13-continued

| Prep. No. | Chemical Name | Structure | ES/MS (m/z) (M + H) |
|---|---|---|---|
| 65a | tert-butyl 4-[1-[4-[(1S)-1-[[4-(4,4-dimethyl-2-oxo-oxazolidin-3-yl)-6-fluoro-pyrimidin-2-yl]amino]ethyl]phenyl]propyl]piperazine-1-carboxylate, isomer 1 | 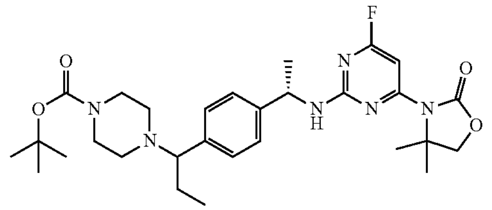 [SMILES: CCC(c1ccc([C@H](C)Nc2nc(F)cc(N3C(=O)OCC3(C)C)n2)cc1)N1CCN(C(=O)OC(C)(C)C)CC1] | 557 |
| 65b | tert-butyl 4-[1-[4-[(1S)-1-[[4-(4,4-dimethyl-2-oxo-oxazolidin-3-yl)-6-fluoro-pyrimidin-2-yl]amino]ethyl]phenyl]propyl]piperazine-1-carboxylate, isomer 2 | 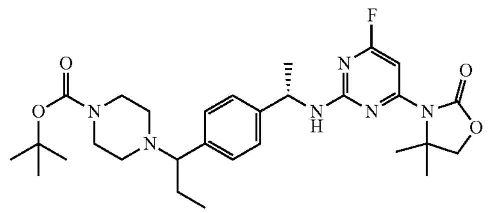 [SMILES: CCC(c1ccc([C@H](C)Nc2nc(F)cc(N3C(=O)OCC3(C)C)n2)cc1)N1CCN(C(=O)OC(C)(C)C)CC1] | 557 |

PREPARATION 66 tert-Butyl (S)-4-(4-(1-((6-oxo-1,6-dihydropyrimidin-2-yl)amino)ethyl)benzyl)piperazine-1-carboxylate

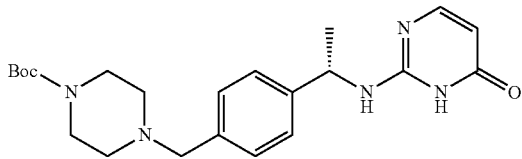 [SMILES: C[C@H](Nc1nccc(=O)[nH]1)c1ccc(CN2CCN(C(=O)OC(C)(C)C)CC2)cc1]

2-Methylsulfanyl-1H-pyrimidin-6-one (4.81 g, 33.8 mmol), tert-butyl 4-[[4-[(1S)-1-aminoethyl]phenyl]methyl]piperazine-1-carboxylate (9.00 g, 28.2 mmol), and DME (56 mL) are split equally into three microwave vessels that are sealed and heated to 120° C. for 4 days. The reaction mixtures are allowed to cool to room temperature, combined, concentrated, and resuspended in CH₂Cl₂. The solids are filtered away and the filtrate is adsorbed onto silica gel and chromatographed on silica gel eluting with a gradient of 1-7% MeOH/CH₂Cl₂ to give the title compound as an off-white solid (10.55 g, 22.45 mmol, 88% purity). ES/MS (m/z): 414 (M+H).

PREPARATION 67 tert-Butyl (S)-4-(4-(1-((4-chloropyrimidin-2-yl)amino)ethyl)benzyl)piperazine-1-carboxylate

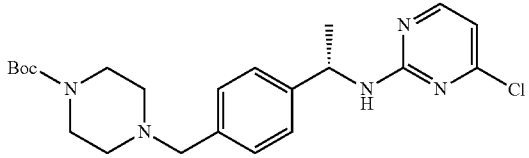 [SMILES: C[C@H](Nc1nccc(Cl)n1)c1ccc(CN2CCN(C(=O)OC(C)(C)C)CC2)cc1]

A mixture of tert-butyl (S)-4-(4-(1-((6-oxo-1,6-dihydropyrimidin-2-yl)amino)ethyl)benzyl)piperazine-1-carboxylate (10.55 g, 22.45 mmol, 88% purity), carbon tetrachloride (6.5 mL), triphenylphosphine resin (22.5 g, 67 mmol, 3 mmol phosphine/g), and 1,2-DCE (300 mL) is stirred at 70° C. for 6 hours and then cooled to room temperature. MeOH (300 mL) is added and the resulting mixture is stirred vigorously for 30 minutes. The resin is removed from the mixture by filtration and is rinsed with additional MeOH that is added to the filtrate. The combined filtrates are concentrated and the residue is dissolved in CH₂Cl₂ and washed with saturated aqueous NaHCO₃. The aqueous phase is back extracted with CH₂Cl₂ (2×). The combined organic extracts are dried (Na₂SO₄), filtered, and concentrated to give a residue which is purified by silica gel chromatography eluting with a gradient of 35-60% EtOAc/hexanes to give the title compound as a white amorphous solid (6.85 g, 15.9 mmol, 71%). ES/MS (m/z): 432 (M+H).

PREPARATION 68 tert-Butyl 4-(4-((S)-1-((4-((R)-4-((R)-1-fluoroethyl)-2-oxooxazolidin-3-yl)pyrimidin-2-yl)amino)ethyl)benzyl)piperazine-1-carboxylate

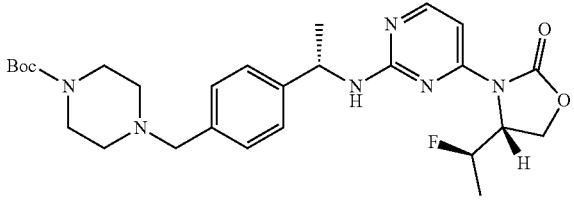 [SMILES: C[C@H](Nc1nccc(N2C(=O)OC[C@@H]2[C@@H](C)F)n1)c1ccc(CN2CCN(C(=O)OC(C)(C)C)CC2)cc1]

A solution of tert-butyl (S)-4-(4-(1-((4-chloropyrimidin-2-yl)amino)ethyl)benzyl)piperazine-1-carboxylate (400 mg, 0.925 mmol), (R)-4-((R)-1-fluoroethyl)oxazolidin-2-one (136 mg, 1.02 mmol), and Cs₂CO₃ (513 mg, 1.57 mmol) in 1,4-dioxane (4.5 mL) is degassed by bubbling N₂ gas through it for 5-10 minutes. Tris(dibenzylideneacetone)dipalladium (51 mg, 0.056 mmol) and 4,5-bis(diphenylphosphino)-9,9-dimethylxanthene (113 mg, 0.195 mmol) are then added and degassing is repeated. The vessel is sealed and heated at 100° C. for 4.5 hours. The mixture is cooled to room temperature, diluted with EtOAc, and filtered over diatomaceous earth. The filtrate is washed with water and the water is extracted with additional EtOAc. The combined organic extracts are dried (Na₂SO₄), filtered, and concentrated. The residue is purified with silica gel chromatography eluting with a gradient of 70-100% EtOAc/hexanes to give the title compound as a pale yellow amorphous solid (421 mg, 0.796 mmol, 86%). ES/MS (m/z): 529 (M+H).

The following compounds are prepared in essentially the same manner as the method of Preparation 68 using the appropriate intermediates.

TABLE 14

| Prep. No. | Chemical Name | Structure | ES/MS (m/z) (M + H) |
|---|---|---|---|
| 69 | tert-Butyl 4-(4-((S)-1-((4-((R)-4-((R)-1-(tert-butoxy)ethyl)-2-oxooxazolidin-3-yl)pyrimidin-2-yl)amino)ethyl)benzyl)piperazine-1-carboxylate | 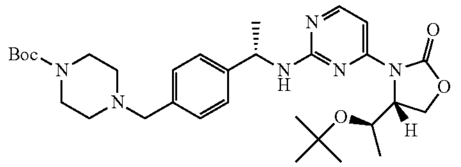 [SMILES: C[C@H](Nc1nccc(N2C(=O)OC[C@@H]2[C@@H](C)OC(C)(C)C)n1)c1ccc(CN2CCN(C(=O)OC(C)(C)C)CC2)cc1] | 583 |
| 70 | tert-Butyl 4-(4-((S)-1-((4-((R)-4-((S)-1-methoxyethyl)-2-oxooxazolidin-3-yl)pyrimidin-2-yl)amino)ethyl)benzyl)piperazine-1-carboxylate | 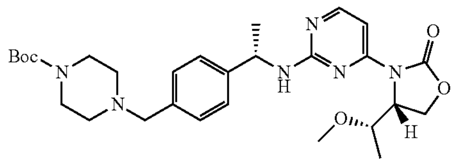 [SMILES: CO[C@@H](C)[C@H]1COC(=O)N1c1ccnc(N[C@@H](C)c2ccc(CN3CCN(C(=O)OC(C)(C)C)CC3)cc2)n1] | 541 |
| 71 | tert-Butyl 4-(4-((S)-1-((4-((R)-4-((R)-1-methoxyethyl)-2-oxooxazolidin-3-yl)pyrimidin-2-yl)amino)ethyl)benzyl)piperazine-1-carboxylate | 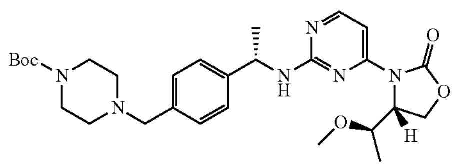 [SMILES: CO[C@H](C)[C@H]1COC(=O)N1c1ccnc(N[C@@H](C)c2ccc(CN3CCN(C(=O)OC(C)(C)C)CC3)cc2)n1] | 541 |

PREPARATION 72 tert-Butyl 4-[1-[4-[(1S)-1-[[4-amino-6-(4,4-dimethyl-2-oxo-oxazolidin-3-yl)pyrimidin-2-yl]amino]ethyl]phenyl]propyl]piperazine-1-carboxylate, Isomer 1

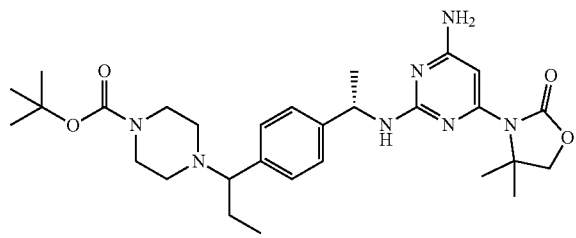 [SMILES: CCC(c1ccc([C@H](C)Nc2nc(N)cc(N3C(=O)OCC3(C)C)n2)cc1)N1CCN(C(=O)OC(C)(C)C)CC1]

A DMSO solution (14 mL) of tert-butyl 4-[1-[4-[(1S)-1-[[4-(4,4-dimethyl-2-oxo-oxazolidin-3-yl)-6-fluoro-pyrimidin-2-yl]amino]ethyl]phenyl]propyl]piperazine-1-carboxylate, isomer 1 (1.62 g, 2.74 mmol) is treated with ammonium hydroxide (72%, 1 mL, 10 eq.) in a pressure vessel and heated to 110° C. overnight. The reaction is allowed to cool to room temperature, diluted with EtOAc, and washed with water (3×). The organic layer is collected dried over MgSO4, filtered, and the solvent removed under reduced pressure giving the title compound as a white amorphous solid (1.51 g, 93%). ES/MS m/z 554 (M+H).

The following compound is prepared in essentially the same manner as the method of Preparation 72 using the appropriate intermediate.

TABLE 15

| Prep. No. | Chemical Name | Structure | ES/MS (m/z) (M + H) |
|---|---|---|---|
| 73 | tert-Butyl 4-[1-[4-[(1S)-1-[[4-amino-6-(4,4-dimethyl)-2-oxooxazolidin-3-yl)pyrimidin-2-yl]amino]ethyl]phenyl]propyl]piperazine-1-carboxylate, isomer 2 | 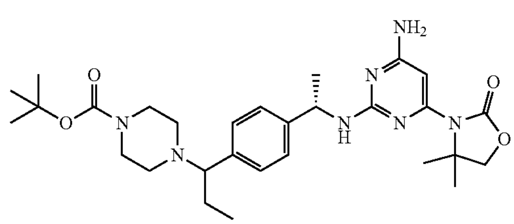 [SMILES: CCC(c1ccc([C@H](C)Nc2nc(N)cc(N3C(=O)OCC3(C)C)n2)cc1)N1CCN(C(=O)OC(C)(C)C)CC1] | 554 |

PREPARATION 74

(S)-4-isopropyl-3-(2-(((S)-1-(4-(piperazin-1-ylmethyl)phenyl)ethyl)amino)pyrimidin-4-yl)oxazolidin-2-one

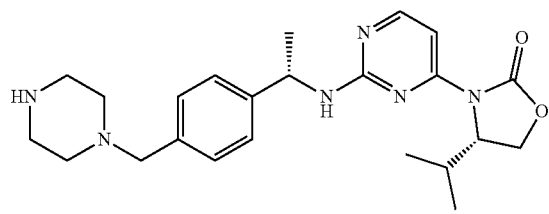 [SMILES: CC(C)[C@H]1COC(=O)N1c1ccnc(N[C@@H](C)c2ccc(CN3CCNCC3)cc2)n1]

TFA (69 mL, 912.6 mmol) is added to a solution of tert-butyl 4-(4-((S)-1-((4-((S)-4-isopropyl-2-oxooxazolidin-3-yl)pyrimidin-2-yl)amino)ethyl)benzyl)piperazine-1-carboxylate (10.7 g, 20.4 mmol) in CH$_2$Cl$_2$ (204 mL) at room temperature. After stirring for 4 hours, the pH of the reaction is adjusted to 9 using saturated aqueous Na$_2$CO$_3$ and the resulting mixture is extracted with CH$_2$Cl$_2$ (3×). The organic extracts are combined, dried (MgSO4), filtered, and concentrated to give a residue which is purified by silica gel chromatography eluting with a gradient of 0-15% 7 N—NH$_3$ in MeOH/EtOAc to give the title compound (7.76 g, 18.3 mmol, 90%). ES/MS (m/z): 425 (M+H).

The following compounds are prepared in essentially the same manner as the method of Preparation 74 using the appropriate intermediate.

TABLE 16

| Prep. No. | Chemical Name | Structure | ES/MS (m/z) (M + H) |
|---|---|---|---|
| 75 | (S)-4,4-Dimethyl-3-(2-((1-(4-(piperazin-1-ylmethyl)phenyl)ethyl)amino)pyrimidin-4-yl)oxazolidin-2-one | 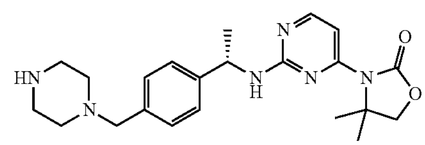 [SMILES: C[C@H](Nc1nccc(N2C(=O)OCC2(C)C)n1)c1ccc(CN2CCNCC2)cc1] | 411 |
| 76 | (S)-3-(5-Fluoro-2-(((S)-1-(4-(piperazin-1-ylmethyl)phenyl)ethyl)amino)pyrimidin-4-yl)-4-isopropyloxazolidin-2-one | 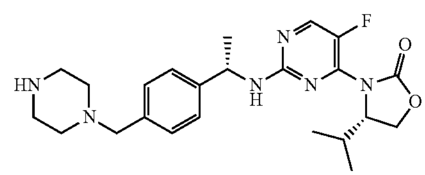 [SMILES: CC(C)[C@H]1COC(=O)N1c1nc(N[C@@H](C)c2ccc(CN3CCNCC3)cc2)ncc1F] | 443 |
| 77 | (S)-3-(6-Fluoro-2-(((S)-1-(4-(piperazin-1-ylmethyl)phenyl)ethyl)amino)pyrimidin-4-yl)-4-isopropyloxazolidin-2-one | 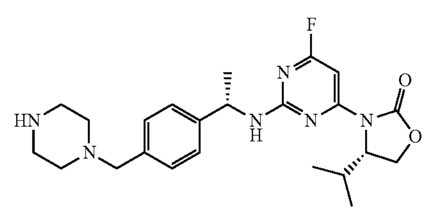 [SMILES: CC(C)[C@H]1COC(=O)N1c1cc(F)nc(N[C@@H](C)c2ccc(CN3CCNCC3)cc2)n1] | 443 |
| 78 | (R)-4-(Fluoromethyl)-3-(2-(((S)-1-(4-(piperazin-1-ylmethyl)phenyl)ethyl)amino)pyrimidin-4-yl)oxazolidin-2-one | 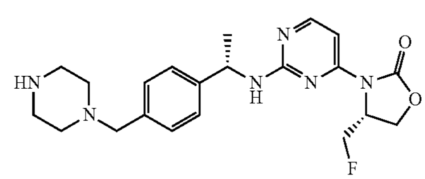 [SMILES: C[C@H](Nc1nccc(N2C(=O)OC[C@@H]2CF)n1)c1ccc(CN2CCNCC2)cc1] | 415 |
| 79 | 3-[5-Fluoro-2-[[(1S)-1-[4-(piperazin-1-ylmethyl)phenyl]ethyl]amino]pyrimidin-4-yl]-4,4-dimethyl-oxazolidin-2-one | 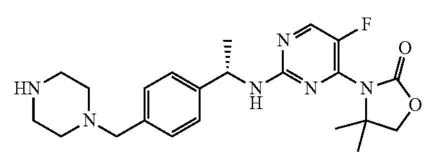 [SMILES: C[C@H](Nc1ncc(F)c(N2C(=O)OCC2(C)C)n1)c1ccc(CN2CCNCC2)cc1] | 429 |
| 80 | (S)-4-Ethyl-3-(2-(((R)-2-fluoro-1-(4-(piperazin-1-ylmethyl)phenyl)ethyl)amino)pyrimidin-4-yl)oxazolidin-2-one | 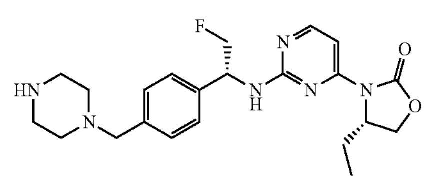 [SMILES: CC[C@H]1COC(=O)N1c1ccnc(N[C@@H](CF)c2ccc(CN3CCNCC3)cc2)n1] | 429 |

TABLE 16-continued

| Prep. No. | Chemical Name | Structure | ES/MS (m/z) (M + H) |
|---|---|---|---|
| 81 | (R)-3-(2-((2-Fluoro-1-(4-(piperazin-1-ylmethyl)phenyl)ethyl)amino)pyrimidin-4-yl)-4,4-dimethyloxazolidin-2-one | 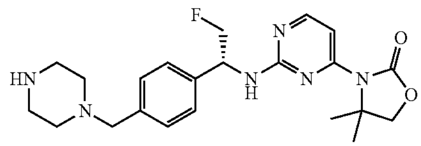 [SMILES: CC1(C)COC(=O)N1c1ccnc(N[C@@H](CF)c2ccc(CN3CCNCC3)cc2)n1] | 429 |
| 82 | (S)-3-(6-Fluoro-2-((1-(4-(piperazin-1-ylmethyl)phenyl)ethyl)amino)pyrimidin-4-yl)-4,4-dimethyloxazolidin-2-one | 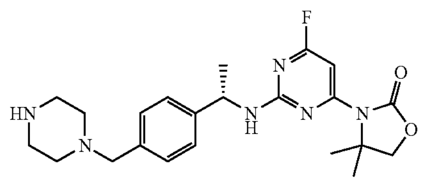 [SMILES: C[C@H](Nc1nc(F)cc(N2C(=O)OCC2(C)C)n1)c1ccc(CN2CCNCC2)cc1] | 429 |
| 83 | (R)-4-((R)-1-Fluoroethyl)-3-(2-(((S)-1-(4-(piperazin-1-ylmethyl)phenyl)ethyl)amino)pyrimidin-4-yl)oxazolidin-2-one | 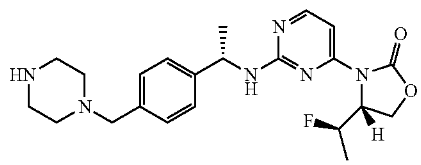 [SMILES: C[C@H](Nc1nccc(N2C(=O)OC[C@@H]2[C@@H](C)F)n1)c1ccc(CN2CCNCC2)cc1] | 429 |
| 84 | (R)-4-((R)-1-Hydroxyethyl)-3-(2-(((S)-1-(4-(piperazin-1-ylmethyl)phenyl)ethyl)amino)pyrimidin-4-yl)oxazolidin-2-one | 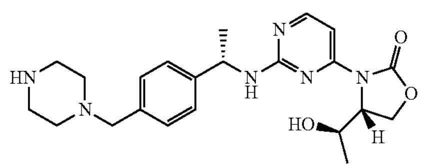 [SMILES: C[C@H](Nc1nccc(N2C(=O)OC[C@@H]2[C@@H](C)O)n1)c1ccc(CN2CCNCC2)cc1] | 427 |
| 85 | (R)-4-((S)-1-Methoxyethyl)-3-(2-(((S)-1-(4-(piperazin-1-ylmethyl)phenyl)ethyl)amino)pyrimidin-4-yl)oxazolidin-2-one | 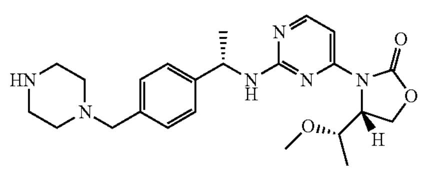 [SMILES: CO[C@@H](C)[C@H]1COC(=O)N1c1ccnc(N[C@@H](C)c2ccc(CN3CCNCC3)cc2)n1] | 441 |
| 86 | (R)-4-((R)-1-Methoxyethyl)-3-(2-(((S)-1-(4-(piperazin-1-ylmethyl)phenyl)ethyl)amino)pyrimidin-4-yl)oxazolidin-2-one | 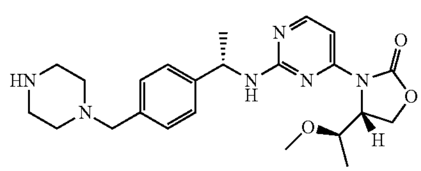 [SMILES: CO[C@H](C)[C@H]1COC(=O)N1c1ccnc(N[C@@H](C)c2ccc(CN3CCNCC3)cc2)n1] | 441 |
| 87 | 3-(2-(((1S)-1-(4-(1-(Piperazin-1-yl)propyl)phenyl)ethyl)amino)pyrimidin-4-yl)oxazolidin-2-one, isomer 1 | 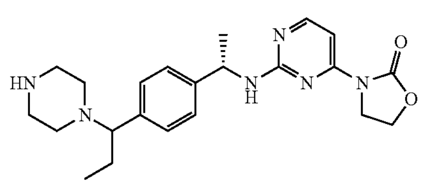 [SMILES: CCC(c1ccc([C@H](C)Nc2nccc(N3CCOC3=O)n2)cc1)N1CCNCC1] | 411 |
| 88 | 3-(2-(((1S)-1-(4-(1-(Piperazin-1-yl)propyl)phenyl)ethyl)amino)pyrimidin-4-yl)oxazolidin-2-one, isomer 2 | 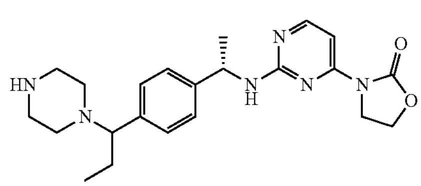 [SMILES: CCC(c1ccc([C@H](C)Nc2nccc(N3CCOC3=O)n2)cc1)N1CCNCC1] | 411 |

| Prep. No. | Chemical Name | Structure | ES/MS (m/z) (M + H) |
|---|---|---|---|
| 89 | (R)-3-(6-Fluoro-2-(((S)-1-(4-(piperazin-1-ylmethyl)phenyl)ethyl)amino)pyrimidin-4-yl)-4-((R)-1-methoxyethyl)oxazolidin-2-one | 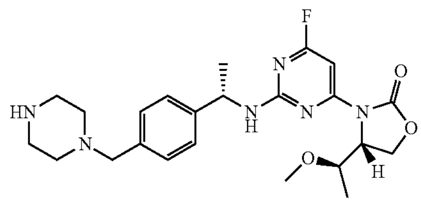 [SMILES: CO[C@H](C)[C@H]1COC(=O)N1c1cc(F)nc(N[C@@H](C)c2ccc(CN3CCNCC3)cc2)n1] | 459 |
| 90 | (R)-3-(6-Fluoro-2-(((S)-1-(4-(piperazin-1-ylmethyl)phenyl)ethyl)amino)pyrimidin-4-yl)-4-((S)-1-fluoroethyl)oxazolidin-2-one | 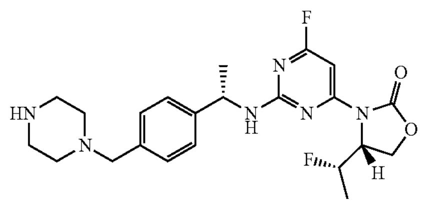 [SMILES: C[C@H](Nc1nc(F)cc(N2C(=O)OC[C@@H]2[C@H](C)F)n1)c1ccc(CN2CCNCC2)cc1] | 447 |

PREPARATION 91

(4S)-3-[2-[[(1S)-1-[4-[2-Cyclopropyl-1-piperazin-1-yl-ethyl]phenyl]ethyl]amino]pyrimidin-4-yl]-4-isopropyl-oxazolidin-2-one, Isomer 1

PREPARATION 92

(4R)-3-[2-[[(1S)-1-[4-(2-Cyclopropyl-1-piperazin-1-yl-ethyl)phenyl]ethyl]amino]pyrimidin-4-yl]-4-[(1R)-1-hydroxyethyl]oxazolidin-2-one

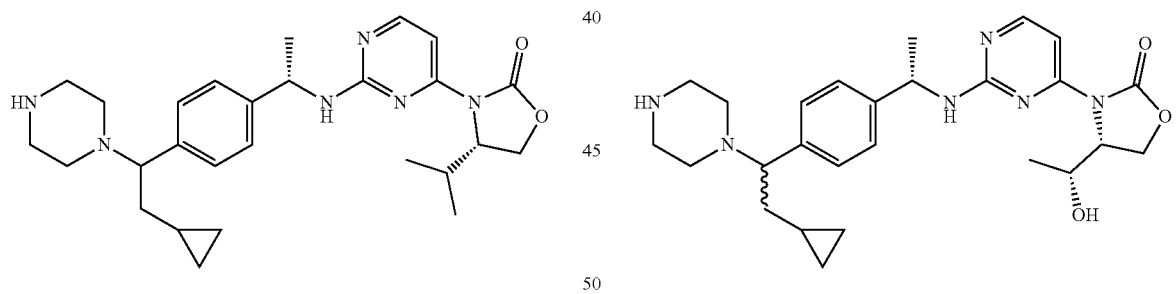

A solution of tert-butyl 4-[2-cyclopropyl-1-[4-[(1S)-1-[[4-[(4S)-4-isopropyl-2-oxo-oxazolidin-3-yl]pyrimidin-2-yl]amino]ethyl]phenyl]ethyl]piperazine-1-carboxylate, isomer 1 (1.97 g, 3.40 mmol) in CH₂Cl₂ (15 mL) is treated with TFA (5 mL, 66.13 mmol) and stirred at room temperature overnight. The solvent is removed and the residue dissolved in CH₂Cl₂. The pH of the solution is made basic with 10% aqueous sodium carbonate. The layers are separated and the aqueous layer is re-extracted with 2×CH₂Cl₂. The organic extracts are combined, dried over Na₂SO₄, filtered, and concentrated under reduced pressure to give the title compound (1.691 g, 97%). ES/MS m/z 479 (M+H).

TFA (2 mL) is added to a solution of tert-butyl 4-[1-[4-[(1S)-1-[[4-[(4R)-4-[(1R)-1-tert-butoxyethyl]-2-oxo-oxazolidin-3-yl]pyrimidin-2-yl]amino]ethyl]phenyl]-2-cyclopropyl-ethyl]piperazine-1-carboxylate (288 mg, 0.448 mmol) in (2 mL) and the mixture is stirred at room temperature. After about 2 hours, the mixture is concentrated and dissolved in MeOH. The solution is purified with an SCX column. The column is flushed with MeOH and the title compound is eluted with 1 N ammonia in MeOH. The ammonia/MeOH solution is concentrated to give the title compound as an oil (176 mg, 0.359 mmol, 80%) which is used without further purification. ES/MS (m/z): 481.2 (M+H).

PREPARATION 93

3-[6-Amino-2-[[(1S)-1-[4-[1-piperazin-1-ylpropyl]phenyl]ethyl]amino]pyrimidin-4-yl]-4,4-dimethyl-oxazolidin-2-one, Isomer 1

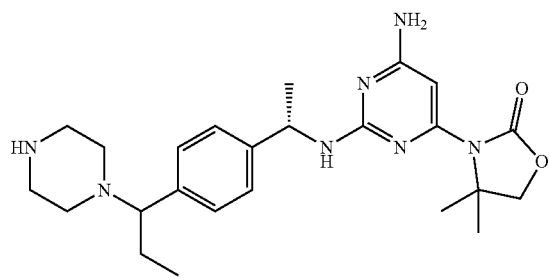 [SMILES: CCC(c1ccc([C@H](C)Nc2nc(N)cc(N3C(=O)OCC3(C)C)n2)cc1)N1CCNCC1]

A CH$_2$Cl$_2$ solution (13 mL) of tert-butyl 4-[1-[4-[(1S)-1-[[4-amino-6-(4,4-dimethyl-2-oxo-oxazolidin-3-yl)pyrimidin-2-yl]amino]ethyl]phenyl]propyl]piperazine-1-carboxylate (1.50 g, 2.55 mmol) is treated with TFA (4 mL) and allowed to stir at room temperature overnight. The reaction is diluted with 10% aqueous potassium carbonate and extracted with 3×CH$_2$Cl$_2$. The organic extracts are combined, dried over solid Na$_2$SO$_4$, filtered, and the solvent removed under reduced pressure to give the title compound as a pale yellow amorphous solid (1.285 g, 100%). ES/MS m/z 454 (M+H).

The following compound is prepared in essentially the same manner as the method of Preparation 93 using the appropriate intermediate.

PREPARATION 94

(S)-4-Ethyl-3-(2-(((S)-1-(4-(piperazin-1-ylmethyl)phenyl)ethyl)amino)pyrimidin-4-yl)oxazolidin-2-one

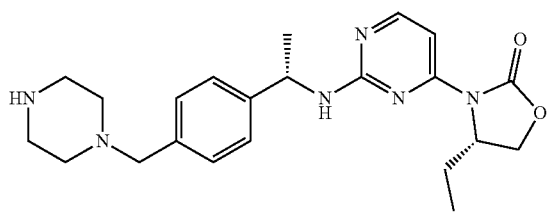

tert-Butyl 4-(4-((S)-1-((4-((S)-4-ethyl-2-oxooxazolidin-3-yl)pyrimidin-2-yl)amino)ethyl)benzyl)piperazine-1-carboxylate (749 mg, 1.47 mmol) is dissolved in a mixture of HCl (4 M in dioxane, 1.8 mL, 7.3 mmol) and CH$_2$Cl$_2$ (2.9 mL). The reaction mixture is stirred at room temperature for 2 hours and is then concentrated to give the HCl salt of the title compound which is desalted using a 25-g cation exchange SCX column that is pre-washed with MeOH and rinsed with 2 N NH$_3$ in MeOH to give the title compound as a colorless oil (491 mg, 1.20 mmol, 82%). ES/MS (m/z): 411 (M+H).

The following compound is prepared in a manner essentially the same manner as the method of Preparation 94 using the appropriate intermediate.

TABLE 16a

| Prep. No. | Chemical Name | Structure | ES/MS (m/z) (M + H) |
|---|---|---|---|
| 93a | 3-[6-Amino-2-[[(1S)-1-[4-[1-piperazin-1-ylpropyl]phenyl]ethyl]amino]pyrimidin-4-yl]-4,4-dimethyl-oxazolidin-2-one, isomer 2 | 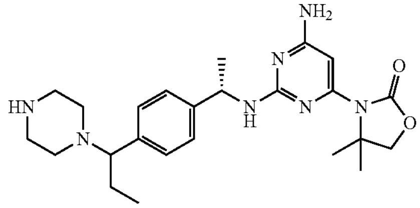 [SMILES: CCC(c1ccc([C@H](C)Nc2nc(N)cc(N3C(=O)OCC3(C)C)n2)cc1)N1CCNCC1] | 454 |

TABLE 17

| Prep. No. | Chemical Name | Structure | ES/MS (m/z) (M + H) |
|---|---|---|---|
| 95 | (S)-4-Methyl-3-(2-(((S)-1-(4-(piperazin-1-ylmethyl)phenyl)ethyl)amino)pyrimidin-4-yl)oxazolidin-2-one | 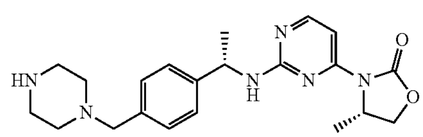 [SMILES: C[C@H](Nc1nccc(N2C(=O)OC[C@@H]2C)n1)c1ccc(CN2CCNCC2)cc1] | 397 |

3-[2-[[(1 S)-1-[4-[(2-Cyclopropyl-1-piperazin-1-yl-ethyl]phenyl]ethyl]amino]-6-fluoro-pyrimidin-4-yl]-4,4-dimethyl-oxazolidin-2-one dihydrochloride, Isomer 1

A solution of tert-butyl 4-[2-cyclopropyl-1-[4-[(1S)-1-[[4-(4,4-dimethyl-2-oxo-oxazolidin-3-yl)-6-fluoro-pyrimidin-2-yl]amino]ethyl]phenyl]ethyl]piperazine-1-carboxylate (1.11 g, 1.85 mmol) in CH$_2$Cl$_2$ (9 mL) is treated with HCl (4.0 mol/L in 1,4-dioxane (9.5 mL, 38 mmol) and stirred at room temperature for 3 hours. The reaction is concentrated under reduced pressure to give the title compound (1.142 g, 90 mass %, 100%) as a white solid. ES/MS m/z 483 (M+H of free base).

The following compound is prepared in essentially the same manner as the method of Preparation 96 using the appropriate intermediate.

Example 1

(S)-3-(2-(((S)-1-(4-((4-Acryloylpiperazin-1-yl)methyl)phenyl)ethyl)amino)pyrimidin-4-yl)-4-isopropyloxazolidin-2-one To a solution of (S)-4-isopropyl-3-(2-(((S)-1-(4-(piperazin-1-ylmethyl)phenyl)ethyl)amino)pyrimidin-4-yl)oxazolidin-2-one (4.6 g, 11 mmol) in CH$_2$Cl$_2$ (100 mL) is added acryloyl chloride (0.97 mL, 12 mmol) at 0° C. After 15 minutes, saturated aqueous NaHCO$_3$ is added and the cooling bath is removed. The resulting mixture is diluted further with brine and is extracted with CH$_2$Cl$_2$ (3×), dried (MgSO$_4$), filtered, and concentrated to give a white solid which is purified by silica gel chromatography eluting with 50-100% hexanes/[10% MeOH in acetone] to give the title compound as a white solid (4.35 g, 9.1 mmol, 84%). ES/MS (m/z): 479 (M+H).

The following compounds are prepared in essentially the same manner as the method of Example 1 using the appropriate intermediate.

TABLE 17a

| Prep. No. | Chemical Name | Structure | ES/MS (m/z) (M + H) |
|---|---|---|---|
| 96a | 3-[2-[[(1S)-1-[4-[(2-Cyclopropyl-1-piperazin-1-yl-ethyl]phenyl]ethyl]amino]-6-fluoro-pyrimidin-4-yl]-4,4-dimethyl-oxazolidin-2-one dihydrochloride, isomer 2 | 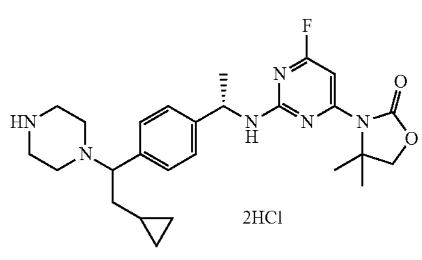 [SMILES: C[C@H](Nc1nc(F)cc(N2C(=O)OCC2(C)C)n1)c1ccc(C(CC2CC2)N2CCNCC2)cc1] | 483 |

TABLE 18

| Ex. No. | Chemical Name | Structure | ES/MS (m/z) (M + H) |
|---|---|---|---|
| 2 | (S)-3-(2-(((S)-1-(4-((4-acryloylpiperazin-1-yl)methyl)phenyl)ethyl)amino)pyrimidin-4-yl)-4-ethyloxazolidin-2-one | 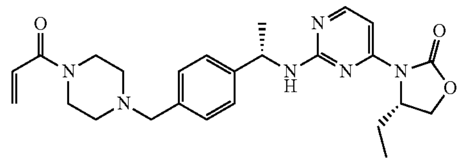 [SMILES: C=CC(=O)N1CCN(Cc2ccc([C@H](C)Nc3nccc(N4C(=O)OC[C@@H]4CC)n3)cc2)CC1] | 465 |
| 3 | (S)-3-(2-(((S)-1-(4-((4-acryloylpiperazin-1-yl)methyl)phenyl)ethyl)amino)pyrimidin-4-yl)-4-methyloxazolidin-2-one | 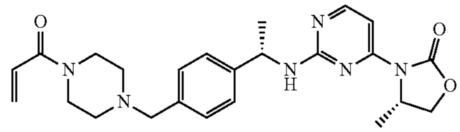 [SMILES: C=CC(=O)N1CCN(Cc2ccc([C@H](C)Nc3nccc(N4C(=O)OC[C@@H]4C)n3)cc2)CC1] | 451 |
| 4 | (S)-3-(2-((1-(4-((4-acryloylpiperazin-1-yl)methyl)phenyl)ethyl)amino)pyrimidin-4-yl)-4,4-dimethyloxazolidin-2-one | 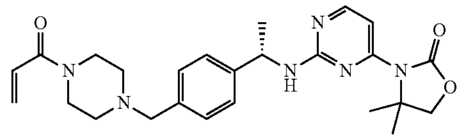 [SMILES: C=CC(=O)N1CCN(Cc2ccc([C@H](C)Nc3nccc(N4C(=O)OCC4(C)C)n3)cc2)CC1] | 465 |
| 5 | (S)-3-(2-(((S)-1-(4-((4-acryloylpiperazin-1-yl)methyl)phenyl)ethyl)amino)-5-fluoropyrimidin-4-yl)-4-isopropyloxazolidin-2-one | 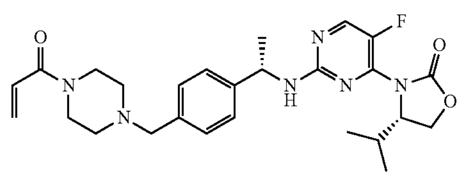 [SMILES: C=CC(=O)N1CCN(Cc2ccc([C@H](C)Nc3ncc(F)c(N4C(=O)OC[C@@H]4C(C)C)n3)cc2)CC1] | 497 |
| 6 | (S)-3-(2-(((S)-1-(4-((4-acryloylpiperazin-1-yl)methyl)phenyl)ethyl)amino)-6-fluoropyrimidin-4-yl)-4-isopropyloxazolidin-2-one | 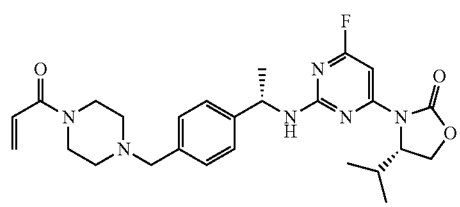 [SMILES: C=CC(=O)N1CCN(Cc2ccc([C@H](C)Nc3nc(F)cc(N4C(=O)OC[C@@H]4C(C)C)n3)cc2)CC1] | 497 |
| 7 | (R)-3-(2-(((S)-1-(4-((4-acryloylpiperazin-1-yl)methyl)phenyl)ethyl)amino)pyrimidin-4-yl)-4-(fluoromethyl)oxazolidin-2-one | 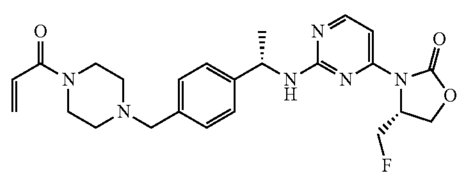 [SMILES: C=CC(=O)N1CCN(Cc2ccc([C@H](C)Nc3nccc(N4C(=O)OC[C@@H]4CF)n3)cc2)CC1] | 469 |
| 8 | (S)-3-(2-((1-(4-((4-acryloylpiperazin-1-yl)methyl)phenyl)ethyl)amino)-5-fluoropyrimidin-4-yl)-4,4-dimethyloxazolidin-2-one | 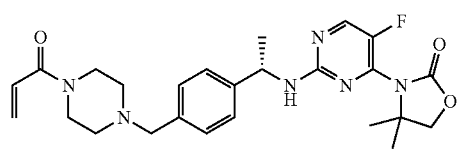 [SMILES: C=CC(=O)N1CCN(Cc2ccc([C@H](C)Nc3ncc(F)c(N4C(=O)OCC4(C)C)n3)cc2)CC1] | 483 |
| 9 | (S)-3-(2-(1-(4-((4-acryloylpiperazin-1-yl)methyl)phenyl)-2-fluoroethyl)amino)pyrimidin-4-yl)-4-ethyloxazolidin-2-one, isomer 2 | 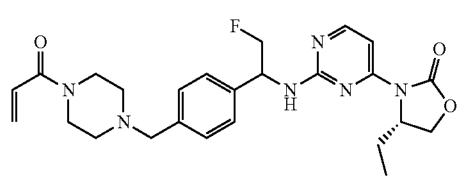 [SMILES: C=CC(=O)N1CCN(Cc2ccc(C(CF)Nc3nccc(N4C(=O)OC[C@@H]4CC)n3)cc2)CC1] | 483 |
| 10 | 3-(2-((1-(4-((4-acryloylpiperazin-1-yl)methyl)phenyl)-2-fluoroethyl)amino)pyrimidin-4-yl)-4,4-dimethyloxazolidin-2-one, isomer 2 | 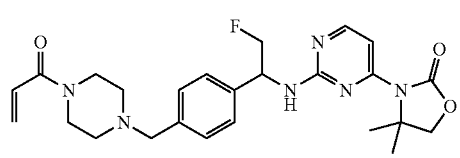 [SMILES: C=CC(=O)N1CCN(Cc2ccc(C(CF)Nc3nccc(N4C(=O)OCC4(C)C)n3)cc2)CC1] | 483 |

TABLE 18-continued

| Ex. No. | Chemical Name | Structure | ES/MS (m/z) (M + H) |
|---|---|---|---|
| 11 | (S)-3-(2-((1-(4-((4-acryloylpiperazin-1-yl)methyl)phenyl)ethyl)amino)-6-fluoropyrimidin-4-yl)-4,4-dimethyloxazolidin-2-one | 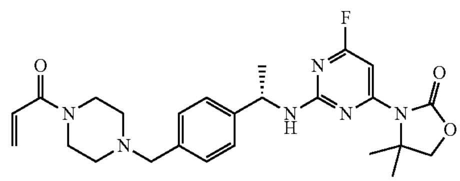 [SMILES: C=CC(=O)N1CCN(Cc2ccc([C@H](C)Nc3nc(F)cc(N4C(=O)OCC4(C)C)n3)cc2)CC1] | 483 |
| 12 | (R)-3-(2-(((S)-1-(4-((4-acryloylpiperazin-1-yl)methyl)phenyl)ethyl)amino)pyrimidin-4-yl)-4-((R)-1-fluoroethyl)oxazolidin-2-one | 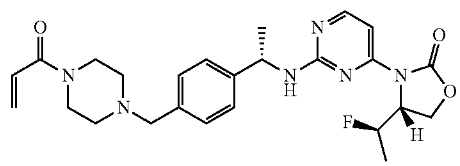 [SMILES: C=CC(=O)N1CCN(Cc2ccc([C@H](C)Nc3nccc(N4C(=O)OC[C@@H]4[C@@H](C)F)n3)cc2)CC1] | 483 |
| 13 | (R)-3-(2-(((S)-1-(4-((4-acryloylpiperazin-1-yl)methyl)phenyl)ethyl)amino)pyrimidin-4-yl)-4-((R)-1-hydroxyethyl)oxazolidin-2-one | 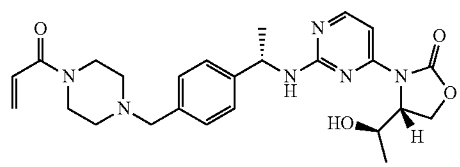 [SMILES: C=CC(=O)N1CCN(Cc2ccc([C@H](C)Nc3nccc(N4C(=O)OC[C@@H]4[C@@H](C)O)n3)cc2)CC1] | 481 |
| 14 | (R)-3-(2-(((S)-1-(4-((4-acryloylpiperazin-1-yl)methyl)phenyl)ethyl)amino)pyrimidin-4-yl)-4-((S)-1-methoxyethyl)oxazolidin-2-one | 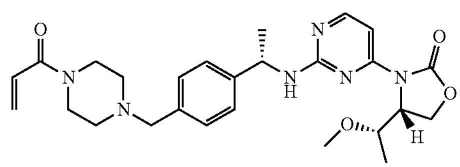 [SMILES: C=CC(=O)N1CCN(Cc2ccc([C@H](C)Nc3nccc(N4C(=O)OC[C@@H]4[C@H](C)OC)n3)cc2)CC1] | 495 |
| 15 | (R)-3-(2-(((S)-1-(4-((4-acryloylpiperazin-1-yl)methyl)phenyl)ethyl)amino)pyrimidin-4-yl)-4-((R)-1-methoxyethyl)oxazolidin-2-one | 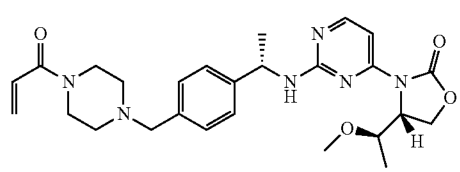 [SMILES: C=CC(=O)N1CCN(Cc2ccc([C@H](C)Nc3nccc(N4C(=O)OC[C@@H]4[C@@H](C)OC)n3)cc2)CC1] | 495 |
| 16 | 3-(2-(((1S)-1-(4-(1-(4-acryloylpiperazin-1-yl)propyl)phenyl)ethyl)amino)pyrimidin-4-yl)oxazolidin-2-one, isomer 1 | 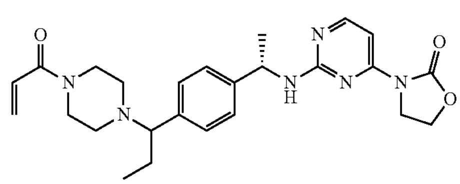 [SMILES: C=CC(=O)N1CCN(C(CC)c2ccc([C@H](C)Nc3nccc(N4CCOC4=O)n3)cc2)CC1] | 465 |

TABLE 18-continued

| Ex. No. | Chemical Name | Structure | ES/MS (m/z) (M + H) |
|---|---|---|---|
| 17 | 3-(2-(((1S)-1-(4-(1-(4-acryloylpiperazin-1-yl)propyl)phenyl)ethyl)amino)pyrimidin-4-yl)oxazolidin-2-one, isomer 2 | 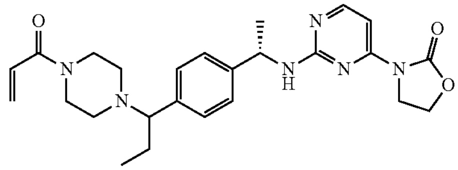 [SMILES: C=CC(=O)N1CCN(C(CC)c2ccc([C@H](C)Nc3nccc(N4CCOC4=O)n3)cc2)CC1] | 465 |
| 18 | (R)-3-(2-(((S)-1-(4-((4-acryloylpiperazin-1-yl)methyl)phenyl)ethyl)amino)-6-fluoropyrimidin-4-yl)-4-((R)-1-methoxyethyl)oxazolidin-2-one | 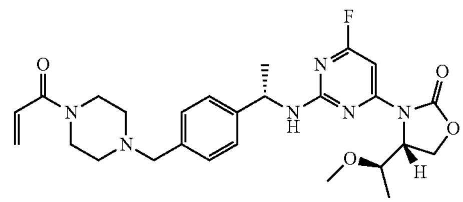 [SMILES: C=CC(=O)N1CCN(Cc2ccc([C@H](C)Nc3nc(F)cc(N4C(=O)OC[C@@H]4[C@@H](C)OC)n3)cc2)CC1] | 513 |
| 19 | (R)-3-(2-(((S)-1-(4-((4-acryloylpiperazin-1-yl)methyl)phenyl)ethyl)amino)-6-fluoropyrimidin-4-yl)-4-((S)-1-fluoroethyl)oxazolidin-2-one | 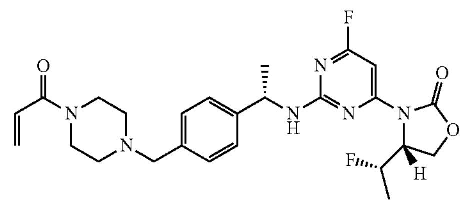 [SMILES: C=CC(=O)N1CCN(Cc2ccc([C@H](C)Nc3nc(F)cc(N4C(=O)OC[C@@H]4[C@H](C)F)n3)cc2)CC1] | 501 |

Example 20

(4S)-3-[2-[[(1S)-1-[4-[2-Cyclopropyl-1-(4-prop-2-enoylpiperazin-1-yl)ethyl]phenyl]ethyl]amino]pyrimidin-4-yl]-4-isopropyl-oxazolidin-2-one, Isomer 1

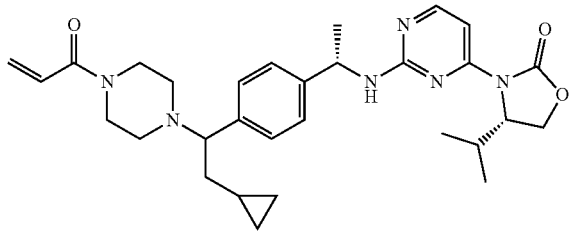 [SMILES: C=CC(=O)N1CCN(C(CC2CC2)c2ccc([C@H](C)Nc3nccc(N4C(=O)OC[C@@H]4C(C)C)n3)cc2)CC1]

A solution of (4S)-3-[2-[[(1S)-1-[4-[2-cyclopropyl-1-piperazin-1-yl-ethyl]phenyl]ethyl]amino]pyrimidin-4-yl]-4-isopropyl-oxazolidin-2-one, isomer 1 (1.665 g, 3.270 mmol) in CH$_2$Cl$_2$ (30 mL) is cooled to 0° C., treated drop-wise with a solution of acryloyl chloride (306 μL, 3.760 mmol) in CH$_2$Cl$_2$ (3 mL) and stirred at room temperature. The mixture is quenched with MeOH (about 3 mL), then aqueous sodium bicarbonate, and allowed to warm to room temperature. The layers are separated and the aqueous layer re-extracted with 3×CH$_2$Cl$_2$. The organic extracts are combined, dried over Na$_2$SO$_4$, filtered, and the solvent removed under reduced pressure to give the crude product. The crude material is purified with silica gel flash chromatography eluting with a gradient of 20 to 40% (10% MeOH in acetone) in hexanes to give the title compound as an amorphous solid (1.304 g, 74%). ES/MS m/z 533 (M+H).

The following compound is prepared in essentially the same manner as the method of Example 20 using the appropriate intermediate.

TABLE 19

| Ex. No. | Chemical Name | Structure | ES/MS (m/z) (M + H) |
|---|---|---|---|
| 21 | (4S)-3-[2-[[(1S)-1-[4-[2-Cyclopropyl-1-(4-prop-2-enoylpiperazin-1-yl)ethyl]phenyl]ethyl]amino]pyrimidin-4-yl]-4-isopropyl-oxazolidin-2-one, isomer 2 | 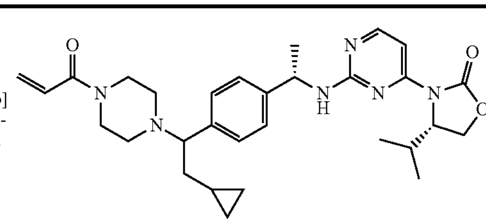 | 533 |

Example 22

3-[2-[[(1S)-1-[4-[2-Cyclopropyl-1-(4-prop-2-enoylpiperazin-1-yl)ethyl]phenyl]ethyl]amino]-6-fluoro-pyrimidin-4-yl]-4,4-dimethyl-oxazolidin-2-one, Isomer 1

Example 24

3-[6-Amino-2-[[(1S)-1-[4-[1-(4-prop-2-enoylpiperazin-1-yl)propyl]phenyl]ethyl]amino]pyrimidin-4-yl]-4,4-dimethyl-oxazolidin-2-one, Isomer 1

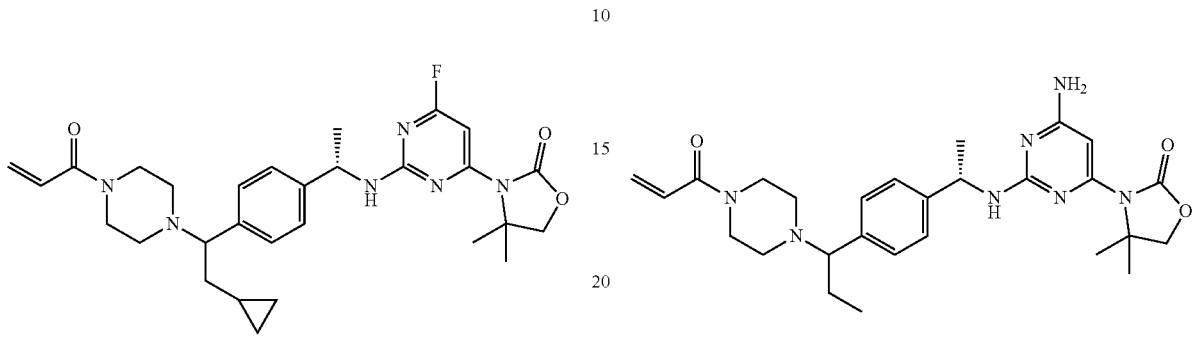

A solution of 3-[2-[[(1S)-1-[4-[2-cyclopropyl-1-piperazin-1-yl-ethyl]phenyl]ethyl]amino]-6-fluoro-pyrimidin-4-yl]-4,4-dimethyl-oxazolidin-2-one, isomer 1 dihydrochloride (1.118 g, 1.811 mmol, 90 mass %) in $CH_2Cl_2$ (about 50 mL) is treated with saturated $NaHCO_3$ and the layers are separated. The aqueous layer is extracted with additional 2×$CH_2Cl_2$ and the combined organics are dried over $Na_2SO_4$. The $CH_2Cl_2$ solution (about 100 mL) is cooled to 0° C., treated dropwise with a solution of acryloyl chloride (170 µL, 2.089 mmol) in $CH_2Cl_2$ (1 mL) and stirred at 0° C. for 2 minutes. The mixture is quenched with MeOH (about 1 mL), diluted with saturated $NaHCO_3$, and allowed to warm to room temperature. The reaction is extracted with 2×$CH_2Cl_2$. The organic extracts are combined, dried over $Na_2SO_4$, concentrated under reduced pressure, and purified by silica gel flash chromatography with 10% to 30% (10% MeOH in acetone) in hexanes to give the title compound (870 mg, 89%) as a white amorphous solid. ES/MS m/z 537 (M+H).

The following compound is prepared in essentially the same manner as the method of Example 22 using the appropriate intermediate.

A $CH_2Cl_2$ solution (24 mL) of 3-[6-amino-2-[[(1S)-1-[4-[1-piperazin-1-ylpropyl]phenyl]ethyl]amino]pyrimidin-4-yl]-4,4-dimethyl-oxazolidin-2-one, isomer 1 (1.26 g, 2.78 mmol) is cooled in an ice bath. When cold, the solution is treated with a $CH_2Cl_2$ solution (1 mL) of acryloyl chloride (224 µL, 2.75 mmol) dropwise via syringe giving a viscous oil precipitate. The suspension is cooled to −78° C., treated with TEA (387 µL, 2.78 mmol), and allowed to stir at −78° C. for 15 minutes. The reaction is quenched with MeOH (1 mL), diluted with saturated, aqueous sodium bicarbonate, and allowed to warm to room temperature. The layers are separated and the aqueous layer is extracted with 2×$CH_2Cl_2$. The organic extracts are combined, dried over $Na_2SO_4$, filtered, and the solvent removed under reduced pressure. The crude material is purified by silica gel flash chromatography eluting with a gradient of 2% to 5% MeOH in $CH_2Cl_2$ to give the title compound (855 mg, 59%) as a white amorphous solid. ES/MS m/z 508 (M+H).

The following compound is prepared in essentially the same manner as the method of Example 24 using the appropriate intermediate.

TABLE 20

| Ex. No. | Chemical Name | Structure | ES/MS (m/z) (M + H) |
|---|---|---|---|
| 23 | 3-[2-[[(1S)-1-[4-[2-Cyclopropyl-1-(4-prop-2-enoylpiperazin-1-yl)ethyl]phenyl]ethyl]amino]-6-fluoro-pyrimidin-4-yl]-4,4-dimethyl-oxazolidin-2-one, isomer 2 | 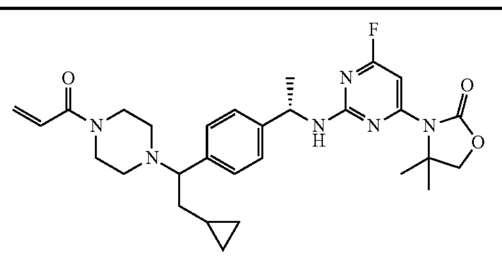 | 537 |

TABLE 21

| Ex. No. | Chemical Name | Structure | ES/MS (m/z) (M + H) |
|---|---|---|---|
| 25 | 3-[6-Amino-2-[[(1S)-1-[4-[1-(4-prop-2-enoylpiperazin-1-yl)propyl]phenyl]ethyl]amino]pyrimidin-4-yl]-4,4-dimethyl-oxazolidin-2-one, isomer 2 | 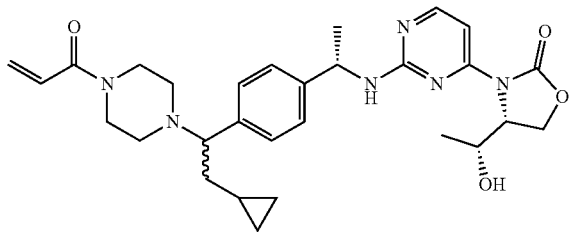 [SMILES: C=CC(=O)N1CCN(C(CC2CC2)c2ccc([C@H](C)Nc3nccc(N4C(=O)OC[C@@H]4[C@@H](C)O)n3)cc2)CC1] | 508 |

Example 26

4R)-3-[2-[[(1S)-1-[4-[2-Cyclopropyl-1-(4-prop-2-enoylpiperazin-1-yl)ethyl]phenyl]ethyl]amino]pyrimidin-4-yl]-4-[(1R)-1-hydroxyethyl]oxazolidin-2-one Acryloyl chloride (1.23 M in CH$_2$Cl$_2$, 0.292 mL, 0.3589 mmol) is added to a solution of (4R)-3-[2-[[(1S)-1-[4-(2-cyclopropyl-1-piperazin-1-yl-ethyl)phenyl]ethyl]amino]pyrimidin-4-yl]-4-[(1R)-1-hydroxyethyl]oxazolidin-2-one (176 mg, 0.3589 mmol) in CH$_2$Cl$_2$ (5 mL) and cooled in a dry ice acetone bath. After −20 minutes, the mixture is partitioned between CH$_2$Cl$_2$ and saturated sodium bicarbonate solution. The organic layer is washed with saturated aqueous NaCl, dried over Na$_2$SO$_4$, filtered, and concentrated. The crude residue is purified with silica gel chromatography eluting with 10% to 70% [10% MeOH in EtOAc] in CH$_2$Cl$_2$ to give the title compound as a white solid (199 mg, 100%). ES/MS (m/z): 535.4 (M+H).

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenvironments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Extensive catalogues of the cytogenetic aberrations in human cancer have been compiled and are maintained and regularly updated online (see The Mitelman Database of Chromosome Aberrations in Cancer at the US National Cancer Institute (NCI) Cancer Genome Anatomy Project (CGAP) Web site). The Wellcome Trust Sanger Institute Cancer Genome Project maintains a detailed online "Cancer Gene Census" of all human genes that have been causally linked to tumorigenesis as well as the COSMIC (Catalogue of Somatic Mutations in Cancer) database of somatic mutations in human cancer. A further source containing abundant information on cytogenetic changes causally linked to various cancers is the Atlas of Genetics and Cytogenetics in Oncology and Haematology.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

Mutations in IDH1 have been identified in multiple cancer tumor types including, but not limited to, glioma, glioblastoma multiforme (GBM), astrocytoma, oligodendroglioma, paraganglioma, myelodysplastic syndrome (MDS), B cell acute lymphoblastic leukemia (B-ALL), thyroid, colorectal, acute myeloid leukemia (AML), Dang et al., *Trends Mol. Med.*, 2010, 16: 387-397; Ward et al., *Oncogene*, 2012, 31(19): 2491-2498; melanoma, Shibata et al., *Am. J. Pathol.*, 2010, 178(3): 1395-1402; prostate, Flaherty et al., *J. Clin. Oncol.*, 2014, 32 (suppl. 4; Abstract 213); Cairns et al., *Cancer Discovery*, 2013, 3: 730-741; chondrosarcoma and cholangiocarcinoma, Balss et al., *Acta Neuropathol.*, 2012, 124: 883-891; Cairns et al., *Cancer Discovery*, 2013, 3: 730-741, angioimmunoblastic T-cell lymphoma (AITL), Cairns et al. *Blood*, 2012. 119(8):1901-1903. Mutations have been found at or near particular residues in the active site: G97D, R100, R132H, R132C, R132S, R132V, R132G, V71I, R132L, and G123R for IDH1, Dang et al., *Trends Mol. Med.*, 2010, 16: 387-397; Ward et al., 2012 and Supplementary Table 2.

Mutant forms of IDH1 have been shown to have a neomorphic activity (gain of function) reducing α-ketoglutarate to 2-hydroxyglutarate. Endogenous production of 2-hydroxyglutarate is enantiospecific resulting in the generation of the D-enantiomer (also termed the (R) enantiomer). Normally, cells have low levels of 2-hydroxyglutarate while cells harboring IDH1 mutations evidence significantly elevated levels of 2-hydroxyglutarate. Significantly elevated levels of 2-hydroxyglutarate are detected in tumors harboring the mutations and in plasma of patients with mutant IDH1. High levels of 2-hydroxyglutarate are associated with a hypermethylation phenotype resulting in a block in differentiation that leads to enhanced tumorigenesis.

The activity of a specific irreversible covalent inhibitor is defined by its binding to the target (IDH1), defined by $K_I$, and the maximum potential rate of covalent bond formation, defined by $k_{inact}$. These two factors are not separate entities, but rather work together to produce the desired effect of covalent bond formation. This is illustrated by the following 3 points.

First, the fact that an electrophile for example, acrylamide, must be properly positioned relative to a nucleophile for example, cysteine, is a fundamental component of covalent bond formation in organic chemistry. There is a precise angle and distance at which the nucleophile must approach the electrophile to form the covalent bond. The simple placement of an electrophile near a nucleophile is not sufficient for covalent bond formation.

Second, when incorporating a reactive group on a core that contains hydrogen bonding moieties to stabilize the binding of the inhibitor to the enzyme for example, an orienting core, a skilled artisan must consider how the orienting core binds to the target and positions the electrophile relative to the nucleophile in light of the optimal angle and distance mentioned above. Again, the simple placement of an electrophile near a nucleophile is not sufficient for covalent bond formation. Changes in the orienting core may impact the ability of an inhibitor compound to form a covalent bond.

Third, when the above two points are considered together, the mere presence of an electrophile moiety on an orienting core is not sufficient to suggest a covalent bond will be formed.

The following in vitro and in vivo studies demonstrate the mutant IDH1 protein inhibitory activity and efficacy of the tested compounds of Formula I against various specific cancer cell lines. These assays are generally recognized by those skilled in the art as predictive of human clinical therapeutic activity against proliferative neoplasms containing cancer cells with these mutant IDH1 enzymes. Assays evidencing mutant IDH1 inhibitory activity and efficacy may be carried out substantially as follows or by similar assays affording similar data.

The results of the following assays demonstrate that the compounds exemplified and tested are useful as IDH1 mutant inhibitors, are covalent inhibitors, and may be useful in treating cancers expressing mutant IDH1. In each of the assays below where the specified Art compound is tested, additional art compounds are made, tested and afford similar data.

Biochemical Assays for IDH1 and IDH2 Mutant Enzymes

IDH1-R132H, IDH1-R132C, IDH2-R172K, and IDH2-R140Q mutant enzymes catalyze the conversion of αKG to 2HG. 2HG is analyzed using in-line solid phase extraction and mass spectrometry. This analysis is carried out in a RapidFire® instrument coupled to a 6460 triple quadrupole mass spectrometer (G6460A Agilent).

IDH1 mutant (R132H and R132C) and IDH2 mutant (R140Q and R172K) proteins containing N-terminal His-tag are expressed in *E. coli* and purified using nickel affinity chromatography by methods commonly used and well known to those skilled in the art. The enzyme assays are carried out in V-bottom 96 well polypropylene plates containing 100 mM Tris-HCl buffer, 1 mM DTT, 0.005% TRITON™ X-100, 120 mM NaCl. For IDH1 R132H, α-ketoglutarate, NADPH and $MnCl_2$ are included at final concentrations of 300 μM, 2.5 μM and 300 μM respectively. For IDH1 R132C, α-ketoglutarate, NADPH and $MnCl_2$ are included at final concentrations of 100 μM, 10 μM and 100 μM respectively. For IDH2 R172K, α-ketoglutarate, NADPH, and $MnCl_2$ are included at final concentrations of 150 μM, 10 μM and 150 μM respectively. For IDH2 R140Q, α-ketoglutarate, NADPH, and $MnCl_2$ are included at final concentrations of 300 μM, 10 μM, and 100 μM respectively. Final pH=7.0. Test compound, dissolved in DMSO stock, is diluted in the reaction mixture at a final DMSO concentration of 4%. Compounds are tested in dose-response format. The assay is started by addition of enzyme. Enzymes are used at the following final concentrations: IDH1 R132H, 2 nM; IDH1 R132C, 0.5 nM; IDH2 R172K, 1.2 nM; IDH2 R140Q, 1.2 nM and the assay is allowed to continue for the following times: 40 minutes for IDH-1R132C, 60 minutes for IDH-1HR132H and 50 minutes for the IDH-2172K and IDH-2R140Q enzymes. The reaction is quenched by adding ACN (50:50) containing $d_5$-3HG as an internal standard for mass spectrometry analysis and quantitation of reaction product. 2HG in quenched samples is separated using strong anionic exchange column chromatography (Phenomenex Strata-X-A SecurityGuard, 4×3 mm) and analyzed by mass spectrometry in a 6460 triple quadrupole mass spectrometer (G6460A Agilent). The 2HG signal detected is transformed into an analyte concentration using a calibration curve generated using known 2HG concentrations. For each compound tested, the % inhibition is calculated using a DMSO control sample as 0% inhibition and a no enzyme control as 100% inhibition. $IC_{50}$ values are obtained from the individual % inhibition values at different compound concentrations using a 4-parameter equation. These calculations are carried out using Activity Base (IDBS) or Screener (Genedata) data analysis programs.

The results of this assay demonstrate that the exemplified and tested compounds inhibit mutant IDH1 activity against IHD1/R132H and IDH1/R132C.

The following Examples are tested essentially as described above and exhibit activity for mutant IDH1 as shown in Table 22 below and are selective for mutant IDH1 over mutant IDH2 (data not shown for mutant IDH2).

TABLE 22

| Example # | IDH1/R132H $IC_{50}$ (μM) | IDH1/R132C $IC_{50}$ (μM) |
| --- | --- | --- |
| 1 | 0.0364 ± 0.0063, n = 5 | 0.0192 ± 0.0044, n = 5 |
| 2 | 0.0306 | 0.0242 |
| 3 | 0.246 | 0.21 |
| 4 | 0.141 ± 0.066, n = 3 | 0.0968 ± 0.0297, n = 3 |
| 5 | 0.0466 | 0.0353 |
| 6 | 0.0276 | 0.0223 |
| 7 | 0.323 | 0.149 |
| 8 | 0.495 | 0.25 |
| 9 | 0.176 | 0.101 |

TABLE 22-continued

| Example # | IDH1/R132H IC$_{50}$ (μM) | IDH1/R132C IC$_{50}$ (μM) |
|---|---|---|
| 10 | 0.261 | 0.187 |
| 11 | 0.109 ± 0.025, n = 3 | 0.0835 ± 0.0072, n = 3 |
| 12 | 0.0846 | 0.0568 |
| 13 | 0.428 ± 0.0536, n = 2 | 0.272 ± 0.062, n = 2 |
| 14 | 0.0909 | 0.102 |
| 15 | 0.316 | 0.123 |
| 16 | 0.125 | 0.291 |
| 17 | 0.273 | 0.586 |
| 18 | 0.194 | 0.206 |
| 19 | 0.0501 | 0.0353 |
| 20 | <0.00508 | <0.00508 |
| 21 | <0.00508 | <0.00508 |
| 22 | 0.0256 | 0.0219 |
| 23 | <0.00508 | <0.00508 |
| 24 | 0.0385 | 0.0180 ± 0.0177, n = 2 |
| 25 | 0.0110 | 0.00889 ± 0.00053, n = 2 |
| 26 | 0.0125 ± 0.0054 | 0.0182 ± 0.0074, n = 2 |
| *Art compound | 0.0510 ± 0.0093, n = 4 | 0.0252 ± 0.0071, n = 4 |

Mean is ± SEM (SEM refers to standard error of mean)
*Art compound, (4S)-3-(2-{[(1S)-1-{4-[(4-Acetylpiperazin-1-yl)methyl]phenyl}ethyl]amino}pyrimidin-4-yl)-4-(propan-2-yl)-1,3-oxazolidin-2-one, prepared as in WO13/046136, example number 556.

The results of this assay demonstrate that the Example compounds listed in Table 22 are less active at inhibiting the IDH1 wild-type enzyme compared to the IDH1 R132H or R132C mutant enzymes.

IDH1 (R132H) Biochemical Jump Dilution Assay

Lyophilized Example compounds are reconstituted to 10 mM or 100 mM with 100% DMSO and kept at room temperature until tested. IDH1(R132H)-His protein is expressed and purified by methods well known and commonly used by those skilled in the art. The assay reagents included the following: α-ketoglutaric acid (Sigma Cat#K1875), MnCl$_2$—Fisher Scientific Cat# M87-100, NADPH—Sigma-Aldrich Cat# N7505, Tris-HCl (Invitrogen, Cat#15567-027), NaCl (Sigma, S3014), dithiothreitol (Sigma, D5545), and TritonX100 (Peirce, 28314). The NAD(P)H-Glo™ Kit from Promega (G9061).

The assay buffer used throughout contains 100 mM Tris-HCl pH 7.0, 120 mM NaCl, 1 mM DTT, 0.005% Triton X-100, and 2% DMSO (from the addition of test compound). The IC$_{50}$ of each compound is determined by incubating a dose response of compound, prepared on an Echo555, with 1.5 nM IDH1(R132H), 1 mM α-ketoglutarate, 1 mM MnCl$_2$, and 15 μM NADPH in assay buffer. The reaction is incubated for 2 hours at room temperature, then stopped using 6-cyclopropyl-5-(isoquinolin-5-yl)-2-[(3R)-4-(3-methoxypropanoyl)-3-methylpiperazin-1-yl]pyridine-3-carbonitrile (10 μM). NADPH concentrations are measured using the NAD(P)H-Glo™ Kit, as specified by the vendor. The luminescent signal is read on the Envision (Perkin Elmer; 0.1 sec/Luminescense Mirror/Lum700 WL400-700 filter). In the subsequent jump dilution experiment, a compound concentration equivalent to 10× the IC$_{50}$ is pre-incubated with 100 nM IDH1(R132H). The concentration of compound is always greater than or equal to the enzyme concentration. After 2 hours at room temperature, this mixture is diluted 1:100 into a solution containing α-ketoglutarate (10 mM), MnCl$_2$ (10 mM), and NADPH (15 M). This final enzyme reaction contains 1 nM IDH1(R132H) and 0.1×[IC$_{50}$]. After a 2 hour incubation at room temperature, the NADPH concentration is measured as specified above using 6-cyclopropyl-5-(isoquinolin-5-yl)-2-[(3R)-4-(3-methoxypropanoyl)-3-methylpiperazin-1-yl]pyridine-3-carbonitrile and the NAD(P)H-Glo™ Kit. Three controls are included: 1) "10× Control" containing 10×IC$_{50}$ compound in the preincubation and enzyme assay except 1 mM α-ketoglutarate, 1 mM MnCl$_2$, and 15 μM NADPH is used in the final assay measuring enzyme activity, 2) "Max Activity Control" containing DMSO in place of compound for both the preincubation and enzyme assay, and 3) "0.1× Control" containing DMSO in place of compound in the preincubation and 0.1×IC$_{50}$ compound in the enzyme assay. A "Min Activity Control" lacking enzyme, but otherwise equivalent to the "Max Activity Control" is included. A second set of Max and Min Activity Controls is performed using 1 mM α-ketoglutarate, 1 mM MnCl$_2$, and 15 μM NADPH. Each assay condition is tested in triplicate and 32 replicates are performed for the Max Activity Control (10 mM) and Min Activity Control (10 mM) while 16 replicates are performed for the Max Activity Control (1 mM) and Min Activity Control (1 mM).

The concentration of NADP (product) produced in each experiment/control is determined using the percent decrease in the observed signal relative to the Min Activity Control, containing 15 μM NADPH. The Min Activity Control (1 mM and 1 0 mM) and the Max Activity Control (1 mM and 10 mM) are averaged and the standard deviation calculated for each. The signal for each jump dilution and for the 0.1× Controls are multiplied by 15 then divided by the average counts for the Min Activity Control (10 mM) wells. This number is subtracted from 15 to calculate NADP (μM Product). The same calculations are used for the 10× Controls but the Min activity controls (1 mM) are used. The moles of the product for the Max Activity controls (1 mM and 10 mM) are calculated by multiplying the average counts by 15 then divide by the respective Min Activity Controls (1 mM and 10 mM). The μM NADP for each well is divided by the average Max Activity Control (1 mM or 10 mM) then multiplied by 100 to determine % IDH Activity for the compound jump dilution, 10× Control, and 0.1× Control. A passing compound must show <30% activity for the 10× control—showing that the preincubation concentration is sufficient to saturate the enzyme with compound. In addition, the compound must show >70-80% activity for the 0.1× control confirming that there is no inhibition at the 0.1×/diluted compound concentration.

The following Examples are tested essentially as described above and exhibit % recovery data for IDH1/R132H in this assay as shown in Table 23 below.

The Examples shown below inhibit the enzyme 2 hours after dilution contrary to the art compound that did not inhibit the enzyme 2 hours after dilution with the % recovery shown below.

TABLE 23

| Example # | Compound inhibits the enzyme 2 hours after dilution | % Recovery |
|---|---|---|
| 1 | Yes | −3.89, 9.68 |
| 2 | Yes | −6.77 |
| 3 | Yes | 10.7 |
| 4 | Yes | 3.86 |
| 5 | Yes | 8.17 |
| 6 | Yes | −2.95 |
| 7 | Yes | −10.2 |

TABLE 23-continued

| Example # | Compound inhibits the enzyme 2 hours after dilution | % Recovery |
|---|---|---|
| 8 | Yes | −2.75 |
| 9 | Yes | −15.3 |
| 10 | Yes | −17.8 |
| 11 | Yes | −11.2 |
| 12 | Yes | −8.19 |
| 13 | Yes | −5.38 |
| 14 | Yes | −16.1 |
| 15 | Yes | 3.36 |
| 16 | Yes | −20.6 |
| 17 | Yes | −20.7 |
| 18 | Yes | −9.69 |
| 19 | Yes | −8.56 |
| 22 | Yes | −19.7 |
| 23 | Yes | −19.7 |
| 24 | Yes | −17.6 |
| 25 | Yes | −17.1 |
| 26 | Yes | −29.3 |
| *Art compound | No | 45.1 |

*Art compound, (4S)-3-(2-{[(1S)-1-{4-[(4-Acetylpiperazin-1-yl)methyl]phenyl}ethyl]amino}pyrimidin-4-yl)-4-(propan-2-yl)-1,3-oxazolidin-2-one, prepared as in WO13/046136, example number 556.

This data demonstrates that the compounds act in a manner consistent with covalent inhibition of mutant IDH1 since dilution of the inhibitor does not result in recovery of enzyme activity.

Biochemical Assays for Wild-Type IDH1 and IDH2 Enzymes

IDH1 and IDH2 enzymes catalyze the conversion of isocitrate to αKG. Wild-type IDH1 (National Center for Biotechnology Information, Accession: NP_001269316.1) and IDH2 (National Center for Biotechnology Information, Accession: EAX02082.1) proteins containing N-terminal His-tag are expressed in $E.\ coli$ and purified using nickel affinity chromatography by methods commonly used and well known to those skilled in the art. The enzyme assays are carried out in V-bottom 96 well polypropylene plates containing 100 mM Tris-HCl buffer at pH 7.5, 1 mM DTT, 0.005% TRITON™ X-100, 120 mM NaCl. For the IDH1 wild-type assay isocitrate, NADP$^+$ and MnCl$_2$ are included at the concentrations of 85 μM, 50 μM and 20 μM respectively. For the IDH2 wild-type assay isocitrate, NADP$^+$ and MnCl$_2$ are included at the concentrations of 30 μM, 50 μM and 10 μM respectively. Inhibitors dissolved in a DMSO stock solution are diluted in the reaction mixture at a final DMSO concentration of 4%. The enzyme assay is terminated (quenched) by adding ACN (50:50) containing d (d$_6$-αKG) as an internal standard for mass spectrometry analysis. Ten microliters of reaction mixture is combined with 100 μL of water, 50 μL of 1 M O-benzylhydroxylamine in pyridine buffer (8.6% pyridine, pH 5), and 50 μL of 1 M EDC in pyridine buffer. Following derivatization at room temperature for one hour, samples are extracted with EtOAc (600 μL). Four hundred L of the upper layer is removed, dried under heated nitrogen, and reconstituted with MeOH/water (1:1) (100 μL). Ten μL of derivatized sample is injected onto an LC-MS system consisting of a Shimadzu Prominence 20A HPLC system and a Thermo Quantum Ultra™ triple quadrupole mass spectrometer. Analytes are separated on a Waters XBridge™ C18 column (2.1×50 mm, 3.5 m) with a flow rate of 0.6 mL/minute. Mobile phase A is 0.1% formic acid in water and mobile phase B is MeOH. The αKG signal detected is transformed into analyte concentration using a calibration curve generated using known αKG concentrations. For each compound tested, the % inhibition is calculated using a DMSO control sample as 0% inhibition and a no enzyme control as 100% inhibition. IC$_{50}$ values are obtained from the individual % inhibition values at different compound concentrations using a 4-parameter equation. These calculations are carried out using Activity Base (IDBS) or Screener (Genedata) data analysis programs.

The following Examples in Table 24 are tested essentially as described above for Biochemical Assays for IDH1 and IDH2 Mutant Enzymes and are less active at inhibiting the IDH1 wild-type enzyme compared to the IDH1 R132H or R132C mutant enzymes.

TABLE 24

| Example # | IDH1 Wild-Type IC$_{50}$ (μM) |
|---|---|
| 1 | 1.56 ± 0.20, n = 2 |
| 2 | 3.15 ± 0.07, n = 2 |
| 3 | 15.5 ± 0.5, n = 2 |
| 4 | 6.76 ± 1.35, n = 2 |
| 5 | 2.46 ± 0.30, n = 2 |
| 11 | 2.2 |
| 26 | 0.145 |

Mean = ± SEM (SEM = standard error of the mean)

Cell-Based Assays for IDH1 Mutant Inhibitors

To test the cellular inhibition of IDH1 mutant R132C, the fibrosarcoma cell line HT1080 (ATCC) is used. For testing cell-based inhibition of the R132H mutation, the U87MG glioma cell line (ATCC) is stably transfected with a DNA construct expressing the R132H mutant enzyme prepared by methods well known and routinely used by those skilled in the art.

HT1080 Cell Assay

Fifteen thousand cells are plated in poly-D-lys coated 96 well plates (15,000 cells/well) 18-24 hours prior to treatment with compounds. Four hours prior to compound treatment, cells are glutamine-starved by removing normal media and replacing with glutamine-free media. Following starvation, cells are then treated with different concentrations of test compounds (20 μM to 1 nM) dissolved in glutamine free media containing DMSO at a final concentration of 0.2%. The initial compound incubation is for 1 hour at 37° C./5% CO$_2$. After 1 hour, glutamine is added to a final 2 mM concentration and the treated cells are then incubated for a further 18 hours at 37° C./5% CO$_2$. Following the 18 hour incubation, intracellular 2HG and αKG are analyzed in cell lysates. Lysates are prepared following removal of media and addition of buffer containing 25 mM Tris-HCl pH 7.5, 150 mM NaCl, 1 mM EDTA, 1 mM EGTA/1% Triton-X 100 to the cells. An aliquot of lysate is added to a mix of d$_6$-αKG and d$_5$-3HG as internal standards and the mixture is treated with O-benzylhydroxylamine in the presence of EDC and pyridine. Analyte derivatives are then extracted with EtOAc, dried, and then reconstituted with 50% MeOH in H$_2$O. Samples prepared as described are injected into the HPLC to separate 2HG and αKG derivatives (and corresponding internal standards) using a reverse phase chromatography in a C18 column. Analysis of the samples is carried out using a 6460 triple quadrupole mass spectrometer (G6460A Agilent). The 2HG and αKG signals detected are transformed into analyte concentration using the ratio of αKG/d$_6$-αKG and the ratio of 2HG/d$_5$-3HG that is extrapolated within a calibration curve. Percent inhibition for each individual sample is obtained after normalizing calculated 2HG or αKG concentration to maximum and minimum references obtained in the presence and in the absence of glutamine during cell treatment with compounds. $IC_{50}$ values are obtained from individual % inhibition using a sigmoidal dose-response 4-parameter equation. These calculations are carried out automatically using Activity Base (IDBS) or Screener (Genedata) data analysis programs.

The results of this assay demonstrate that the tested Examples in Table 25 inhibit production of 2-hydroxyglutarate, indicating the inhibition of mutant IDH1 R132C in cells in this assay. αKG, a metabolite generated by wild-type IDH1 is not affected by the inhibitors, indicating the compounds are selective for mutant IDH1 over wild type IDH1 in cells in this assay. The resulting $IC_{50}$ values for the following Examples are shown in Table 25

TABLE 25

| Example # | HT1080 (R132C, 2-hydroxyglutarate) $IC_{50}$ (μM) | HT1080 (R132C, αKG) $IC_{50}$ (μM) |
|---|---|---|
| 1 | 0.0228 ± 0.0068, n = 7 | >20.0 |
| 2 | 0.0355 | >20.0 |
| 3 | 0.261 | >20.0 |
| 4 | 0.0507 ± 0.0133, n = 3 | >20.0 |
| 5 | 0.0244 | >20.0 |
| 6 | 0.0465 ± 0.0037, n = 2 | >20.0 |
| 7 | 0.0744 | >20.0 |
| 8 | 0.0696 ± 0.0193, n = 2 | >20.0 |
| 9 | 0.0685 | >20.0 |
| 10 | 0.0639 | >20.0 |
| 11 | 0.0441 ± 0.0133, n = 3 | >20.0 |
| 12 | 0.0474 | >20.0 |
| 13 | 0.211 ± 0.038, n = 2 | >20.0 |
| 14 | 0.0516 | >20.0 |
| 15 | 0.0275 | >20.0 |
| 16 | 0.0192 | >20.0 |
| 17 | 0.0118 | >20.0 |
| 18 | 0.0391 | >20.0 |
| 19 | 0.0265 | >20.0 |
| 20 | 0.00112 ± 0.00022, n = 2 | >20 |
| 21 | 0.000354 | >20 |
| 22 | 0.000691 ± 0.000026, n = 2 | >0.2 |
| 23 | 0.00103 ± 0.00033, n = 2 | >0.2 |
| 24 | 0.00106 ± 0.00038, n = 3 | >20 |
| 25 | 0.00168 ± 0.00057, n = 3 | >20 |
| 26 | 0.00273 ± 0.00225, n = 2 | |
| *Art compound | 0.298 ± 0.112, n = 4 | >20.0 |

Mean = ± SEM (SEM = standard error of the mean)
*Art compound, (4S)-3-(2-{[(1S)-1-{4-[(4-Acetylpiperazin-1-yl)methyl]phenyl}ethyl]amino}pyrimidin-4-yl)-4-(propan-2-yl)-1,3-oxazolidin-2-one, prepared as in WO13/046136, example number 556.

U87MG/IDH1R132H Cell Assay

Cells are plated in poly-D-lys coated 96 well plates (12,000 cells/well) 18-24 hours previous to treatment with compounds. Four hours prior to compound treatment, cells are glutamine-starved by removing normal media and replacing with glutamine-free media. Following starvation, cells are then treated with different concentrations of test compounds (20 μM to 1 nM) dissolved in glutamine free media containing DMSO at a final concentration of 0.2%. The initial compound incubation is for 1 hour at 37° C./5% $CO_2$. After 1 hour, glutamine is added to a final 2 mM concentration and the treated cells are then incubated for a further 18 hours at 37° C./5% $CO_2$. Intracellular 2HG is analyzed in cell lysates obtained after media removal and treatment with lysis buffer (25 mM Tris-HCl pH 7.5, 150 mM NaCl, 1 mM EDTA, 1 mM EGTA/1% Triton-X 100). Cell lysates are conserved at −80° C. until processing. For analyte extraction, an aliquot of thawed lysate is transferred to a deep 96-well plate and treated with cold MeOH containing $d_5$-3HG as an internal standard followed by chloroform and $H_2O$ (1:4:3:2). The upper phase is collected after separation and injected in HPLC to separate 2HG (and internal standard) using hydrophilic interaction (HILIC) chromatography coupled to MS/MS detection in a 6460 triple quadrupole mass spectrometer. Percent inhibition for each individual sample is obtained after normalizing calculated 2HG concentration to maximum and minimum references obtained in the presence and in the absence of glutamine during cell treatment with compounds. $IC_{50}$ values are obtained from individual % inhibition using a sigmoidal dose-response 4-parameter equation. These calculations are carried out automatically using Activity Base (IDBS) or Screener (Genedata) data analysis programs.

The following Examples are tested essentially as described above and exhibit inhibition activity against mutant IDH1/R132H in U87MG cells in this assay as shown in Table 26 below.

TABLE 26

| Example # | U87MG (IDH1/R132H 2-hydroxyglutarate $IC_{50}$ (μM) |
|---|---|
| 1 | 0.00313 ± 0.00069, n = 7 |
| 2 | 0.00627 |
| 3 | 0.0115 |
| 4 | 0.00716 ± 0.00149, n = 3 |
| 5 | 0.0101 |
| 6 | 0.00653 |
| 7 | 0.0194 |
| 8 | 0.0186 |
| 9 | 0.00632 |
| 10 | 0.0162 |
| 11 | 0.00518 ± 0.00156, n = 3 |
| 12 | 0.00452 |
| 13 | 0.0151 ± 0.0080, n = 2 |
| 14 | 0.00328 |
| 15 | 0.00502 |
| 16 | 0.00377 |
| 17 | 0.00228 |
| 18 | 0.00776 |
| 19 | 0.00389 |
| 20 | 0.000693 |
| 21 | 0.000563 |
| 22 | 0.000443 ± 0.000146, n = 2 |
| 23 | 0.000531 ± 0.000273, n = 2 |
| 24 | 0.000257 ± 0.000089, n = 2 |
| 25 | 0.000348 ± 0.000169, n = 2 |
| 26 | 0.000355 |
| *Art compound | 0.166 ± 0.040, n = 2 |

Mean = ± SEM (SEM = standard error of the mean)
*Art compound, (4S)-3-(2-{[(1S)-1-{4-[(4-Acetylpiperazin-1-yl)methyl]phenyl}ethyl]amino}pyrimidin-4-yl)-4-(propan-2-yl)-1,3-oxazolidin-2-one, prepared as in WO13/046136, example number 556.

In Vivo 2-Hydroxyglutarate Assay

For in vivo testing of IDH1 inhibitors, sub-cutaneous xenograft tumors are grown in athymic nude mice (20-22 g, Harlan Laboratories) following implantation of TB08-0537 (TB08) cells (secondary glioblastoma carrying R132H mutant IDH1; heterozygous human; WO 2013/086506). Mice are fed and watered ad libitum and are acclimatized for 1 week prior to implantation of cells. TB08 are implanted as tumor fragments directly into the right rear flank. Tumor volumes are measured by caliper twice weekly and tumor volume is calculated using $0.536 \times L \times W^2$, where L=length and W=width. When tumor volumes reach 150-400 $mm^3$, animals are randomized, placed into groups (n=3-6 per group) and dosed with IDH1 inhibitors or vehicle control.

For IDH1 inhibitors, compounds are formulated in vehicle containing 20% Captisol® in 25 mM phosphate buffer, pH 2 with 1 mol eq 1N HCl. Compounds are bath sonicated to obtain suspension. Compounds are dosed on a milligram per kilogram (mpk) basis via oral gavage in a final volume of 0.2 ml. To determine inhibition of 2HG, compounds are dosed once daily (QD) for 6 days (total number of doses=6). Twelve hours following the last dose, mice are euthanized with isofluorane anesthesia and cervical dislocation. Vehicle control mice receive the same dosing schedule but without addition of IDH1 inhibitor compound. Tumors are excised, put into labeled tubes, and immediately frozen in liquid nitrogen. Tumors are stored at −80° C. for processing.

Preparation of Tumor Lysates

XY Lite buffer is prepared in molecular grade water and contains the following components: 25 mM Tris, pH 7.5, 150 mM NaCl, 1% Triton X-100, 1 mM EDTA, 1 mM EGTA. To XY Lite (40 ml), 800 µl of Halt Protease and Phosphatase Inhibitors cocktail (Halt™ Protease and Phosphatase Inhibitor Cocktail, EDTA-Free Thermo Scientific, Cat#78441) is added. Samples are vortexed and then chilled on ice. Orange cap lysing-A tubes are labeled and placed in a rack on ice. A ceramic mortar and pestle is placed in dry ice to cool. A 2×2 inch square of aluminum foil is placed in the bottom of the mortar. A tumor sample is transferred to the pre-chilled mortar on the foil square. Liquid nitrogen (about 5 ml) is added and allowed to evaporate, super-freezing the tumor. Another piece of foil is placed over the tumor and the tumor smashed to small pieces with the ceramic pestle. The crushed tumor is quickly transferred to the lysing tube. Ice-cold XY Lite (500 µL) is added to each tube and capped. Tumors are then processed on the FastPrep-24 MP Biomedicals by spinning twice for 35 seconds each at speed setting 5. Samples are then centrifuged in Beckman Microfuge R at 4° C. at 14,000 rpm for 30 minutes. Supernatant is transferred to a pre-chilled 96 deep well plate. The pellet is discarded.

Protein Assay

A protein assay dilution plate is first generated by adding XY buffer (145 µl) to a non-sterile 96 well round bottom Corning plate. To, this, tumor lysate (5 µL) is added and gently mixed. The plate is kept on ice. Serial dilutions of BSA standard (Thermo Scientific cat. 23209 2 mg/mL) are set-up as follows: Five 0.5 mL tubes are placed in a rack and XY buffer (60 µL) is added to each. Stock BSA (60 µl) is added to first tube and vortexed. Sixty µl from the first tube is transferred to the next tube, vortexed, and so forth, until the dilution series is complete as follows: Tube 1=stock BSA, tubes 2-5 are 1:2 serial dilutions, tube 6=XY buffer alone. Thermo BCA Protein Assay reagents are mixed according to manufacturer instructions. Mixed BCA Reagent (200 al) is added to each sample and incubated for 15 minutes. The protein assay results are read on SOFTmax Pro Plate Reader. Based on protein assay results, the appropriate amount of XY buffer is added to each tumor lysate to generate a final protein concentration of 5 mg/mL. All samples are labeled and stored at −80° C.

Metabolite Analysis in Tumor Lysates

The in vivo effects of IDH1 inhibition on the concentrations of total 2HG and αKG is determined by liquid chromatography-mass spectrometry (LC-MS) analysis of tumor xenografts. The method utilizes derivatization with O-benzylhydroxylamine prior to analysis by LC-MS. Ten microliters of each tumor lysate is placed into a deep-well 96-well plate and combined with 100 µL of internal standard solution containing 10 µM $d_5$-3HG and 10 µM $d_6$-αKG. 50 µL of 1 M O-benzylhydroxylamine in pyridine buffer (8.6% pyridine, pH 5) and 50 µL of 1 M EDC in pyridine buffer is added to each sample. The derivatization reaction proceeds at room temperature for one hour. Using a Beckman Biomek FX liquid handler EtOAc (600 µL) is added to each sample. Plates are sealed and vortexed for 5 minutes, then they are centrifuged for 5 minutes at 4000 rpm in Eppendorf 5810R centrifuge. Four hundred L of the upper layer is transferred to a new 96-well plate. Samples are dried under heated nitrogen at 50° C. and reconstituted with 100 µL of MeOH/water (1:1). One microliter of derivatized sample is injected onto an LCMS system consisting of a Shimadzu Prominence 20A HPLC system and a Thermo Quantum Ultra™ triple quadrupole mass spectrometer. Analytes are separated on a Water XBridge™ C18 column (2.1×50 mm, 3.5 m) with a flow rate of 0.6 mL/minute. Mobile phase A is 0.1% formic acid in water and mobile phase B is MeOH. The gradient profile is: 0 minutes, 5% B; 3 minutes, 100% B; 4.00 minutes, 100% B; 4.1 minutes, 5% B; 5.50 minutes, stop. The mass spectrometer utilizes a HESI-II probe operated in positive ion selected reaction monitoring mode. Calibration curves are constructed by plotting analyte concentrations vs. analyte/internal standard peak area ratios and performing a quadratic fit of the data using a 1/concentration weighting with Xcalibur™ software. Analyte concentrations for the unknowns are back-calculated from the calibration curves. Metabolite data from the LCMS assay is expressed in nmol/mg protein. The average 2HG level in the vehicle treated group is used to determine the 0% inhibition control. The % inhibition in each inhibitor treated animal is then determined relative to the vehicle control. Data are analyzed in JMP software to determine the average % inhibition in each dose group, the standard deviation, and the standard error.

Data is shown demonstrating in vivo inhibition of 2HG in IDH1 mutant xenograft mice by the compounds of the Examples identified in Table 27.

Table 27 Inhibition of 2HG assessed at different doses of inhibitor in IDH1R132H mutant xenografts.

TABLE 27

| Compound # | Dose | Number of animals | Mean % Inhibition 2HG | Std Dev | Std Err Mean |
|---|---|---|---|---|---|
| Vehicle | 0 | 5 | 0.00 | 22.31 | 9.98 |
| Ex 4 | 1.875 | 5 | 35.53 | 14.86 | 6.65 |
| Ex 4 | 3.75 | 5 | 61.72 | 10.34 | 4.62 |
| Ex 4 | 7.5 | 5 | 80.77 | 5.75 | 2.57 |
| Ex 4 | 15 | 5 | 90.83 | 1.61 | 0.72 |
| Ex 4 | 30 | 5 | 95.12 | 1.04 | 0.47 |
| Ex4 | 60 | 5 | 96.34 | 0.56 | 0.25 |
| Vehicle | 0 | 5 | 0.00 | 26.30 | 11.76 |
| Ex 11 | 1.875 | 5 | 35.21 | 17.06 | 7.63 |
| Ex 11 | 3.75 | 5 | 48.10 | 22.39 | 10.02 |
| Ex 11 | 7.5 | 5 | 77.32 | 4.52 | 2.02 |
| Ex 11 | 15 | 5 | 82.33 | 7.25 | 3.24 |
| Ex 11 | 30 | 5 | 94.82 | 0.49 | 0.22 |
| Ex 11 | 60 | 5 | 96.36 | 1.72 | 0.77 |
| Vehicle | 0 | 4 | 0.00 | 20.68 | 10.34 |
| Ex 13 | 1.875 | 4 | 28.24 | 25.11 | 12.56 |
| Ex 13 | 3.75 | 4 | 55.47 | 15.96 | 7.98 |
| Ex 13 | 7.5 | 4 | 49.22 | 16.71 | 8.36 |
| Ex 13 | 15 | 4 | 60.63 | 29.32 | 14.66 |
| Ex 13 | 30 | 4 | 82.76 | 3.20 | 1.60 |
| Ex 13 | 60 | 4 | 94.31 | 1.49 | 0.74 |
| Vehicle | 0 | 5 | 0.00 | 13.62 | 6.09 |
| Ex 15 | 1.875 | 5 | 43.13 | 20.65 | 9.23 |
| Ex 15 | 3.75 | 5 | 36.85 | 21.24 | 9.50 |
| Ex 15 | 7.5 | 5 | 63.39 | 16.75 | 7.49 |
| Ex 15 | 15 | 5 | 82.30 | 8.47 | 3.79 |
| Ex 15 | 30 | 5 | 88.51 | 2.47 | 1.10 |

TABLE 27-continued

| Compound # | Dose | Number of animals | Mean % Inhibition 2HG | Std Dev | Std Err Mean |
|---|---|---|---|---|---|
| Ex 15 | 60 | 5 | 94.53 | 1.00 | 0.45 |
| Vehicle | 0 | 5 | 0.00 | 15.48 | 6.92 |
| Ex 12 | 10 | 5 | 63.68 | 16.65 | 7.45 |
| Ex 18 | 10 | 5 | 66.96 | 15.59 | 6.97 |
| Ex 26 | 10 | 5 | 81.31 | 4.94 | 2.21 |
| Vehicle | 0 | 5 | 0.00 | 41.43 | 18.53 |
| Ex 20 | 10 | 5 | 96.67 | 1.09 | 0.49 |
| Ex 21 | 10 | 5 | 91.75 | 1.04 | 0.46 |
| Vehicle | 0 | 5 | 0.00 | 25.84 | 11.56 |
| Ex 22 | 3 | 5 | 72.19 | 15.06 | 6.73 |
| Ex 23 | 3 | 5 | 61.44 | 19.91 | 8.90 |
| Vehicle | 0 | 5 | 0.00 | 24.38 | 10.91 |
| Ex 22 | 10 | 5 | 93.67 | 2.81 | 1.26 |
| Ex 23 | 10 | 5 | 91.61 | 2.42 | 1.08 |
| Vehicle | 0 | 4 | 0.00 | 21.98 | 10.99 |
| Ex 24 | 1 | 4 | 63.28 | 10.94 | 5.47 |
| Ex 25 | 1 | 4 | 74.54 | 10.47 | 5.23 |
| Vehicle | 0 | 5 | 0.00 | 20.33 | 9.09 |
| Ex 24 | 10 | 5 | 97.41 | 1.11 | 0.50 |
| Ex 25 | 10 | 5 | 97.92 | 1.11 | 0.50 |
| Vehicle | 0 | 5 | 0.00 | 33.83 | 15.13 |
| *Art Compound | 1.875 | 5 | 33.12 | 23.02 | 10.29 |
| *Art Compound | 3.75 | 5 | 21.89 | 11.97 | 5.36 |
| *Art Compound | 7.5 | 5 | 8.01 | 13.47 | 6.02 |
| *Art Compound | 15 | 5 | 30.06 | 15.54 | 6.95 |
| *Art Compound | 30 | 5 | 37.04 | 9.87 | 4.42 |
| *Art Compound | 60 | 5 | 45.23 | 15.70 | 7.02 |

Std Dev refers to standard deviation; Std Err Mean refers to standard error of the mean.
*Art compound, (4S)-3-(2-{[(1S)-1-{4-[(4-Acetylpiperazin-1-yl)methyl]phenyl}ethyl]amino}pyrimidin-4-yl)-4-(propan-2-yl)-1,3-oxazolidin-2-one, prepared as in WO13/046136, example number 556.

What is claimed is:

1. A compound of Formula I:

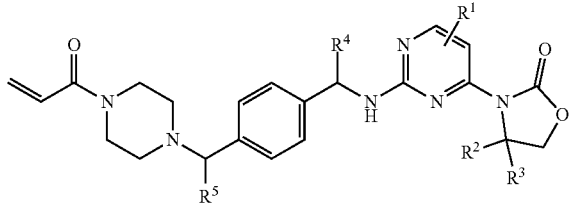

I wherein:
$R^1$ is hydrogen, $NH_2$, or fluoro;
$R^2$ and $R^3$ are methyl or hydrogen; or $R^2$ is methyl, ethyl, 1-hydroxyethyl, 1-methyoxyethyl, fluoromethyl, 1-fluoroethyl, or 1-methylethyl, and $R^3$ is hydrogen;
$R^4$ is methyl or fluoromethyl; and
$R^5$ is hydrogen, ethyl, or $CH_2$-cyclopropyl;
or a pharmaceutically acceptable salt thereof.

2. The compound of claim 1, wherein:
$R^1$ hydrogen, 6-$NH_2$, or 6-fluoro;
$R^2$ and $R^3$ are methyl; or $R^2$ is 1-methyoxyethyl, or 1-methylethyl, and $R^3$ is hydrogen;
$R^4$ is methyl; and
$R^5$ is hydrogen, ethyl, or $CH_2$-cyclopropyl;
or a pharmaceutically acceptable salt thereof.

3. The compound of claim 2, which is:
(S)-3-(2-(((S)-1-(4-((4-acryloylpiperazin-1-yl)methyl)phenyl)ethyl)amino)pyrimidin-4-yl)-4-isopropyloxazolidin-2-one;
(S)-3-(2-((1-(4-((4-acryloylpiperazin-1-yl)methyl)phenyl)ethyl)amino)-6-fluoropyrimidin-4-yl)-4,4-dimethyloxazolidin-2-one;
(R)-3-(2-(((S)-1-(4-((4-acryloylpiperazin-1-yl)methyl)phenyl)ethyl)amino)pyrimidin-4-yl)-4-((R)-1-methoxyethyl)oxazolidin-2-one; or
(R)-3-(2-(((S)-1-(4-((4-acryloylpiperazin-1-yl)methyl)phenyl)ethyl)amino)-6-fluoropyrimidin-4-yl)-4-((R)-1-methoxyethyl)oxazolidin-2-one;
or a pharmaceutically acceptable salt thereof.

4. The compound of claim 3, which is:
(S)-3-(2-((1-(4-((4-acryloylpiperazin-1-yl)methyl)phenyl)ethyl)amino)-6-fluoropyrimidin-4-yl)-4,4-dimethyloxazolidin-2-one;
or a pharmaceutically acceptable salt thereof.

5. A pharmaceutical composition comprising the compound of claim 1, or a pharmaceutically acceptable salt thereof, and a pharmaceutically acceptable carrier.

6. A method of treating a cancer expressing mutant IDH1, comprising administering to a patient in need thereof a therapeutically effective amount of the compound of Formula I:

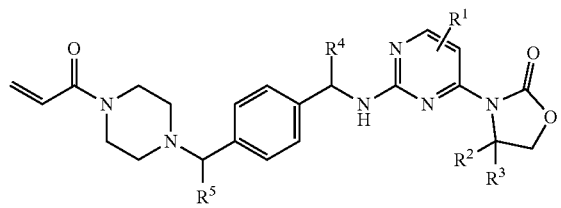

I wherein:
$R^1$ is hydrogen, $NH_2$, or fluoro;
$R^2$ and $R^3$ are methyl or hydrogen; or $R^2$ is methyl, ethyl, 1-hydroxyethyl, 1-methyoxyethyl, fluoromethyl, 1-fluoroethyl, or 1-methylethyl, and $R^3$ is hydrogen;
$R^4$ is methyl or fluoromethyl; and
$R^5$ is hydrogen, ethyl, or —$CH_2$-cyclopropyl;
or a pharmaceutically acceptable salt thereof,
wherein the cancer is acute myeloid leukemia or cholangiocarcinoma.

7. The method of claim 6, wherein the cancer is acute myeloid leukemia.

8. The method of claim 6, wherein the cancer is cholangiocarcinoma.

9. The method of claim 6, wherein the compound is:
$R^1$ hydrogen, 6-$NH_2$, or 6-fluoro;
$R^2$ and $R^3$ are methyl; or $R^2$ is 1-methyoxyethyl, or 1-methylethyl, and $R^3$ is hydrogen;
$R^4$ is methyl; and
$R^5$ is hydrogen, ethyl, or —$CH_2$-cyclopropyl;
or a pharmaceutically acceptable salt thereof.

10. The method of claim 9, wherein the compound is:
(S)-3-(2-(((S)-1-(4-((4-acryloylpiperazin-1-yl)methyl)phenyl)ethyl)amino)pyrimidin-4-yl)-4-isopropyloxazolidin-2-one;
(S)-3-(2-((1-(4-((4-acryloylpiperazin-1-yl)methyl)phenyl)ethyl)amino)-6-fluoropyrimidin-4-yl)-4,4-dimethyloxazolidin-2-one;
(R)-3-(2-(((S)-1-(4-((4-acryloylpiperazin-1-yl)methyl)phenyl)ethyl)amino)pyrimidin-4-yl)-4-((R)-1-methoxyethyl)oxazolidin-2-one; or (R)-3-(2-(((S)-1-(4-((4-acryloylpiperazin-1-yl)methyl)phenyl)ethyl)amino)-6-fluoropyrimidin-4-yl)-4-((R)-1-methoxyethyl)oxazolidin-2-one;
or a pharmaceutically acceptable salt thereof.

11. The method of claim 10, wherein the compound is:
(S)-3-(2-((1-(4-((4-acryloylpiperazin-1-yl)methyl)phenyl)ethyl)amino)-6-fluoropyrimidin-4-yl)-4,4-dimethyloxazolidin-2-one;
or a pharmaceutically acceptable salt thereof.

12. A method of inhibiting mutant IDH1, comprising administering to a patient in need thereof a therapeutically effective amount of a compound of Formula I:

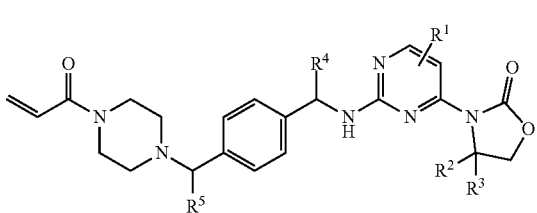

I wherein:
R¹ is hydrogen, NH₂, or fluoro;
R² and R³ are methyl or hydrogen; or R² is methyl, ethyl, 1-hydroxyethyl, 1-methyoxyethyl, fluoromethyl, 1-fluoroethyl, or 1-methylethyl, and R³ is hydrogen;
R⁴ is methyl or fluoromethyl; and
R⁵ is hydrogen, ethyl, or —CH₂-cyclopropyl;
or a pharmaceutically acceptable salt thereof.

13. The method of claim 12, wherein the compound is:
R¹ hydrogen, 6-NH₂, or 6-fluoro;
R² and R³ are methyl; or R² is 1-methyoxyethyl, or 1-methylethyl, and R³ is hydrogen;
R⁴ is methyl; and
R⁵ is hydrogen, ethyl, or —CH₂-cyclopropyl;
or a pharmaceutically acceptable salt thereof.

14. The method of claim 13, which is:
(S)-3-(2-(((S)-1-(4-((4-acryloylpiperazin-1-yl)methyl)phenyl)ethyl)amino)pyrimidin-4-yl)-4-isopropyloxazolidin-2-one;
(S)-3-(2-((1-(4-((4-acryloylpiperazin-1-yl)methyl)phenyl)ethyl)amino)-6-fluoropyrimidin-4-yl)-4,4-dimethyloxazolidin-2-one;
(R)-3-(2-(((S)-1-(4-((4-acryloylpiperazin-1-yl)methyl)phenyl)ethyl)amino)pyrimidin-4-yl)-4-((R)-1-methoxyethyl)oxazolidin-2-one; or
(R)-3-(2-(((S)-1-(4-((4-acryloylpiperazin-1-yl)methyl)phenyl)ethyl)amino)-6-fluoropyrimidin-4-yl)-4-((R)-1-methoxyethyl)oxazolidin-2-one;
or a pharmaceutically acceptable salt thereof.

15. The method of claim 14, wherein the compound is:
(S)-3-(2-((1-(4-((4-acryloylpiperazin-1-yl)methyl)phenyl)ethyl)amino)-6-fluoropyrimidin-4-yl)-4,4-dimethyloxazolidin-2-one;
or a pharmaceutically acceptable salt thereof.

* * * * *

UNITED STATES PATENT AND TRADEMARK OFFICE
CERTIFICATE OF CORRECTION

PATENT NO. : 10,696,665 B2
APPLICATION NO. : 16/302797
DATED : June 30, 2020
INVENTOR(S) : Wenceslao Lumeras Amador et al.

It is certified that error appears in the above-identified patent and that said Letters Patent is hereby corrected as shown below:

On the Title Page

"OTHER PUBLICATIONS":

Column 2, Line 3, "al.,Culture" should be -- al., Culture --.

Column 2, Line 5, "Dermeret" should be -- Dermer et --.

Column 2, Line 18, "targetdonc." should be -- targetedonc. --.

In the Claims

Column 73, Line 51, "1-methyoxyethyl," should be -- 1-methoxyethyl, --.

Column 73, Line 55, "CH2-cyclopropyl;" should be -- —CH2-cyclopropyl; --.

Column 73, Line 58, "hydrogen," should be -- is hydrogen, --.

Column 73, Line 59, "1-methyoxyethyl," should be -- 1-methoxyethyl, --.

Column 73, Line 62, "CH2-cyclopropyl;" should be -- —CH2-cyclopropyl; --.

Column 74, Line 40, "1-methyoxyethyl," should be -- 1-methoxyethyl, --.

Column 74, Line 52, "hydrogen," should be -- is hydrogen, --.

Column 74, Line 53, "1-methyoxyethyl," should be -- 1-methoxyethyl, --.

Column 75, Line 28, "1-methyoxyethyl," should be -- 1-methoxyethyl, --.

Signed and Sealed this
Tenth Day of November, 2020

Andrei Iancu
*Director of the United States Patent and Trademark Office*

CERTIFICATE OF CORRECTION (continued)
U.S. Pat. No. 10,696,665 B2

Column 76, Line 5, "hydrogen," should be -- is hydrogen, --.

Column 76, Line 6, "1-methyoxyethyl," should be -- 1-methoxyethyl, --.